(12) United States Patent
Takahashi et al.

(10) Patent No.: US 10,647,660 B2
(45) Date of Patent: May 12, 2020

(54) METHOD OF PRODUCING AROMATIC AMIDE DERIVATIVE

(71) Applicant: Mitsui Chemicals Agro, Inc., Tokyo (JP)

(72) Inventors: Yusuke Takahashi, Kawasaki (JP); Hideaki Ikishima, Chiba (JP); Hironari Okura, Omuta (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

(21) Appl. No.: 16/060,771

(22) PCT Filed: Dec. 16, 2016

(86) PCT No.: PCT/JP2016/087663
§ 371 (c)(1),
(2) Date: Jun. 8, 2018

(87) PCT Pub. No.: WO2017/104838
PCT Pub. Date: Jun. 22, 2017

(65) Prior Publication Data
US 2018/0362447 A1 Dec. 20, 2018

(30) Foreign Application Priority Data
Dec. 18, 2015 (JP) .................... 2015-247774

(51) Int. Cl.
*C07C 231/14* (2006.01)
*C07C 231/12* (2006.01)
(Continued)

(52) U.S. Cl.
CPC .......... *C07C 231/14* (2013.01); *C07C 231/12* (2013.01); *C07C 237/40* (2013.01);
(Continued)

(58) Field of Classification Search
CPC ... C07C 231/10; C07C 231/14; C07C 237/40; C07C 237/42
See application file for complete search history.

(56) References Cited

U.S. PATENT DOCUMENTS

2007/0275980 A1 11/2007 Yoshida
2009/0233962 A1 9/2009 Kai
(Continued)

FOREIGN PATENT DOCUMENTS

EP 2905274 8/2015
GB 2520098 A1 5/2015
(Continued)

OTHER PUBLICATIONS

Leonard ("Chapter Ten: Working up the Reaction" Advanced Practical Organic Chemistry, Third Ed, 2013, p. 191-208) (Year: 2013).*
(Continued)

*Primary Examiner* — Amy C Bonaparte
(74) *Attorney, Agent, or Firm* — Rankin, Hill & Clark LLP

(57) ABSTRACT

Provided is a method of producing an aromatic amide derivative represented by Formula (I), which method includes a process a containing reacting an aniline derivative represented by Formula (II) with a carboxylic acid derivative represented by Formula (III) in the presence of a base to obtain an imide compound represented by Formula (IV) and a process b containing hydrolyzing the imide compound represented by Formula (IV) to obtain the aromatic amide derivative represented by Formula (I):

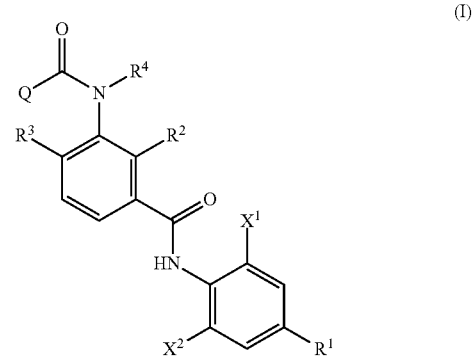

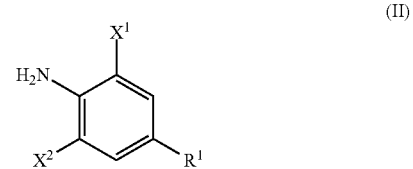

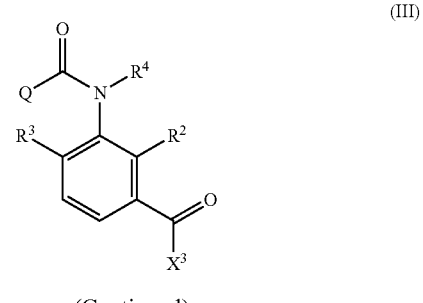

(Continued)

-continued

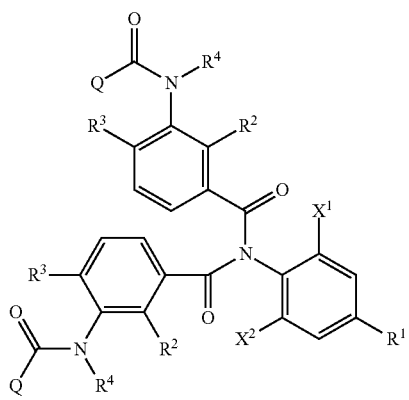

(IV)

wherein $R^1$ represents a $C_1$-$C_4$ haloalkyl group, etc.; each of $R^2$ and $R^3$ independently represents a hydrogen atom, a halogen atom, etc.; $R^4$ represents a hydrogen atom, a $C_1$-$C_4$ alkyl group, etc.; each of $X^1$ and $X^2$ independently represents a halogen atom, a $C_1$-$C_4$ haloalkyl group, etc.; and Q represents a $C_1$-$C_4$ alkyl group, a phenyl group, a pyridyl group, etc.

9 Claims, No Drawings

(51) Int. Cl.
  *C07D 213/82* (2006.01)
  *C07D 213/81* (2006.01)
  *C07C 253/30* (2006.01)
  *C07C 237/40* (2006.01)
(52) U.S. Cl.
  CPC .......... *C07C 253/30* (2013.01); *C07D 213/81* (2013.01); *C07D 213/82* (2013.01)

(56) References Cited

U.S. PATENT DOCUMENTS

| 2011/0137068 A1* | 6/2011 | Aoki | A01N 37/46 560/43 |
| 2011/0201687 A1 | 8/2011 | Kobayashi | |

FOREIGN PATENT DOCUMENTS

| WO | 2005073165 A1 | 8/2005 | |
| WO | 2006137376 A1 | 12/2006 | |
| WO | WO-2008000438 A1 * | 1/2008 | ........... C07D 213/82 |
| WO | 2010018714 A1 | 2/2010 | |
| WO | 2010018857 A1 | 2/2010 | |
| WO | WO-2010127928 A1 * | 11/2010 | ........... C07D 263/34 |
| WO | 2014161850 A1 | 10/2014 | |

OTHER PUBLICATIONS

International Search Report (ISR) dated Jan. 24, 2017 filed in PCT/JP2016/087663.
Marshall L. Morningstar et al., "Synthesis, Biological Activity, and Crystal Structure of Potent Nonnucleoside Inhibitors of HIV-a Reverse Transcriptase That Retain Activity against Mutant Forms of the Enzyme," Journal of Medicinal Chemistry, 2007, 50(17), 4003-4015, Scheme 1., Experimental Section, items of compounds (5) to (8); Cited in ISR.
Extended European Search Report dated Jun. 27, 2019 issued in the corresponding European patent application No. 16875812.6.

* cited by examiner

METHOD OF PRODUCING AROMATIC AMIDE DERIVATIVE

TECHNICAL FIELD

The present invention relates to a method of producing an aromatic amide derivative.

BACKGROUND ART

International Publications WO 2005/73165, WO 2006/137376, and WO 2010/18714 disclose various compounds as amide derivatives having pest control effects, and also disclose that an amide derivative having a perfluoroalkylated phenyl group is useful in the production of said amide derivatives.

Further, International Publications WO 2010/18857 and WO 2014/161850 disclose a method of producing said amide derivatives.

SUMMARY OF INVENTION

Technical Problem

Although the amide derivatives are synthesized in WO 2010/18857, their yield is 45% and thus an industrially higher yield thereof has been demanded. In WO 2014/161850, the amide derivatives are synthesized in high yield by way of a protective compound, but the number of processes increases and thus an environmentally shorter process has been desired.

In view of the foregoing problems, the present invention aims to provide a method of producing an aromatic amide derivative in high yield with short processes.

Solution to Problem

The present inventors have made intensive studies in order to solve the above problems and have found that aromatic amide derivatives are obtained in high yield with short processes, thereby completing the present invention. Such aromatic amide derivatives are insecticides having a high insecticidal activity.

That is, the present invention includes the following embodiments.

<1> A method of producing an aromatic amide derivative represented by the following Formula (I), which method includes the following process a and process b:

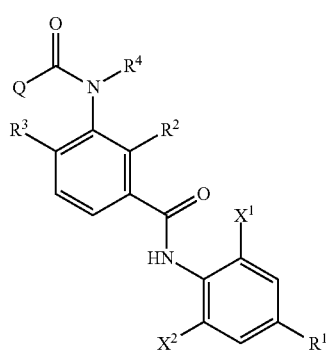

(I)

in Formula (I), $R^1$ represents a halogen atom; a $C_1$-$C_4$ haloalkyl group; or a substituted $C_1$-$C_4$ haloalkyl group (in $R^1$, the term "substituted" means substituted by 1 to 8 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group);

each of $X^1$ and $X^2$ independently represents a hydrogen atom, a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, a nitro group, a $C_1$-$C_4$ alkylcarbonyl group, or a $C_1$-$C_4$ haloalkylcarbonyl group;

each of $R^2$ and $R^3$ independently represents a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group;

$R^4$ represents a hydrogen atom; a $C_1$-$C_4$ alkyl group; a substituted $C_1$-$C_4$ alkyl group; a $C_1$-$C_4$ haloalkyl group; a substituted $C_1$-$C_4$ haloalkyl group; a $C_1$-$C_4$ alkylcarbonyl group; a substituted $C_1$-$C_4$ alkylcarbonyl group; a $C_1$-$C_4$ haloalkylcarbonyl group; a substituted $C_1$-$C_4$ haloalkylcarbonyl group; a $C_1$-$C_4$ alkoxycarbonyl group; a substituted $C_1$-$C_4$ alkoxycarbonyl group; a $C_1$-$C_4$ haloalkoxycarbonyl group; a substituted $C_1$-$C_4$ haloalkoxycarbonyl group; a $C_1$-$C_4$ alkylsulfonyl group; a substituted $C_1$-$C_4$ alkylsulfonyl group; a $C_1$-$C_4$ haloalkylsulfonyl group; or a substituted $C_1$-$C_4$ haloalkylsulfonyl group (in $R^4$, the term "substituted" means substituted by 1 to 9 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a $C_1$-$C_4$ alkylcarbonyl group, a $C_1$-$C_4$ alkoxycarbonyl group, a di-$C_1$-$C_4$ alkylaminocarbonyl group, a cyano group, and a nitro group); and Q represents a $C_1$-$C_4$ alkyl group; a substituted $C_1$-$C_4$ alkyl group; a $C_1$-$C_4$ haloalkyl group; a substituted $C_1$-$C_4$ haloalkyl group; a $C_1$-$C_4$ alkylaminocarbonyl group; a $C_1$-$C_4$ haloalkylaminocarbonyl group; a di-$C_1$-$C_4$ alkylaminocarbonyl group; a di-$C_1$-$C_4$ haloalkylaminocarbonyl group; a phenyl group; a substituted phenyl group; a heterocyclic group; or a substituted heterocyclic group (when Q is "a substituted $C_1$-$C_4$ alkyl group" or "a substituted $C_1$-$C_4$ haloalkyl group", the term "substituted" means substituted by 1 to 9 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a C haloalkylthio group, a $C_1$-$C_4$ alkylamino group, a di-$C_1$-$C_4$ alkylamino group, a cyano group, and a nitro group. Also, when Q is "a substituted phenyl group", the term "substituted" means substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a C alkylthio group, a $C_1$-$C_4$ haloalkylthio group, a C alkylamino group, a di-$C_1$-$C_4$ alkylamino group, a cyano group, and a nitro group. Further, when Q is "a substituted heterocyclic group", the term "substituted" means substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a C haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group. Moreover, said heterocyclic group is a pyridyl group, a pyridyl-N-oxide group, a pyrimidyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.); and wherein the process a includes reacting an aniline derivative represented by the following Formula (II) with a carboxylic acid derivative represented by the following Formula (III), in the presence of a base, to thereby obtain an imide compound represented by the following Formula (IV):

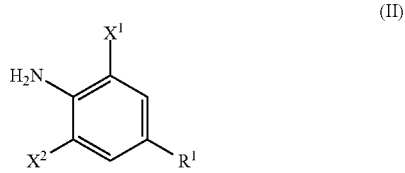
(II)

in Formula (II), $R^1$, $X^1$, and $X^2$ are the same as $R^1$, $X^1$, and $X^2$ in Formula (I), Formula (III)

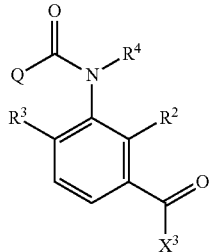
(III)

in Formula (III), $X^3$ represents a halogen atom or a $C_1$-$C_4$ alkoxy group, and $R^2$, $R^3$, $R^4$, and Q are the same as $R^2$, $R^3$, $R^4$, and Q in Formula (I), Formula (IV)

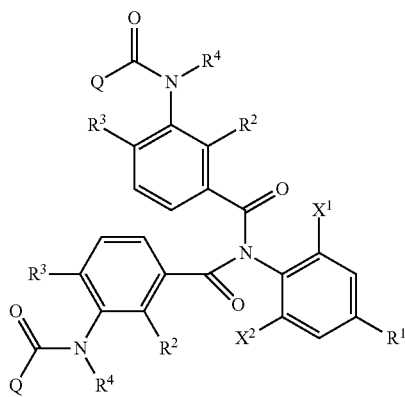
(IV)

in Formula (IV), $R^1$, $X^1$, $X^2$, $R^2$, $R^3$, $R^4$, and Q are the same as $R^1$, $X^1$, $X^2$, $R^2$, $R^3$, $R^4$, and Q in Formula (I), and two of $R^1$, $X^1$, $X^2$, $R^2$, $R^3$, $R^4$, and Q may be the same or different at each occurrence, respectively, and the process b includes hydrolyzing the imide compound represented by Formula (IV) to thereby obtain the aromatic amide derivative represented by Formula (I).

<2> The method of producing an aromatic amide derivative according to <1>, wherein:

each of $X^1$ and $X^2$ in Formulae (I), (II) and (IV) independently represents a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, or a $C_1$-$C_4$ haloalkylsulfonyl group;

each of $R^2$ and $R^3$ in Formulae (I), (III) and (IV) independently represents a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group; and $R^4$ in Formulae (I), (III) and (IV) represents a hydrogen atom, a $C_1$-$C_4$ alkyl group, a substituted $C_1$-$C_4$ alkyl group, a $C_1$-$C_4$ haloalkyl group, a substituted $C_1$-$C_4$ haloalkyl group, a $C_1$-$C_4$ alkylcarbonyl group, a $C_1$-$C_4$ haloalkylcarbonyl group, a $C_1$-$C_4$ alkoxycarbonyl group, a $C_1$-$C_4$ haloalkoxycarbonyl group, a $C_1$-$C_4$ alkylsulfonyl group, or a $C_1$-$C_4$ haloalkylsulfonyl group (in $R^4$, the term "substituted" means substituted by 1 to 9 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a $C_1$-$C_4$ alkylcarbonyl group, a $C_1$-$C_4$ alkoxycarbonyl group, a di-$C_1$-$C_4$ alkylaminocarbonyl group, a cyano group, and a nitro group).

<3> The method of producing an aromatic amide derivative according to <1> or <2>, wherein:

$R^2$ in Formulae (I), (III) and (IV) represents a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group;

$R^3$ in Formulae (I), (III) and (IV) represents a hydrogen atom, a halogen atom, a $C_1$-$C_4$ alkoxy group, a cyano group, or a nitro group; and Q in Formulae (I), (III) and (IV) represents a $C_1$-$C_4$ alkylaminocarbonyl group, a $C_1$-$C_4$ haloalkylaminocarbonyl group, a di-$C_1$-$C_4$ alkylaminocarbonyl group, a di-$C_1$-$C_4$ haloalkylaminocarbonyl group, a phenyl group, a substituted phenyl group, a heterocyclic group, or a substituted heterocyclic group (when Q is "a substituted phenyl group", the term "substituted" means substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group. Further, when Q is "a substituted heterocyclic group", the term "substituted" means substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group.).

<4> The method of producing an aromatic amide derivative according to any one of <1> to <3>, wherein:

$R^2$ in Formulae (I), (III) and (IV) represents a hydrogen atom, a halogen atom, a $C_1$-$C_4$ alkoxy group, a $C_1$-$C_4$ alkylamino group, a di-$C_1$-$C_4$ alkylamino group, a cyano group, or a nitro group; and $R^4$ in Formulae (I), (III) and (IV) represents a hydrogen atom, a $C_1$-$C_4$ alkyl group, or a $C_1$-$C_4$ haloalkyl group.

<5> The method of producing an aromatic amide derivative according to any one of <1> to <4>, wherein:

$R^2$ in Formulae (I), (III) and (IV) represents a hydrogen atom, a halogen atom, or a $C_1$-$C_4$ alkoxy group;

$R^3$ in Formulae (I), (III) and (IV) represents a hydrogen atom, a halogen atom, or a cyano group; and Q in Formulae (I), (III) and (IV) represents a di-$C_1$-$C_4$ alkylaminocarbonyl group, a phenyl group, a substituted phenyl group, a heterocyclic group, or a substituted heterocyclic group (when Q is "a substituted phenyl group", the term "substituted" means substituted by 1 to 5 substituents, which may be the same or different, selected from the group consisting of a halogen atom, a cyano group, a nitro group, and a $C_1$-$C_4$ haloalkyl group. Further, when Q is "a substituted heterocyclic group", the term "substituted" means substituted by 1 to 4 substituents, which may be the same or different, selected from the group consisting of a halogen atom, a cyano group, a nitro group, and a $C_1$-$C_4$ haloalkyl group.).

<6> The method of producing an aromatic amide derivative according to any one of <1> to <5>, wherein:

$R^2$ in Formulae (I), (III) and (IV) represents a hydrogen atom or a halogen atom;

$R^4$ in Formulae (I), (III) and (IV) represents a hydrogen atom or a $C_1$-$C_4$ alkyl group; and Q in Formulae (I), (III) and (IV) represents a phenyl group, a substituted phenyl group, a pyridyl group, or a substituted pyridyl group (when Q is "a substituted phenyl group", the term "substituted" means substituted by 1 to 5 substituents, which may be the same or different, selected from the group consisting of a halogen atom, a cyano group, and a nitro group. Further, when Q is "a substituted pyridyl group", the term "substituted" means substituted by 1 to 4 substituents, which may be the same or different, selected from the group consisting of a halogen atom, a cyano group, a nitro group, and a $C_1$-$C_4$ haloalkyl group.).

<7> The method of producing an aromatic amide derivative according to any one of <1> to <6>, in which the method further includes the following process c, process d, and process e, wherein:

the process c includes obtaining a carboxylic acid compound represented by the following Formula (V) produced together with the aromatic amide derivative represented by Formula (I) in the process b, and halogenating or esterifying the carboxylic acid compound, to thereby obtain a carboxylic acid derivative reproducing compound represented by the following Formula (IIIa):

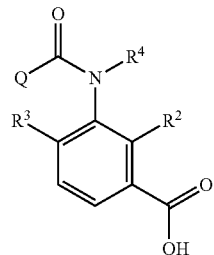

(V)

in Formula (V), $R^2$ represents a hydrogen atom, a halogen atom, a $C_1$-$C_4$ alkoxy group, a $C_1$-$C_4$ alkylamino group, a di-$C_1$-$C_4$ alkylamino group, a cyano group, or a nitro group;

$R^3$ represents a hydrogen atom or a halogen atom;

$R^4$ represents a hydrogen atom, a $C_1$-$C_4$ alkyl group, or a $C_1$-$C_4$ haloalkyl group; and Q represents a di-$C_1$-$C_4$ alkylaminocarbonyl group, a phenyl group, a substituted phenyl group, a heterocyclic group, or a substituted heterocyclic group (when Q is "a substituted phenyl group", the term "substituted" means substituted by 1 to 5 substituents, which may be the same or different, selected from the group consisting of a halogen atom, a cyano group, a nitro group, and a $C_1$-$C_4$ haloalkyl group. Further, when Q is "a substituted heterocyclic group", the term "substituted" means substituted by 1 to 4 substituents, which may be the same or different, selected from the group consisting of a halogen atom, a cyano group, a nitro group, and a $C_1$-$C_4$ haloalkyl group. Said heterocyclic group is a pyridyl group, a pyridyl-N-oxide group, a pyrimidyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.);

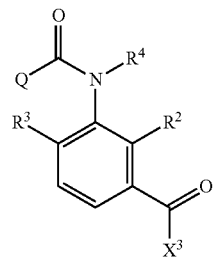

(IIIa)

in Formula (IIIa), $R^2$, $R^3$, $R^4$, $X^3$ and Q are the same as $R^2$, $R^3$, $R^4$, $X^3$ and Q in Formula (III);

the process d includes allowing the carboxylic acid derivative reproducing compound obtained in the process c and the aniline derivative represented by Formula (II) to react with each other in the presence of a base to obtain the imide compound represented by Formula (IV); and the process e includes hydrolyzing the imide compound represented by Formula (IV) obtained in the process d to obtain the aromatic amide derivative represented by Formula (I).

<8> The method of producing an aromatic amide derivative according to <7>, wherein:

$R^2$ in Formula (V) represents a hydrogen atom or a halogen atom;

$R^4$ represents a hydrogen atom or a $C_1$-$C_4$ alkyl group; and

Q represents a di-$C_1$-$C_4$ alkylaminocarbonyl group, a phenyl group, a substituted phenyl group, a pyridyl group or a substituted pyridyl group (when Q is "a substituted phenyl group", the term "substituted" means substituted by 1 to 5 substituents, which may be the same or different, selected from the group consisting of a halogen atom, a cyano group, and a nitro group. Further, when Q is "a substituted pyridyl group", the term "substituted" means substituted by 1 to 4 substituents, which may be the same or different, selected from the group consisting of a halogen atom and a $C_1$-$C_4$ haloalkyl group.).

Advantageous Effects of Invention

According to the present invention, a method of producing an aromatic amide derivative in high yield with a short process can be provided.

DESCRIPTION OF EMBODIMENTS

In this specification, the term "process" includes not only an independent process, but also a case in which the process cannot be clearly distinguished from another process, as long as the predetermined action of the process is achieved.

Further, a numerical range expressed using "to" denotes a range including numerical values described in front of and behind "to", as the minimum value and the maximum value, respectively.

The terms used in Formulae described in this specification have the definitions as described below, respectively, on the basis of their definitions.

"Halogen atom" represents a fluorine atom, a chlorine atom, a bromine atom, or an iodine atom.

The term "n-" means "normal", "i-" means "iso", "s-" means "secondary", and "t-" means "tertiary".

Concerning the expression "$C_a$-$C_b$ (wherein each of a and b represents an integer of 1 or more)", for example, "$C_1$-$C_3$" means that the number of carbon atoms is from 1 to 3, "$C_2$-$C_6$" means that the number of carbon atoms is from 2 to 6, and "$C_1$-$C_4$" means that the number of carbon atoms is from 1 to 4.

Further, in the following explanations on the substituents with a limitation of the number of carbon atoms, "$C_a$-$C_b$ XX group (wherein "XX group" represents name of a substituent group and each of a and b represents an integer of 1 or more)" means, for example, in a case of "$C_1$-$C_3$ XX group", to represent a XX group having 1 to 3 carbon atoms and also include the range covered by the substituent having each number of carbon atoms, such as a XX group having 1 carbon atom, a XX group having 2 carbon atoms and a XX group having 3 carbon atoms, as a subordinate concept. In addition, "$C_a$-$C_b$ XX group" also includes the range covered by the substituent in which the upper limit and the lower limit of the number of carbon atoms are optionally combined within the acceptable range, for example, in a case of "$C_1$-$C_3$ XX group", such as "$C_1$-$C_2$ XX group" and "$C_2$-$C_3$ XX group" are also included.

"$C_1$-$C_3$ Alkyl group" represents a linear or branched alkyl group having from 1 to 3 carbon atoms, for example, a methyl group, an ethyl group, an n-propyl group, an i-propyl group, or the like, and "$C_1$-$C_4$ alkyl group" represents a linear or branched alkyl group having from 1 to 4 carbon atoms, for example, an n-butyl group, an s-butyl group, i-butyl, a t-butyl group, or the like, in addition to the "$C_1$-$C_3$ alkyl group".

"$C_1$-$C_4$ haloalkyl group" represents a linear or branched alkyl group having from 1 to 4 carbon atoms and being substituted with one or more halogen atoms which may be the same or different, for example, a monofluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoroethyl group, a 2,2-difluoroethyl group, a 2,2,2-trifluoroethyl group, a 1-chloroethyl group, a 2-chloroethyl group, a 2,2-dichloroethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoroethyl group, a 3-fluoro-n-propyl group, a 3-chloro-n-propyl group, a 3-bromo-n-propyl group, a 1,3-difluoro-2-propyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2,2,3,3,3-pentafluoro-n-propyl group, a heptafluoro-i-propyl group, a heptafluoro-n-propyl group, a 4-fluoro-n-butyl group, a nonafluoro-n-butyl group, a nonafluoro-2-butyl group, a nonafluoro-i-butyl group, or the like.

"$C_2$-$C_4$ alkenyl group" represents an alkenyl group having from 2 to 4 carbon atoms and a double bond in the carbon chain, for example, a vinyl group, an allyl group, a 2-butenyl group, a 3-butenyl group, or the like.

"$C_2$-$C_4$ haloalkenyl group" represents a linear or branched alkenyl group having from 2 to 4 carbon atoms and a double bond in the carbon chain, and being substituted with one or more halogen atoms which may be the same or different, for example, a 3,3-difluoro-2-propenyl group, a 3,3-dichloro-2-propenyl group, a 3,3-dibromo-2-propenyl group, a 2,3-dibromo-2-propenyl group, a 4,4-difluoro-3-butenyl group, a 3,4,4-tribromo-3-butenyl group, or the like.

"$C_2$-$C_4$ alkynyl group" represents a linear or branched alkynyl group having from 2 to 4 carbon atoms and a triple bond in the carbon chain, for example, a propargyl group, a 1-butyn-3-yl group, a 1-butyn-3-methyl-3-yl group, or the like.

"$C_2$-$C_4$ haloalkynyl group" represents a linear or branched alkynyl group having from 2 to 4 carbon atoms and a triple bond in the carbon chain, and being substituted with one or more halogen atoms which may be the same or different, for example, a 3,3-difluoropropyne-1-yl group, a 3,3,3-trifluoropropyne-1-yl group, a 4,4,4-trifluoro-3,3-difluoro-butyne-1-yl group, or the like.

"$C_1$-$C_4$ alkoxy group" represents a linear or branched alkoxy group having from 1 to 4 carbon atoms, for example, a methoxy group, an ethoxy group, an n-propyloxy group, an isopropyloxy group, an n-butyloxy group, an i-butyloxy group, or the like.

"$C_1$-$C_4$ haloalkoxy group" represents a linear or branched haloalkoxy group having from 1 to 4 carbon atoms and being substituted with one or more halogen atoms which may be the same or different, for example, a trifluoromethoxy group, a 1,1,1,3,3,3-hexafluoro-2-propyloxy group, a 2,2,2-trifluoroethoxy group, a 2-chloroethoxy group, a 3-fluoro-n-propyloxy group, a 1,1,1,3,3,4,4,4-octafluoro-2-butyloxy group, or the like.

"$C_1$-$C_4$ alkylthio group" represents a linear, branched, or cyclic alkylthio group having from 1 to 4 carbon atoms, for example, a methylthio group, an ethylthio group, an n-propylthio group, an i-propylthio group, a cyclopropylthio group, an n-butylthio group, an i-butylthio group, an s-butylthio group, a t-butylthio group, a cyclopropylmethylthio group, or the like.

"$C_1$-$C_4$ haloalkylthio group" represents a linear or branched alkylthio group having from 1 to 4 carbon atoms and being substituted with one or more halogen atoms which may be the same or different, for example, a trifluoromethylthio group, a pentafluoroethylthio group, a 2,2,2-trifluoroethylthio group, a heptafluoro-n-propylthio group, a heptafluoro-i-propylthio group, a nonafluoro-n-butylthio group, a nonafluoro-i-butylthio group, a nonafluoro-s-butylthio group, a 4,4,4-trifluoro-n-butylthio group, or the like.

"$C_1$-$C_4$ alkylsulfinyl group" represents a linear, branched, or cyclic alkylsulfinyl group having from 1 to 4 carbon atoms, for example, a methylsulfinyl group, an ethylsulfinyl group, an n-propylsulfinyl group, an i-propylsulfinyl group, a cyclopropylsulfinyl group, an n-butylsulfinyl group, an i-butylsulfinyl group, or the like.

"$C_1$-$C_4$ haloalkylsulfinyl group" represents a linear or branched alkylsulfinyl group having from 1 to 4 carbon atoms and being substituted with one or more halogen atoms which may be the same or different, for example, a trifluoromethylsulfinyl group, a pentafluoroethylsulfinyl group, a 2,2,2-trifluoroethylsulfinyl group, a heptafluoro-n-propylsulfinyl group, a heptafluoro-i-propylsulfinyl group, a nonafluoro-n-butylsulfinyl group, a nonafluoro-i-butylsulfinyl group, a nonafluoro-s-butylsulfinyl group, a 4,4,4-trifluoro-n-butylsulfinyl group, or the like.

"$C_1$-$C_4$ alkylsulfonyl group" represents a linear, branched, or cyclic alkylsulfonyl group having from 1 to 4 carbon atoms, for example, a methylsulfonyl group, an ethylsulfonyl group, an n-propylsulfonyl group, an i-propylsulfonyl group, a cyclopropylsulfonyl group, an n-butylsulfonyl group, an i-butylsulfonyl group, or the like.

"$C_1$-$C_4$ haloalkylsulfonyl group" represents a linear or branched alkylsulfonyl group having from 1 to 4 carbon atoms and being substituted with one or more halogen atoms which may be the same or different, for example, a trifluoromethylsulfonyl group, a pentafluoroethylsulfonyl group, a 2,2,2-trifluoroethylsulfonyl group, a heptafluoro-n-propyl sulfonyl group, a heptafluoro-i-propyl sulfonyl group, a nonafluoro-n-butyl sulfonyl group, a nonafluoro-s-butyl sulfonyl group, or the like. "$C_1$-$C_4$ alkylamino group" represents a linear, branched, or cyclic alkylamino group having from 1 to 4 carbon atoms, for example, a methylamino group, an ethylamino group, an n-propylamino group, an i-propylamino group, an n-butylamino group, a cyclopropylamino group, or the like.

"Di-$C_1$-$C_4$-alkylamino group" represents an amino group substituted with two linear or branched alkyl groups each having from 1 to 4 carbon atoms, which may be the same or different, for example, a dimethylamino group, a diethylamino group, an N-ethyl-N-methylamino group, or the like.

"$C_1$-$C_4$ alkylcarbonyl group" represents a linear, branched, or cyclic alkylcarbonyl group having from 1 to 4 carbon atoms, for example, a formyl group, an acetyl group, a propionyl group, an isopropylcarbonyl group, a cyclopropylcarbonyl group, or the like. "$C_1$-$C_4$ haloalkylcarbonyl group" represents a linear or branched alkylcarbonyl group having from 1 to 4 carbon atoms and being substituted with one or more halogen atoms which may be the same or different, for example, a fluoroacetyl group, a difluoroacetyl group, a trifluoroacetyl group, a chloroacetyl group, a dichloroacetyl group, a trichloroacetyl group, a bromoacetyl group, an iodoacetyl group, a 3,3,3-trifluoropropionyl group, a 2,2,3,3,3-pentafluoropropionyl group, or the like.

"$C_1$-$C_4$ alkylcarbonyloxy group" represents a linear or branched alkylcarbonyloxy group having from 1 to 4 carbon atoms, for example, an acetoxy group, a propionyloxy group, or the like.

"$C_1$-$C_4$ alkoxycarbonyl group" represents a linear or branched alkoxycarbonyl group having from 1 to 4 carbon atoms, for example, a methoxycarbonyl group, an ethoxycarbonyl group, an isopropyloxycarbonyl group, or the like.

"$C_1$-$C_4$ perfluoroalkyl group" represents a linear or branched alkyl group having from 1 to 4 carbon atoms and being completely substituted with fluorine atoms, for example, a trifluoromethyl group, a pentafluoroethyl group, a heptafluoro-n-propyl group, a heptafluoro-i-propyl group, a nonafluoro-n-butyl group, a nonafluoro-2-butyl group, a nonafluoro-i-butyl group, or the like.

"$C_1$-$C_4$ perfluoroalkylthio group" represents a linear or branched alkylthio group having from 1 to 4 carbon atoms and being completely substituted with fluorine atoms, for example, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a nonafluoro-i-butylthio group, or the like.

"$C_1$-$C_4$ perfluoroalkylsulfinyl group" represents a linear or branched alkylsulfinyl group having from 1 to 4 carbon atoms and being completely substituted with fluorine atoms, for example, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a nonafluoro-i-butylsulfinyl group, or the like.

"$C_1$-$C_4$ perfluoroalkylsulfonyl group" represents a linear or branched alkylsulfonyl group having from 1 to 4 carbon atoms and being completely substituted with fluorine atoms, for example, a trifluoromethylsulfonyl group, a pentafluoroethylsulfonyl group, a heptafluoro-n-propyl sulfonyl group, a heptafluoro-i-propyl sulfonyl group, a nonafluoro-n-butyl sulfonyl group, a nonafluoro-2-butyl sulfonyl group, a nonafluoro-i-butyl sulfonyl group, or the like.

In the invention, the compounds represented by Formula (I), Formula (II), Formula (III), Formula (IIIa), Formula (IV), Formula (V), or the like may include one or two or more chiral carbon atoms or chiral centers in their structural Formulae, and thus may have two or more optical isomers. The scope of the invention encompasses all of the individual optical isomers and any mixture containing such optical isomers in any proportion.

Further, the compound represented by Formula (I), Formula (II), Formula (III), Formula (IIIa), Formula (IV), Formula (V), or the like in the invention may have two or more geometrical isomers originating from carbon-carbon double bond(s) in their structural Formulae. The scope of the invention also encompasses any mixture containing such geometrical isomers in any proportion.

The method of producing an aromatic amide derivative represented by the following Formula (I) of the invention (hereinafter, simply referred to as "production method of the invention") includes a process (process a) of obtaining an imide compound represented by Formula (IV) by reacting an aniline derivative represented by Formula (II) with a carboxylic acid derivative represented by Formula (III) in the presence of a base and a process (process b) of obtaining the aromatic amide derivative represented by Formula (I) by hydrolyzing the imide compound represented by Formula (IV).

In addition, the production method of the invention may further include, if necessary, a process (process c) of obtaining the carboxylic acid derivative reproducing compound represented by Formula (IIIa) by isolating and purifying the carboxylic acid compound represented by Formula (V) obtained together with the aromatic amide derivative represented by Formula (I) in the hydrolysis of the imide compound represented by Formula (IV) in the process b, and by halogenating or esterifying the carboxylic acid compound; a process (process d) of obtaining the imide compound represented by Formula (IV) by reacting the carboxylic acid derivative reproducing compound represented by Formula (IIIa) obtained in the process c with the aniline derivative represented by Formula (II) in the presence of a base; and a process (process e) of obtaining the aromatic amide derivative represented by Formula (I) by hydrolyzing the imide compound represented by Formula (IV) obtained in the process d.

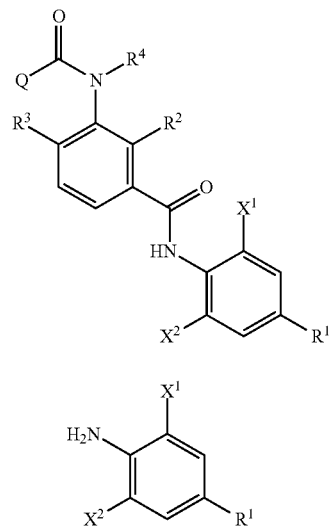

(I)

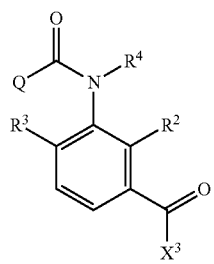

(II)

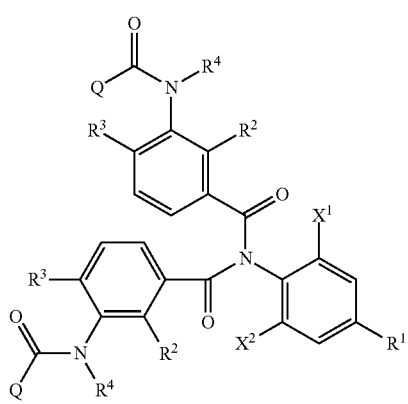

(III)

(IV)

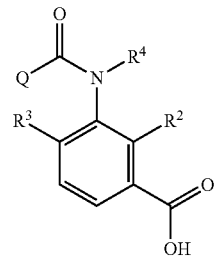

(V)

The imide compound represented by Formula (IV) in the invention is a useful intermediate particularly in producing the compound represented by Formula (I), which is useful as an insecticide.

In Formula (IV), $R^1$ represents a halogen atom; a $C_1$-$C_4$ haloalkyl group; or a $C_1$-$C_4$ haloalkyl group substituted by 1 to 8 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group, and $R^1$ is preferably a $C_1$-$C_4$ haloalkyl group.

In Formula (IV), each of $X^1$ and $X^2$ independently represents a hydrogen atom, a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, a nitro group, a $C_1$-$C_4$ alkylcarbonyl group, or a $C_1$-$C_4$ haloalkylcarbonyl group; represents preferably a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, or a $C_1$-$C_4$ haloalkylsulfonyl group; and represents more preferably a halogen atom, a $C_1$-$C_4$ alkyl group, a $C_1$-$C_4$ haloalkyl group, or a $C_1$-$C_4$ haloalkylsulfonyl group.

In Formula (IV), each of $R^2$ and $R^3$ independently represents a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group, and are preferably a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group.

$R^2$ represents more preferably a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group; even more preferably a hydrogen atom, a halogen atom, a $C_1$-$C_4$ alkoxy group, a $C_1$-$C_4$ alkylamino group, a di-$C_1$-$C_4$ alkylamino group, a cyano group, or a nitro group; especially preferably a hydrogen atom, a halogen atom, or a $C_1$-$C_4$ alkoxy group. $R^3$ represents more preferably a hydrogen atom, a halogen atom, a $C_1$-$C_4$ alkoxy group, a cyano group, or a nitro group; even more preferably a hydrogen atom, a halogen atom, a nitro group or a cyano group; and especially preferably a hydrogen atom, a halogen atom, or a cyano group.

Two of $R^2$ may be the same or different at each occurrence, and two of $R^3$ may be the same or different at each occurrence.

In Formula (IV), $R^4$ represents a hydrogen atom; a $C_1$-$C_4$ alkyl group; a $C_1$-$C_4$ haloalkyl group; a $C_1$-$C_4$ alkylcarbonyl group; a $C_1$-$C_4$ haloalkylcarbonyl group; a $C_1$-$C_4$ alkoxycarbonyl group; a $C_1$-$C_4$ haloalkoxycarbonyl group; a $C_1$-$C_4$ alkylsulfonyl group; a $C_1$-$C_4$ haloalkylsulfonyl group; or a $C_1$-$C_4$ alkyl group, a $C_1$-$C_4$ haloalkyl group, a $C_1$-$C_4$ alkylcarbonyl group, a $C_1$-$C_4$ haloalkylcarbonyl group, a $C_1$-$C_4$ alkoxycarbonyl group, a $C_1$-$C_4$ haloalkoxycarbonyl group, a $C_1$-$C_4$ alkylsulfonyl group, or a $C_1$-$C_4$ haloalkylsulfonyl group, substituted by 1 to 9 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a $C_1$-$C_4$ alkylcarbonyl group, a $C_1$-$C_4$ alkoxycarbonyl group, a di-$C_1$-$C_4$ alkylaminocarbonyl group, a cyano group, and a nitro group.

Two of $R^4$ may be the same or different at each occurrence.

$R^4$ may form a $C_1$-$C_6$ heterocyclic ring when taken together with Q.

$R^4$ represents preferably a hydrogen atom, a $C_1$-$C_4$ alkyl group, a $C_1$-$C_4$ haloalkyl group, a $C_1$-$C_4$ alkylcarbonyl group, a a $C_1$-$C_4$ alkoxycarbonyl group, or a $C_1$-$C_4$ alkylsulfonyl group; more preferably a hydrogen atom, a $C_1$-$C_4$ alkyl group, or a $C_1$-$C_4$ haloalkyl group; and even more preferably a hydrogen atom or a $C_1$-$C_4$ alkyl group.

In Formula (IV), Q represents a $C_1$-$C_4$ alkyl group; a $C_1$-$C_4$ haloalkyl group; a $C_1$-$C_4$ alkylaminocarbonyl group; a $C_1$-$C_4$ haloalkylaminocarbonyl group; a di-$C_1$-$C_4$ alkylaminocarbonyl group; a di-$C_1$-$C_4$ haloalkylaminocarbonyl group; a phenyl group; a heterocyclic group; a $C_1$-$C_4$ alkyl group or a $C_1$-$C_4$ haloalkyl group, substituted by 1 to 9 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; a phenyl group substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; or a heterocyclic group substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; wherein the heterocyclic group is a pyridyl group, a pyridyl-N-oxide group, a pyrimidyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

Two of Q may be the same or different at each occurrence.

Q represents preferably a $C_1$-$C_4$ alkylaminocarbonyl group; a $C_1$-$C_4$ haloalkylaminocarbonyl group; a di-$C_1$-$C_4$ alkylaminocarbonyl group; a di-$C_1$-$C_4$ haloalkylaminocarbonyl group; a phenyl group; a heterocyclic group; a phenyl group substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; or a heterocyclic group substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; more preferably a phenyl group; a heterocyclic group; a phenyl group substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; or a heterocyclic group substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; even more preferably a di-$C_1$-$C_4$ alkylaminocarbonyl group; a phenyl group; a heterocyclic group; a phenyl group substituted by 1 to 5 substituents, which may be the same or different, selected from the group consisting of a halogen atom, a cyano group, a nitro group, and a $C_1$-$C_4$ haloalkyl group; or a heterocyclic group substituted by 1 to 4 substituents, which may be the same or different, selected from the group consisting of a halogen atom, a cyano group, a nitro group, and a $C_1$-$C_4$ haloalkyl group; particularly preferably a phenyl group; a pyridyl group; a phenyl group substituted by 1 to 5 substituents, which may be the same or different, selected from the group consisting of a halogen atom, a cyano group, and a nitro group; or a pyridyl group substituted by 1 to 4 substituents, which may be the same or different, selected from the group consisting of a halogen atom, a cyano group, a nitro group, and a $C_1$-$C_4$ haloalkyl group.

$R^1$, $X^1$, $X^2$, $R^2$, $R^3$, $R^4$, and Q in Formula (I) have the same meanings as $R^1$, $X^1$, $X^2$, $R^2$, $R^3$, $R^4$, and Q in Formula (IV), respectively. The same shall be applied to preferred embodiments.

$R^1$, $X^1$, and $X^2$ in Formula (II) have the same meanings as $R^1$, $X^1$, and $X^2$ in Formula (IV), respectively. The same shall be applied to preferred embodiments.

$X^3$ in Formula (III) represents a halogen atom or a $C_1$-$C_4$ alkoxy group, and $R^2$, $R^3$, $R^4$, and Q have the same meanings as $R^2$, $R^3$, $R^4$, and Q in Formula (IV). The same shall be applied to preferred embodiments.

$R^2$, $R^3$, $R^4$, and Q in Formula (V) have the same meanings as $R^2$, $R^3$, $R^4$, and Q in Formula (IV), and the same shall be applied to preferred embodiments.

In the chemical structure represented by a Formula, the range of the limitations on each of and every substituent described above are combinable in any arbitrary level, and the entire range of the limitations of the chemical structures represented by the Formula resulted from the arbitrary combinations are explicitly disclosed herein, as if each and every combination was indivisually and explicitly recited.

The production method of the invention will be described as follows.

First, the process a will be described.

The process a is, as shown in the following reaction scheme, a process of obtaining an imide compound represented by Formula (IV) by reacting an aniline derivative represented by Formula (II) with a carboxylic acid derivative represented by Formula (III) in the presence of a base.

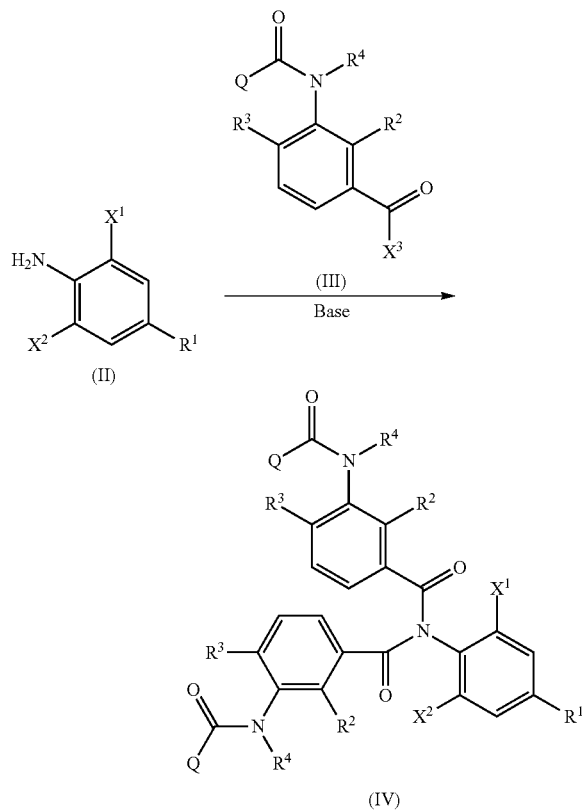

Examples of the bases to be used in the above reaction may include organic bases such as triethylamine, tri-n-butylamine, pyridine, 4-dimethylaminopyridine, 1,4-diazabicyclo[2.2.2]octane, diazabicycloundecene, and diazabicyclononene; alkali metal hydroxides such as sodium hydroxide and potassium hydroxide; carbonates such as sodium hydrogen carbonate and potassium carbonate; phosphates such as dipotassium monohydrogen phosphate and trisodium phosphate; alkali metal hydrides such as sodium hydride; alkali metal alcoholates such as sodium methoxide and sodium ethoxide; and the like. These bases may be used alone or as a mixture of two or more thereof.

Among these, the organic bases such as triethylamine, tri-n-butylamine, and 4-dimethylaminopyridine can be particularly preferably used in the above reaction.

Such base may be used in an amount appropriately selected within the range of from 0.01-fold molar equivalents to 10-fold molar equivalents, and preferably within the range of from 2-fold molar equivalents to 4-fold molar equivalents, with respect to the aniline derivative represented by Formula (II). The base may be used in an amount appropriately selected within the above range.

The above reaction may be carried out in the absence of a solvent or may be carried out in the presence of an inert solvent.

The inert solvent is not particularly limited as long as the solvent does not significantly inhibit the progress of the reaction. Examples of the inert solvent may include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; alcohols such as methanol and ethanol; ketones such as acetone, methyl isobutyl ketone, and cyclohexanone; amides such as N,N-dimethylformamide, N,N-dimethyl acetamide, 1,3-dimethyl-2-imidazolidinon, and N-methyl-2-pyrrolidone; nitriles such as acetonitrile; and dimethylsulfoxide. These solvents may be used alone or as a mixture of two or more kinds thereof.

Among them, at least one member as an inert solvent selected from the group consisting of benzene, toluene, and xylene can be particularly preferably used.

Concerning the amount of the inert solvent used, such inert solvent may be used in an amount appropriately selected within the range of from 2-fold by mass to 20-fold by mass, and preferably within the range of from 2-fold by mass to 10-fold by mass, with respect to the amount of the aniline derivative represented by Formula (II) used. The inert solvent may be used in an amount appropriately selected within the above range.

The reaction temperature in the above reaction may be appropriately selected within the range of from −20° C. to 200° C., preferably within the range of from 50° C. to 120° C., and in the case of using an inert solvent, the reaction temperature may be any temperature that is lower than or equal to the boiling point. The reaction time may be appropriately selected within the range of from several minutes to 96 hours and preferably within the range of from several minutes to 24 hours.

The amount of the carboxylic acid derivative represented by Formula (III) used in the above reaction is not particularly limited, with respect to the amount of the aniline derivative represented by Formula (II) used. For example, from the viewpoint of economy, the carboxylic acid derivative represented by Formula (III) is used preferably in an amount of from 2-fold molar equivalents to 5-fold molar equivalents, more preferably in an amount of from 2-fold molar equivalents to 3-fold molar equivalents, with respect to the amount of the aniline derivative represented by Formula (II) used.

In the process a as described above, the imide compound represented by Formula (IV), which is the aimed product, may be isolated from the reaction system after the completion of the reaction, according to a conventional method, and, if necessary, purification may be carried out by an operation such as recrystallization, column chromatography, or distillation.

The above explained reaction conditions in the process a, such as type and amount of the base, and the inert solvent, reaction temperature, reaction time, or the like are combinable in any arbitrary level, and each and every such combination is explicitly disclosed herein, as if each and every aspect was individually and explicitly recited.

The aniline derivative represented by Formula (II) can be synthesized by the method described in EP 2,319,830. Further, the carboxylic acid derivative represented by Formula (III) can be synthesized by the method described in WO 2010/018857 A1.

Next, the process b will be described.

The process b is, as shown in the following reaction scheme, a process of obtaining the aromatic amide derivative represented by Formula (I) by hydrolyzing the imide compound represented by (IV). In the process b, the carboxylic acid compound represented by Formula (V) can be obtained together with the aromatic amide derivative represented by Formula (I).

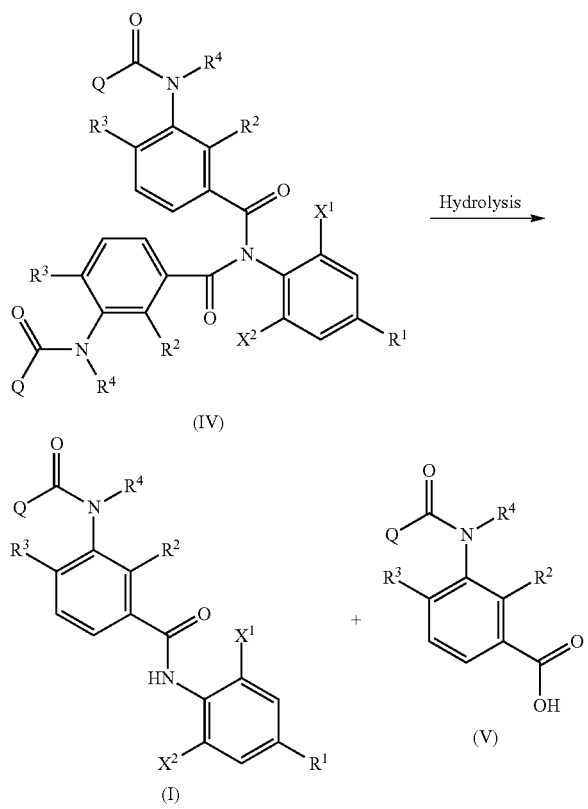

The hydrolysis in the above reaction indicates that the imide compound represented by Formula (IV) is decomposed to the aromatic amide derivative represented by Formula (I) and the carboxylic acid compound represented by Formula (V) with an acid or a base in the presence of water.

The acid used in the hydrolysis includes hydrogen chloride, hydrogen bromide, hydrogen iodide, sulfuric acid, and nitric acid, and hydrogen chloride and sulfuric acid are preferable.

The base used in the hydrolysis includes alkali metal hydroxides such as lithium hydroxide, sodium hydroxide, and potassium hydroxide; carbonates such as sodium hydrogen carbonate, sodium carbonate, and potassium carbonate; alkali metal alcoholates such as sodium methoxide and sodium ethoxide; organic bases such as triethylamine, 4-dimethylaminopyridine and pyridine; and the like. Among these, as the base, at least one member selected from the group consisting of sodium hydroxide, potassium hydroxide, sodium carbonate, potassium carbonate, and 4-dimethylaminopyridine can be particularly preferably used.

The amount of the acid or base used is, for example, in the range of from 0.5-fold molar equivalents to 20-fold molar equivalents, preferably from 0.5-fold molar equivalents to 10-fold molar equivalents, with respect to the amount of the imide compound represented by Formula (IV) used. Such acids or bases may be used in an amount appropriately selected within the above range.

The above reaction may be carried out in the absence of a solvent or may be carried out in the presence of an inert solvent.

The inert solvent is not particularly limited as long as the solvent does not significantly inhibit the progress of the reaction. Examples of the inert solvent may include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; alcohols such as methanol and ethanol; ketones such as acetone, methyl isobutyl ketone, and cyclohexanone; amides such as N,N-dimethylformamide, N,N-dimethylacetamide, 1,3-dimethyl-2-imidazolidinon, and N-methyl-2-pyrrolidone; nitriles such as acetonitrile; and dimethylsulfoxide. These solvents may be used alone or as a mixture of two or more kinds thereof.

Among them, at least one member as an inert solvent selected from the group consisting of tetrahydrofuran, methanol, 1,3-dimethyl-2-imidazolidinon, toluene, and xylene can be particularly preferably used.

Concerning the amount of the inert solvent used, such a solvent may be used, for example, in an amount appropriately selected within the range of from 1-fold by mass to 15-fold by mass, and preferably within the range of from 1-fold by mass to 10-fold by mass, with respect to the mount of the imide compound represented by Formula (IV) used. The inert solvent may be used in an amount appropriately selected within the above range.

The reaction temperature in the above reaction may be appropriately selected within the range of from −20° C. to 200° C., preferably within the range of from 50° C. to 120° C., and in the case of using an inert solvent, the reaction temperature may be any temperature that is lower than or equal to the boiling point. The reaction time may be appropriately selected within the range of from several minutes to 96 hours, and preferably within the range of from several minutes to 24 hours.

In the process b as described above, the aromatic amide derivative represented by Formula (I), which is the aimed product, may be isolated from the reaction system after the completion of the reaction, according to a conventional method, and, if necessary, purification may be carried out by an operation such as recrystallization, column chromatography, or distillation.

The above explained reaction conditions in the process b, such as type and amount of the acid, the base, and the inert solvent, reaction temperature, reaction time, or the like are combinable in any arbitrary level, and each and every such combination is explicitly disclosed herein, as if each and every aspect was individually and explicitly recited.

In the case of using an acid for hydrolysis in the process b, the carboxylic acid compound represented by Formula (V), which is obtained together with the aromatic amide derivative represented by Formula (I), may be isolated by filtration after the completion of the reaction. In the case of using a base for hydrolysis in the process b, the carboxylic acid compound represented by Formula (V) may be obtained by subjecting the aqueous phase to acid precipitation, followed by filtration. The isolated carboxylic acid compound may be optionally purified by an operation such as recrystallization and column chromatography.

Then, the process c will be described.

The process c is, as shown in the following reaction scheme, a process of obtaining the carboxylic acid derivative reproducing compound represented by Formula (IIIa) by halogenating or esterifying the carboxylic acid compound represented by Formula (V), which is obtained together with the aromatic amide derivative represented by Formula (I) in the hydrolysis of the imide compound represented by Formula (IV).

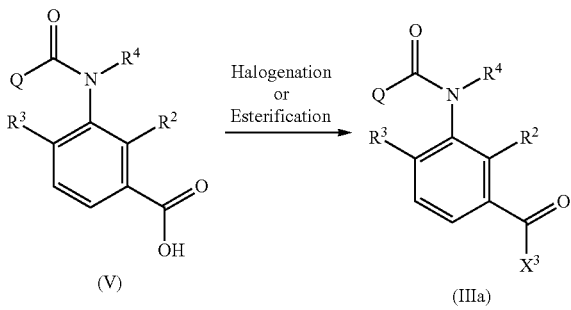

The halogenation in the above reaction is a reaction of obtaining the carboxylic acid derivative reproducing compound represented by Formula (IIIa) from the carboxylic acid compound represented by Formula (V) using a halogenating agent, and the esterification is a reaction of obtaining the carboxylic acid derivative reproducing compound represented by Formula (IIIa) from the carboxylic acid compound represented by Formula (V) using an acid catalyst in the presence of an alcohol.

The halogenating agent used in the above halogenation reaction includes phosgene, triphosgene, thionyl chloride, oxalyl chloride, phosphorus trichloride, phosphorus pentachloride, phosphorus oxychloride, phosphorus tribromide, and the like, and thionyl chloride, oxalyl chloride, and phosphorus oxychloride are preferable.

The amount of the halogenating agent used is, for example, in the range of from 0.2-fold molar equivalents to 10-fold molar equivalents, preferably in the range of from 0.5-fold molar equivalents to 2-fold molar equivalents, with respect to the amount of the carboxylic acid compound represented by Formula (V) used. The halogenating agent may be used in an amount appropriately selected within the above range.

Examples of the acid catalyst used for the esterification reaction are sulfuric acid, hydrochloric acid, p-toluenesulfonic acid, and the like, and sulfuric acid and p-toluenesulfonic acid are preferable.

The amount of the acid catalyst used is, for example, in the range of from 0.01-fold molar equivalents to 10-fold molar equivalents, preferably in the range of from 0.2-fold molar equivalents to 2-fold molar equivalents, with respect to the amount of the carboxylic acid compound represented by Formula (V) used. The acid catalyst may be used in an amount appropriately selected within the above range.

The above halogenation reaction and esterification reaction may be carried out in the absence of a solvent or may be carried out in the presence of an inert solvent.

The inert solvent is not particularly limited as long as the solvent does not significantly inhibit the progress of the reaction. Examples of the inert solvent may include aromatic hydrocarbons such as benzene, toluene and xylene; halogenated hydrocarbons such as dichloromethane, chloroform and carbon tetrachloride; N,N-dimethylformamide; and 1,3-dimethyl-2-imidazolidinon. These solvents may be used alone or as a mixture of two or more kinds thereof.

Among them, at least one member as an inert solvent selected from the group consisting of toluene and xylene can be particularly preferably used.

Concerning the amount of the inert solvent used, such a solvent may be used in an amount within the range of from 1-fold by mass to 15-fold by mass, and preferably within the range of from 1-fold by mass to 10-fold by mass, with respect to the amount of the carboxylic acid compound represented by Formula (V) used. The inert solvent may be used in an amount appropriately selected within the above range.

The reaction temperature in the above halogenation reaction and esterification reaction may be within the range of from −20° C. to 200° C., preferably within the range of from 20° C. to 120° C., and in the case of using an inert solvent, the reaction temperature may be any temperature that is lower than or equal to the boiling point. The reaction time may be appropriately selected within the range of from several minutes to 96 hours, and preferably within the range of from 30 minutes to 24 hours.

The above explained reaction conditions in the process c, such as type and amount of the halogenating agent, the acid catalyst, and the inert solvent, reaction temperature and reaction time of the halogenation reaction and esterification reaction, or the like are combinable in any arbitrary level, and each and every such combination is explicitly disclosed herein, as if each and every aspect was individually and explicitly recited.

In the process c as described above, the carboxylic acid derivative reproducing compound represented by Formula (IIIa), which is the aimed product, may be used in the process d with or without purification after completion of the reaction.

Then, the process d will be described.

The process d is a process of obtaining the imide compound represented by Formula (IV) by reacting the carboxylic acid derivative reproducing compound represented by Formula (IIIa) obtained in the process c and the aniline derivative represented by Formula (II) in the presence of a base.

In the process d, the imide compound represented by Formula (IV) is obtained by allowing to perform the reaction between the carboxylic acid derivative reproducing compound represented by Formula (IIIa) in place of the carboxylic acid derivative represented by Formula (III) and the aniline derivative represented by Formula (II), or between the carboxylic acid derivative reproducing compound represented by Formula (IIIa) together with the carboxylic acid derivative represented by Formula (III) and the aniline derivative represented by Formula (II), in the presence of a base in the same manner as in the process a.

The reaction conditions in the process d (type and amount of bases, reaction, type and amount used of inert solvents, reaction temperature, reaction time, etc.) are the same as those in the process a. However, the reaction conditions in the process d may be different from those in the process a.

In the case of using the carboxylic acid derivative reproducing compound represented by Formula (IIIa) together with the carboxylic acid derivative represented by Formula (III) in the process d, the amount of the carboxylic acid derivatives reproducing compound represented by Formula (IIIa) used may be from 1% by mass to 100% by mass, and is preferably from 1% by mass to 90% by mass, with respect to the total amount of the carboxylic acid derivative represented by Formula (III) and the carboxylic acid derivative reproducing compound represented by Formula (IIIa) used.

Then, the process e will be described.

The process e is a process of obtaining the aromatic amide derivative represented by Formula (I) in the same manner as in the process b, by hydrolyzing the imide compound represented by Formula (IV) obtained in the process d.

The reaction conditions in the process e (type and amount of bases or acids used in the hydrolysis, reaction, type and amount used of inert solvents, reaction temperature, reaction time, etc.) are the same as those in the process b. However, the reaction conditions in the process e may be different from those in the process b.

The aromatic amide derivative represented by Formula (I) obtained in the process e may be isolated in the same manner as in the process b from the reaction system after the completion of the reaction, according to a conventional method, and, if necessary, purification may be carried out by an operation such as recrystallization, column chromatography, or distillation.

In the process e, the carboxylic acid compound represented by Formula (V) is obtained together with the aromatic amide derivative represented by Formula (I) by hydrolyzing the imide compound represented by Formula (IV).

As with the process b, in the case of using an acid for hydrolysis, the carboxylic acid compound represented by Formula (V) may be isolated by filtration after the completion of the reaction. In the case of using a base for hydrolysis, the carboxylic acid compound represented by Formula (V) may be isolated by subjecting the aqueous phase to acid precipitation, followed by filtration. The isolated carboxylic acid compound may be optionally purified by an operation such as recrystallization and column chromatography.

The carboxylic acid compound represented by Formula (V) obtained in the process e can be used as a raw material for the reaction in the process c. That is, the reactions of from the process c to the process e may be repeated by using the carboxylic acid compound represented by Formula (V) as a raw material and using the resulting carboxylic acid derivative reproducing compound represented by Formula (IIIa) as a raw material for the reaction with the aniline derivative represented by Formula (II) in the process d.

The number of repeated reactions is not particularly limited and may be appropriately determined to be, for example, within a range of from one time to 1000 times, preferably within a range of from one time to 500 times, in consideration of the type and amount of by-products accumulated in the repeated reaction system, the reaction yield of each reaction process, the quality of the resulting aromatic amide derivative represented by Formula (I), and the like.

Each process through process a to process e is combinable in any arbitrary level within the reaction conditions explained above, and each and every such combination is explicitly disclosed herein, as if each and every aspect was individually and explicitly recited.

Typical compounds of the imide compound represented by Formula (IV), which are effective intermediates of the invention, will be exemplified below. However the invention is not limited to these compounds.

Incidentally, in the exemplified compounds shown below, "Me" represents a methyl group, "Et" represents an ethyl group, "Pr" represents a propyl group, "H" represents a hydrogen atom, "F" represents a fluorine atom, "Cl" represents a chlorine atom, "Br" represents a bromine atom, "I" represents an iodine atom, and "$CF_3$" represents a trifluoromethyl group, respectively.

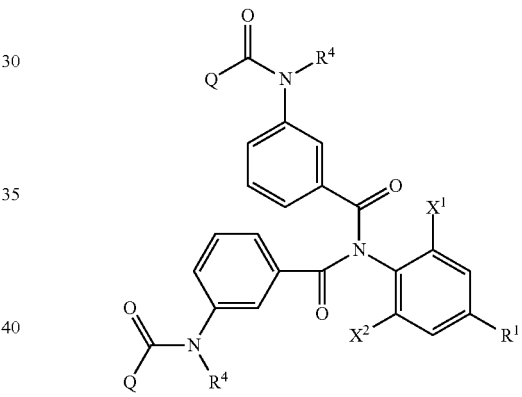

TABLE 1

| Compound No. | $R^1$ | $X^1$ | $X^2$ | $R^4$ | Q |
|---|---|---|---|---|---|
| 1-001 | heptafluoroisopropyl | Br | Me | H | phenyl |
| 1-002 | heptafluoroisopropyl | I | Me | H | phenyl |
| 1-003 | heptafluoroisopropyl | Br | Me | Me | phenyl |
| 1-004 | heptafluoroisopropyl | I | Me | Me | phenyl |
| 1-005 | heptafluoroisopropyl | Br | Me | H | 4-fluorophenyl |
| 1-006 | heptafluoroisopropyl | I | Me | H | 4-fluorophenyl |
| 1-007 | heptafluoroisopropyl | Br | Me | Me | 4-fluorophenyl |
| 1-008 | heptafluoroisopropyl | I | Me | Me | 4-fluorophenyl |
| 1-009 | heptafluoroisopropyl | Br | Me | H | 6-(trifluoromethyl)pyridin-3-yl |
| 1-010 | heptafluoroisopropyl | I | Me | H | 6-(trifluoromethyl)pyridin-3-yl |
| 1-011 | heptafluoroisopropyl | Br | Me | Me | 6-(trifluoromethyl)pyridin-3-yl |
| 1-012 | heptafluoroisopropyl | I | Me | Me | 6-(trifluoromethyl)pyridin-3-yl |
| 1-013 | heptafluoroisopropyl | Br | $CF_3$ | H | phenyl |
| 1-014 | heptafluoroisopropyl | I | $CF_3$ | H | phenyl |
| 1-015 | heptafluoroisopropyl | Br | $CF_3$ | Me | phenyl |
| 1-016 | heptafluoroisopropyl | I | $CF_3$ | Me | phenyl |
| 1-017 | heptafluoroisopropyl | Br | $CF_3$ | H | 4-fluorophenyl |
| 1-018 | heptafluoroisopropyl | I | $CF_3$ | H | 4-fluorophenyl |
| 1-019 | heptafluoroisopropyl | Br | $CF_3$ | Me | 4-fluorophenyl |
| 1-020 | heptafluoroisopropyl | I | $CF_3$ | Me | 4-fluorophenyl |
| 1-021 | heptafluoroisopropyl | Br | $CF_3$ | H | 6-(trifluoromethyl)pyridin-3-yl |

TABLE 1-continued

| Compound No. | R¹ | X¹ | X² | R⁴ | Q |
|---|---|---|---|---|---|
| 1-022 | heptafluoroisopropyl | I | CF₃ | H | 6-(trifluoromethyl)pyridin-3-yl |
| 1-023 | heptafluoroisopropyl | Br | CF₃ | Me | 6-(trifluoromethyl)pyridin-3-yl |
| 1-024 | heptafluoroisopropyl | I | CF₃ | Me | 6-(trifluoromethyl)pyridin-3-yl |
| 1-025 | heptafluoroisopropyl | Me | Me | Me | phenyl |
| 1-026 | heptafluoroisopropyl | Me | Me | Me | 4-fluorophenyl |
| 1-027 | heptafluoroisopropyl | Me | Me | Me | 6-(trifluoromethyl)pyridin-3-yl |
| 1-028 | heptafluoroisopropyl | Me | Me | Me | 4-cyanophenyl |
| 1-029 | nonafluoro-s-butyl | Br | Me | H | phenyl |
| 1-030 | nonafluoro-s-butyl | I | Me | H | phenyl |
| 1-031 | nonafluoro-s-butyl | Br | Me | Me | phenyl |
| 1-032 | nonafluoro-s-butyl | I | Me | Me | phenyl |
| 1-033 | nonafluoro-s-butyl | Br | Me | H | 4-fluorophenyl |
| 1-034 | nonafluoro-s-butyl | I | Me | H | 4-fluorophenyl |
| 1-035 | nonafluoro-s-butyl | Br | Me | Me | 4-fluorophenyl |
| 1-036 | nonafluoro-s-butyl | I | Me | Me | 4-fluorophenyl |
| 1-037 | nonafluoro-s-butyl | Br | Me | H | 6-(trifluoromethyl)pyridin-3-yl |
| 1-038 | nonafluoro-s-butyl | I | Me | H | 6-(trifluoromethyl)pyridin-3-yl |
| 1-039 | nonafluoro-s-butyl | Br | Me | Me | 6-(trifluoromethyl)pyridin-3-yl |
| 1-040 | nonafluoro-s-butyl | I | Me | Me | 6-(trifluoromethyl)pyridin-3-yl |

TABLE 2

| Compound No. | R¹ | X¹ | X² | R⁴ | Q |
|---|---|---|---|---|---|
| 1-041 | nonafluoro-s-butyl | Br | CF₃ | H | phenyl |
| 1-042 | nonafluoro-s-butyl | I | CF₃ | H | phenyl |
| 1-043 | nonafluoro-s-butyl | Br | CF₃ | Me | phenyl |
| 1-044 | nonafluoro-s-butyl | I | CF₃ | Me | phenyl |
| 1-045 | nonafluoro-s-butyl | Br | CF₃ | H | 4-fluorophenyl |
| 1-046 | nonafluoro-s-butyl | I | CF₃ | H | 4-fluorophenyl |
| 1-047 | nonafluoro-s-butyl | Br | CF₃ | Me | 4-fluorophenyl |
| 1-048 | nonafluoro-s-butyl | I | CF₃ | Me | 4-fluorophenyl |
| 1-049 | nonafluoro-s-butyl | Br | CF₃ | H | 6-(trifluoromethyl)pyridin-3-yl |
| 1-050 | nonafluoro-s-butyl | I | CF₃ | H | 6-(trifluoromethyl)pyridin-3-yl |
| 1-051 | nonafluoro-s-butyl | Br | CF₃ | Me | 6-(trifluoromethyl)pyridin-3-yl |
| 1-052 | nonafluoro-s-butyl | I | CF₃ | Me | 6-(trifluoromethyl)pyridin-3-yl |
| 1-053 | heptafluoroisopropyl | Cl | Br | Me | phenyl |
| 1-054 | heptafluoroisopropyl | Cl | Br | Me | 4-pyridyl |
| 1-055 | heptafluoroisopropyl | Cl | Br | Me | 3-pyridyl |
| 1-056 | heptafluoroisopropyl | Cl | Br | Me | 2-pyridyl |
| 1-057 | heptafluoroisopropyl | Cl | Br | Me | 4-cyanophenyl |
| 1-058 | heptafluoroisopropyl | Cl | Br | Et | phenyl |
| 1-059 | heptafluoroisopropyl | Cl | Br | Et | 4-pyridyl |
| 1-060 | heptafluoroisopropyl | Cl | Br | Et | 3-pyridyl |
| 1-061 | heptafluoroisopropyl | Cl | Br | Et | 2-pyridyl |
| 1-062 | heptafluoroisopropyl | Cl | Br | Me | 4-cyanophenyl |
| 1-063 | heptafluoroisopropyl | Et | Br | Me | phenyl |
| 1-064 | heptafluoroisopropyl | Et | Br | Me | 4-pyridyl |
| 1-065 | heptafluoroisopropyl | Et | Br | Me | 3-pyridyl |
| 1-066 | heptafluoroisopropyl | Et | Br | Me | 2-pyridyl |
| 1-067 | heptafluoroisopropyl | Cl | Br | Me | 4-cyanophenyl |
| 1-068 | heptafluoroisopropyl | Et | Br | Et | phenyl |
| 1-069 | heptafluoroisopropyl | Et | Br | Et | 4-pyridyl |
| 1-070 | heptafluoroisopropyl | Et | Br | Et | 3-pyridyl |
| 1-071 | heptafluoroisopropyl | Et | Br | Et | 2-pyridyl |
| 1-072 | heptafluoroisopropyl | Cl | Br | Me | 4-cyanophenyl |
| 1-073 | heptafluoroisopropyl | Br | Br | Me | phenyl |
| 1-074 | heptafluoroisopropyl | Br | Br | Me | 4-pyridyl |
| 1-075 | heptafluoroisopropyl | Br | Br | Me | 3-pyridyl |
| 1-076 | heptafluoroisopropyl | Br | Br | Me | 2-pyridyl |
| 1-077 | heptafluoroisopropyl | Br | Br | Me | 4-cyanophenyl |
| 1-078 | heptafluoroisopropyl | Br | Br | Et | phenyl |
| 1-079 | heptafluoroisopropyl | Br | Br | Et | 4-pyridyl |
| 1-080 | heptafluoroisopropyl | Br | Br | Et | 3-pyridyl |

TABLE 3

| Compound No. | R¹ | X¹ | X² | R⁴ | Q |
|---|---|---|---|---|---|
| 1-081 | heptafluoroisopropyl | Br | Br | Et | 2-pyridyl |
| 1-082 | heptafluoroisopropyl | Br | Br | Me | 4-cyanophenyl |
| 1-083 | heptafluoroisopropyl | Br | Br | Me | phenyl |
| 1-084 | heptafluoroisopropyl | Br | Br | Me | 4-pyridyl |
| 1-085 | heptafluoroisopropyl | Br | Br | Me | 3-pyridyl |
| 1-086 | heptafluoroisopropyl | Br | Br | Me | 2-pyridyl |
| 1-087 | heptafluoroisopropyl | Br | Br | Me | 4-cyanophenyl |
| 1-088 | heptafluoroisopropyl | Br | Br | Et | phenyl |
| 1-089 | heptafluoroisopropyl | Br | Br | Et | 4-pyridyl |
| 1-090 | heptafluoroisopropyl | Br | Br | Et | 3-pyridyl |
| 1-091 | heptafluoroisopropyl | Br | Br | Et | 2-pyridyl |
| 1-092 | heptafluoroisopropyl | Br | Br | Me | 4-cyanophenyl |
| 1-093 | heptafluoroisopropyl | Br | Br | H | N-ethyl-N-methylaminocarbonyl |
| 1-094 | heptafluoroisopropyl | Br | Br | Me | N-ethyl-N-methylaminocarbonyl |
| 1-095 | heptafluoroisopropyl | Br | difluoromethoxy | H | N-ethyl-N-methylaminocarbonyl |
| 1-096 | heptafluoroisopropyl | Br | difluoromethoxy | Me | N-ethyl-N-methylaminocarbonyl |
| 1-097 | heptafluoroisopropyl | Me | difluoromethoxy | H | N-ethyl-N-methylaminocarbonyl |
| 1-098 | heptafluoroisopropyl | Me | difluoromethoxy | Me | N-ethyl-N-methylaminocarbonyl |
| 1-099 | heptafluoroisopropyl | Me | Et | H | N-ethyl-N-methylaminocarbonyl |
| 1-100 | heptafluoroisopropyl | Me | Et | Me | N-ethyl-N-methylaminocarbonyl |
| 1-101 | heptafluoroisopropyl | Br | Br | H | N-(2,2,2-trifluoroethyl)-N-methylaminocarbonyl |
| 1-102 | heptafluoroisopropyl | Br | Br | Me | N-(2,2,2-trifluoroethyl)-N-methylaminocarbonyl |
| 1-103 | heptafluoroisopropyl | Br | difluoromethoxy | H | N-(2,2,2-trifluoroethyl)-N-methylaminocarbonyl |
| 1-104 | heptafluoroisopropyl | Br | difluoromethoxy | Me | N-(2,2,2-trifluoroethyl)-N-methylaminocarbonyl |
| 1-105 | heptafluoroisopropyl | Me | difluoromethoxy | H | N-(2,2,2-trifluoroethyl)-N-methylaminocarbonyl |
| 1-106 | heptafluoroisopropyl | Me | difluoromethoxy | Me | N-(2,2,2-trifluoroethyl)-N-methylaminocarbonyl |
| 1-107 | heptafluoroisopropyl | Me | Et | H | N-(2,2,2-trifluoroethyl)-N-methylaminocarbonyl |
| 1-108 | heptafluoroisopropyl | Me | Et | Me | N-(2,2,2-trifluoroethyl)-N-methylaminocarbonyl |

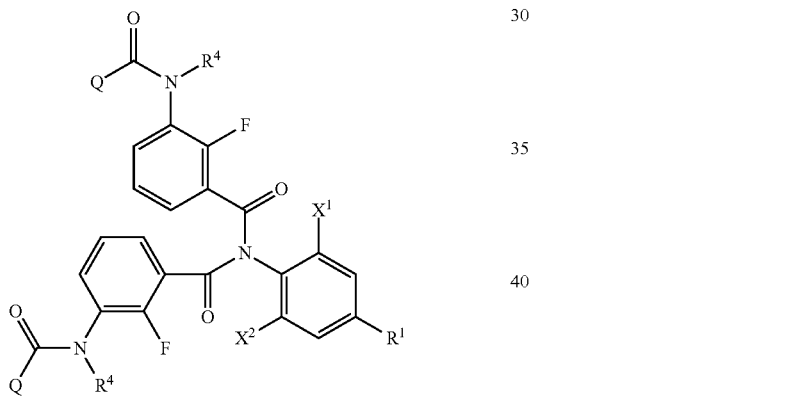

TABLE 4

| Compound No. | R¹ | X¹ | X² | R⁴ | Q |
|---|---|---|---|---|---|
| 1-109 | heptafluoroisopropyl | Br | Me | H | phenyl |
| 1-110 | heptafluoroisopropyl | I | Me | H | phenyl |
| 1-111 | heptafluoroisopropyl | Br | Me | Me | phenyl |
| 1-112 | heptafluoroisopropyl | I | Me | Me | phenyl |
| 1-113 | heptafluoroisopropyl | Br | Me | H | 4-fluorophenyl |
| 1-114 | heptafluoroisopropyl | I | Me | H | 4-fluorophenyl |
| 1-115 | heptafluoroisopropyl | Br | Me | Me | 4-fluorophenyl |
| 1-116 | heptafluoroisopropyl | I | Me | Me | 4-fluorophenyl |
| 1-117 | heptafluoroisopropyl | Br | Me | H | 6-(trifluoromethyl)pyridin-3-yl |
| 1-118 | heptafluoroisopropyl | I | Me | H | 6-(trifluoromethyl)pyridin-3-yl |
| 1-119 | heptafluoroisopropyl | Br | Me | Me | 6-(trifluoromethyl)pyridin-3-yl |
| 1-120 | heptafluoroisopropyl | I | Me | Me | 6-(trifluoromethyl)pyridin-3-yl |
| 1-121 | heptafluoroisopropyl | Br | CF₃ | H | phenyl |
| 1-122 | heptafluoroisopropyl | I | CF₃ | H | phenyl |
| 1-123 | heptafluoroisopropyl | Br | CF₃ | Me | phenyl |
| 1-124 | heptafluoroisopropyl | I | CF₃ | Me | phenyl |
| 1-125 | heptafluoroisopropyl | Br | CF₃ | H | 4-fluorophenyl |
| 1-126 | heptafluoroisopropyl | I | CF₃ | H | 4-fluorophenyl |
| 1-127 | heptafluoroisopropyl | Br | CF₃ | Me | 4-fluorophenyl |

TABLE 4-continued

| Compound No. | R¹ | X¹ | X² | R⁴ | Q |
|---|---|---|---|---|---|
| 1-128 | heptafluoroisopropyl | I | CF₃ | Me | 4-fluorophenyl |
| 1-129 | heptafluoroisopropyl | Br | CF₃ | H | 6-(trifluoromethyl)pyridin-3-yl |
| 1-130 | heptafluoroisopropyl | I | CF₃ | H | 6-(trifluoromethyl)pyridin-3-yl |
| 1-131 | heptafluoroisopropyl | Br | CF₃ | Me | 6-(trifluoromethyl)pyridin-3-yl |
| 1-132 | heptafluoroisopropyl | I | CF₃ | Me | 6-(trifluoromethyl)pyridin-3-yl |
| 1-133 | heptafluoroisopropyl | Br | CF₃ | H | 2,6-difluorophenyl |
| 1-134 | heptafluoroisopropyl | I | CF₃ | H | 2,6-difluorophenyl |
| 1-135 | heptafluoroisopropyl | Br | CF₃ | Me | 2,6-difluorophenyl |
| 1-136 | heptafluoroisopropyl | I | CF₃ | Me | 2,6-difluorophenyl |
| 1-137 | heptafluoroisopropyl | Me | Me | Me | phenyl |
| 1-138 | heptafluoroisopropyl | Me | Me | Me | 4-fluorophenyl |
| 1-139 | heptafluoroisopropyl | Me | Me | Me | 6-(trifluoromethyl)pyridin-3-yl |
| 1-140 | heptafluoroisopropyl | Me | Me | Me | 4-cyanophenyl |
| 1-141 | nonafluoro-s-butyl | Br | Me | H | phenyl |
| 1-142 | nonafluoro-s-butyl | I | Me | H | phenyl |
| 1-143 | nonafluoro-s-butyl | Br | Me | Me | phenyl |
| 1-144 | nonafluoro-s-butyl | I | Me | Me | phenyl |
| 1-145 | nonafluoro-s-butyl | Br | Me | H | 4-fluorophenyl |
| 1-146 | nonafluoro-s-butyl | I | Me | H | 4-fluorophenyl |
| 1-147 | nonafluoro-s-butyl | Br | Me | Me | 4-fluorophenyl |
| 1-148 | nonafluoro-s-butyl | I | Me | Me | 4-fluorophenyl |
| 1-149 | nonafluoro-s-butyl | Br | Me | H | 6-(trifluoromethyl)pyridin-3-yl |
| 1-150 | nonafluoro-s-butyl | I | Me | H | 6-(trifluoromethyl)pyridin-3-yl |

TABLE 5

| Compound No. | R¹ | X¹ | X² | R⁴ | Q |
|---|---|---|---|---|---|
| 1-151 | nonafluoro-s-butyl | Br | Me | Me | 6-(trifluoromethyl)pyridin-3-yl |
| 1-152 | nonafluoro-s-butyl | I | Me | Me | 6-(trifluoromethyl)pyridin-3-yl |
| 1-153 | nonafluoro-s-butyl | Br | CF₃ | H | phenyl |
| 1-154 | nonafluoro-s-butyl | I | CF₃ | H | phenyl |
| 1-155 | nonafluoro-s-butyl | Br | CF₃ | Me | phenyl |
| 1-156 | nonafluoro-s-butyl | I | CF₃ | Me | phenyl |
| 1-157 | nonafluoro-s-butyl | Br | CF₃ | H | 4-fluorophenyl |
| 1-158 | nonafluoro-s-butyl | I | CF₃ | H | 4-fluorophenyl |
| 1-159 | nonafluoro-s-butyl | Br | CF₃ | Me | 4-fluorophenyl |
| 1-160 | nonafluoro-s-butyl | I | CF₃ | Me | 4-fluorophenyl |
| 1-161 | nonafluoro-s-butyl | Br | CF₃ | H | 6-(trifluoromethyl)pyridin-3-yl |
| 1-162 | nonafluoro-s-butyl | I | CF₃ | H | 6-(trifluoromethyl)pyridin-3-yl |
| 1-163 | nonafluoro-s-butyl | Br | CF₃ | Me | 6-(trifluoromethyl)pyridin-3-yl |
| 1-164 | nonafluoro-s-butyl | I | CF₃ | Me | 6-(trifluoromethyl)pyridin-3-yl |
| 1-165 | nonafluoro-s-butyl | Cl | Cl | H | phenyl |
| 1-166 | nonafluoro-s-butyl | Cl | Cl | Me | phenyl |
| 1-167 | nonafluoro-s-butyl | Br | Br | H | phenyl |
| 1-168 | nonafluoro-s-butyl | Br | Br | Me | phenyl |
| 1-169 | nonafluoro-s-butyl | I | I | H | phenyl |
| 1-170 | nonafluoro-s-butyl | I | I | Me | phenyl |
| 1-171 | nonafluoro-s-butyl | Cl | Cl | H | 4-fluorophenyl |
| 1-172 | nonafluoro-s-butyl | Cl | Cl | Me | 4-fluorophenyl |
| 1-173 | nonafluoro-s-butyl | Br | Br | H | 4-fluorophenyl |
| 1-174 | nonafluoro-s-butyl | Br | Br | Me | 4-fluorophenyl |
| 1-175 | nonafluoro-s-butyl | I | I | H | 4-fluorophenyl |
| 1-176 | nonafluoro-s-butyl | I | I | Me | 4-fluorophenyl |
| 1-177 | nonafluoro-s-butyl | Cl | Cl | H | 6-(trifluoromethyl)pyridin-3-yl |
| 1-178 | nonafluoro-s-butyl | Cl | Cl | Me | 6-(trifluoromethyl)pyridin-3-yl |
| 1-179 | nonafluoro-s-butyl | Br | Br | H | 6-(trifluoromethyl)pyridin-3-yl |
| 1-180 | nonafluoro-s-butyl | Br | Br | Me | 6-(trifluoromethyl)pyridin-3-yl |
| 1-181 | nonafluoro-s-butyl | I | I | H | 6-(trifluoromethyl)pyridin-3-yl |
| 1-182 | nonafluoro-s-butyl | I | I | Me | 6-(trifluoromethyl)pyridin-3-yl |
| 1-183 | heptafluoroisopropyl | Cl | Br | Me | phenyl |
| 1-184 | heptafluoroisopropyl | Cl | Br | Me | 4-pyridyl |
| 1-185 | heptafluoroisopropyl | Cl | Br | Me | 3-pyridyl |
| 1-186 | heptafluoroisopropyl | Cl | Br | Me | 2-pyridyl |
| 1-187 | heptafluoroisopropyl | Cl | Br | Me | 4-cyanophenyl |
| 1-188 | heptafluoroisopropyl | Cl | Br | Et | phenyl |
| 1-189 | heptafluoroisopropyl | Cl | Br | Et | 4-pyridyl |
| 1-190 | heptafluoroisopropyl | Cl | Br | Et | 3-pyridyl |

TABLE 6

| Compound No. | R¹ | X¹ | X² | R⁴ | Q |
|---|---|---|---|---|---|
| 1-191 | heptafluoroisopropyl | Cl | Br | Et | 2-pyridyl |
| 1-192 | heptafluoroisopropyl | Cl | Br | Me | 4-cyanophenyl |
| 1-193 | heptafluoroisopropyl | Et | Br | Me | phenyl |
| 1-194 | heptafluoroisopropyl | Et | Br | Me | 4-pyridyl |
| 1-195 | heptafluoroisopropyl | Et | Br | Me | 3-pyridyl |
| 1-196 | heptafluoroisopropyl | Et | Br | Me | 2-pyridyl |
| 1-197 | heptafluoroisopropyl | Cl | Br | Me | 4-cyanophenyl |
| 1-198 | heptafluoroisopropyl | Et | Br | Et | phenyl |
| 1-199 | heptafluoroisopropyl | Et | Br | Et | 4-pyridyl |
| 1-200 | heptafluoroisopropyl | Et | Br | Et | 3-pyridyl |
| 1-201 | heptafluoroisopropyl | Et | Br | Et | 2-pyridyl |
| 1-202 | heptafluoroisopropyl | Cl | Br | Me | 4-cyanophenyl |
| 1-203 | heptafluoroisopropyl | Br | Br | Me | phenyl |
| 1-204 | heptafluoroisopropyl | Br | Br | Me | 4-pyridyl |
| 1-205 | heptafluoroisopropyl | Br | Br | Me | 3-pyridyl |
| 1-206 | heptafluoroisopropyl | Br | Br | Me | 2-pyridyl |
| 1-207 | heptafluoroisopropyl | Br | Br | Me | 4-cyanophenyl |
| 1-208 | heptafluoroisopropyl | Br | Br | Et | phenyl |
| 1-209 | heptafluoroisopropyl | Br | Br | Et | 4-pyridyl |
| 1-210 | heptafluoroisopropyl | Br | Br | Et | 3-pyridyl |
| 1-211 | heptafluoroisopropyl | Br | Br | Et | 2-pyridyl |
| 1-212 | heptafluoroisopropyl | Br | Br | Me | 4-cyanophenyl |
| 1-213 | heptafluoroisopropyl | Br | Br | Me | phenyl |
| 1-214 | heptafluoroisopropyl | Br | Br | Me | 4-pyridyl |
| 1-215 | heptafluoroisopropyl | Br | Br | Me | 3-pyridyl |
| 1-216 | heptafluoroisopropyl | Br | Br | Me | 2-pyridyl |
| 1-217 | heptafluoroisopropyl | Br | Br | Me | 4-cyanophenyl |
| 1-218 | heptafluoroisopropyl | Br | Br | Et | phenyl |
| 1-219 | heptafluoroisopropyl | Br | Br | Et | 4-pyridyl |
| 1-220 | heptafluoroisopropyl | Br | Br | Et | 3-pyridyl |
| 1-221 | heptafluoroisopropyl | Br | Br | Et | 2-pyridyl |
| 1-222 | heptafluoroisopropyl | Br | Br | Me | 4-cyanophenyl |
| 1-223 | heptafluoroisopropyl | Br | Br | H | N-ethyl-N-methylaminocarbonyl |
| 1-224 | heptafluoroisopropyl | Br | Br | Me | N-ethyl-N-methylaminocarbonyl |
| 1-225 | heptafluoroisopropyl | Br | difluoromethoxy | H | N-ethyl-N-methylaminocarbonyl |
| 1-226 | heptafluoroisopropyl | Br | difluoromethoxy | Me | N-ethyl-N-methylaminocarbonyl |
| 1-227 | heptafluoroisopropyl | Me | difluoromethoxy | H | N-ethyl-N-methylaminocarbonyl |
| 1-228 | heptafluoroisopropyl | Me | difluoromethoxy | Me | N-ethyl-N-methylaminocarbonyl |
| 1-229 | heptafluoroisopropyl | Me | Et | H | N-ethyl-N-methylaminocarbonyl |
| 1-230 | heptafluoroisopropyl | Me | Et | Me | N-ethyl-N-methylaminocarbonyl |

TABLE 7

| Compound No. | R¹ | X¹ | X² | R⁴ | Q |
|---|---|---|---|---|---|
| 1-231 | heptafluoroisopropyl | Br | Br | H | N-(2,2,2-trifluoroethyl)-N-methylaminocarbonyl |
| 1-232 | heptafluoroisopropyl | Br | Br | Me | N-(2,2,2-trifluoroethyl)-N-methylaminocarbonyl |
| 1-233 | heptafluoroisopropyl | Br | difluoromethoxy | H | N-(2,2,2-trifluoroethyl)-N-methylaminocarbonyl |
| 1-234 | heptafluoroisopropyl | Br | difluoromethoxy | Me | N-(2,2,2-trifluoroethyl)-N-methylaminocarbonyl |
| 1-235 | heptafluoroisopropyl | Me | difluoromethoxy | H | N-(2,2,2-trifluoroethyl)-N-methylaminocarbonyl |
| 1-236 | heptafluoroisopropyl | Me | difluoromethoxy | Me | N-(2,2,2-trifluoroethyl)-N-methylaminocarbonyl |
| 1-237 | heptafluoroisopropyl | Me | Et | H | N-(2,2,2-trifluoroethyl)-N-methylaminocarbonyl |
| 1-238 | heptafluoroisopropyl | Me | Et | Me | N-(2,2,2-trifluoroethyl)-N-methylaminocarbonyl |
| 1-239 | Br | heptafluoroisopropyl | CF₃ | H | phenyl |
| 1-240 | Br | heptafluoroisopropyl | CF₃ | Me | phenyl |
| 1-241 | Br | heptafluoroisopropyl | CF₃ | H | 4-fluorophenyl |
| 1-242 | Br | heptafluoroisopropyl | CF₃ | Me | 4-fluorophenyl |
| 1-243 | Br | heptafluoroisopropyl | CF₃ | H | 6-(trifluoromethyl)pyridin-3-yl |
| 1-244 | Br | heptafluoroisopropyl | CF₃ | Me | 6-(trifluoromethyl)pyridin-3-yl |
| 1-245 | heptafluoroisopropyl | heptafluoroisopropyl | CF₃ | H | phenyl |
| 1-246 | heptafluoroisopropyl | heptafluoroisopropyl | CF₃ | Me | phenyl |
| 1-247 | heptafluoroisopropyl | heptafluoroisopropyl | CF₃ | H | 4-fluorophenyl |
| 1-248 | heptafluoroisopropyl | heptafluoroisopropyl | CF₃ | Me | 4-fluorophenyl |
| 1-249 | heptafluoroisopropyl | heptafluoroisopropyl | CF₃ | H | 6-(trifluoromethyl)pyridin-3-yl |
| 1-250 | heptafluoroisopropyl | heptafluoroisopropyl | CF₃ | Me | 6-(trifluoromethyl)pyridin-3-yl |

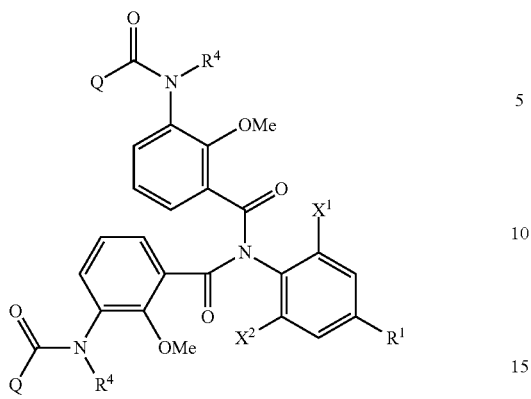

TABLE 8

| Compound No. | R¹ | X¹ | X² | R⁴ | Q |
|---|---|---|---|---|---|
| 1-251 | heptafluoroisopropyl | Br | Me | H | phenyl |
| 1-252 | heptafluoroisopropyl | I | Me | H | phenyl |
| 1-253 | heptafluoroisopropyl | Br | Me | Me | phenyl |
| 1-254 | heptafluoroisopropyl | I | Me | Me | phenyl |
| 1-255 | heptafluoroisopropyl | Br | Me | H | 4-fluorophenyl |
| 1-256 | heptafluoroisopropyl | I | Me | H | 4-fluorophenyl |
| 1-257 | heptafluoroisopropyl | Br | Me | Me | 4-fluorophenyl |
| 1-258 | heptafluoroisopropyl | I | Me | Me | 4-fluorophenyl |
| 1-259 | heptafluoroisopropyl | Br | Me | H | 6-(trifluoromethyl)pyridin-3-yl |
| 1-260 | heptafluoroisopropyl | I | Me | H | 6-(trifluoromethyl)pyridin-3-yl |
| 1-261 | heptafluoroisopropyl | Br | Me | Me | 6-(trifluoromethyl)pyridin-3-yl |
| 1-262 | heptafluoroisopropyl | I | Me | Me | 6-(trifluoromethyl)pyridin-3-yl |
| 1-263 | heptafluoroisopropyl | Br | CF₃ | H | phenyl |
| 1-264 | heptafluoroisopropyl | I | CF₃ | H | phenyl |
| 1-265 | heptafluoroisopropyl | Br | CF₃ | Me | phenyl |
| 1-266 | heptafluoroisopropyl | I | CF₃ | Me | phenyl |
| 1-267 | heptafluoroisopropyl | Br | CF₃ | H | 4-fluorophenyl |
| 1-268 | heptafluoroisopropyl | I | CF₃ | H | 4-fluorophenyl |
| 1-269 | heptafluoroisopropyl | Br | CF₃ | Me | 4-fluorophenyl |
| 1-270 | heptafluoroisopropyl | I | CF₃ | Me | 4-fluorophenyl |
| 1-271 | heptafluoroisopropyl | Br | CF₃ | H | 6-(trifluoromethyl)pyridin-3-yl |
| 1-272 | heptafluoroisopropyl | I | CF₃ | H | 6-(trifluoromethyl)pyridin-3-yl |
| 1-273 | heptafluoroisopropyl | Br | CF₃ | Me | 6-(trifluoromethyl)pyridin-3-yl |
| 1-274 | heptafluoroisopropyl | I | CF₃ | Me | 6-(trifluoromethyl)pyridin-3-yl |
| 1-275 | heptafluoroisopropyl | Me | Me | Me | phenyl |
| 1-276 | heptafluoroisopropyl | Me | Me | Me | 4-fluorophenyl |
| 1-277 | heptafluoroisopropyl | Me | Me | Me | 6-(trifluoromethyl)pyridin-3-yl |
| 1-278 | heptafluoroisopropyl | Me | Me | Me | 4-cyanophenyl |
| 1-279 | nonafluoro-s-butyl | Br | Me | H | phenyl |
| 1-280 | nonafluoro-s-butyl | I | Me | H | phenyl |
| 1-281 | nonafluoro-s-butyl | Br | Me | Me | phenyl |
| 1-282 | nonafluoro-s-butyl | I | Me | Me | phenyl |
| 1-283 | nonafluoro-s-butyl | Br | Me | H | 4-fluorophenyl |
| 1-284 | nonafluoro-s-butyl | I | Me | H | 4-fluorophenyl |
| 1-285 | nonafluoro-s-butyl | Br | Me | Me | 4-fluorophenyl |
| 1-286 | nonafluoro-s-butyl | I | Me | Me | 4-fluorophenyl |
| 1-287 | nonafluoro-s-butyl | Br | Me | H | 6-(trifluoromethyl)pyridin-3-yl |
| 1-288 | nonafluoro-s-butyl | I | Me | H | 6-(trifluoromethyl)pyridin-3-yl |
| 1-289 | nonafluoro-s-butyl | Br | Me | Me | 6-(trifluoromethyl)pyridin-3-yl |
| 1-290 | nonafluoro-s-butyl | I | Me | Me | 6-(trifluoromethyl)pyridin-3-yl |

TABLE 9

| Compound No. | R¹ | X¹ | X² | R⁴ | Q |
|---|---|---|---|---|---|
| 1-291 | nonafluoro-s-butyl | Br | CF₃ | H | phenyl |
| 1-292 | nonafluoro-s-butyl | I | CF₃ | H | phenyl |
| 1-293 | nonafluoro-s-butyl | Br | CF₃ | Me | phenyl |
| 1-294 | nonafluoro-s-butyl | I | CF₃ | Me | phenyl |
| 1-295 | nonafluoro-s-butyl | Br | CF₃ | H | 4-fluorophenyl |
| 1-296 | nonafluoro-s-butyl | I | CF₃ | H | 4-fluorophenyl |

TABLE 9-continued

| Compound No. | R¹ | X¹ | X² | R⁴ | Q |
|---|---|---|---|---|---|
| 1-297 | nonafluoro-s-butyl | Br | CF₃ | Me | 4-fluorophenyl |
| 1-298 | nonafluoro-s-butyl | I | CF₃ | Me | 4-fluorophenyl |
| 1-299 | nonafluoro-s-butyl | Br | CF₃ | H | 6-(trifluoromethyl)pyridin-3-yl |
| 1-300 | nonafluoro-s-butyl | I | CF₃ | H | 6-(trifluoromethyl)pyridin-3-yl |
| 1-301 | nonafluoro-s-butyl | Br | CF₃ | Me | 6-(trifluoromethyl)pyridin-3-yl |
| 1-302 | nonafluoro-s-butyl | I | CF₃ | Me | 6-(trifluoromethyl)pyridin-3-yl |
| 1-303 | heptafluoroisopropyl | Cl | Br | Me | phenyl |
| 1-304 | heptafluoroisopropyl | Cl | Br | Me | 4-pyridyl |
| 1-305 | heptafluoroisopropyl | Cl | Br | Me | 3-pyridyl |
| 1-306 | heptafluoroisopropyl | Cl | Br | Me | 2-pyridyl |
| 1-307 | heptafluoroisopropyl | Cl | Br | Me | 4-cyanophenyl |
| 1-308 | heptafluoroisopropyl | Cl | Br | Et | phenyl |
| 1-309 | heptafluoroisopropyl | Cl | Br | Et | 4-pyridyl |
| 1-310 | heptafluoroisopropyl | Cl | Br | Et | 3-pyridyl |
| 1-311 | heptafluoroisopropyl | Cl | Br | Et | 2-pyridyl |
| 1-312 | heptafluoroisopropyl | Cl | Br | Me | 4-cyanophenyl |
| 1-313 | heptafluoroisopropyl | Et | Br | Me | phenyl |
| 1-314 | heptafluoroisopropyl | Et | Br | Me | 4-pyridyl |
| 1-315 | heptafluoroisopropyl | Et | Br | Me | 3-pyridyl |
| 1-316 | heptafluoroisopropyl | Et | Br | Me | 2-pyridyl |
| 1-317 | heptafluoroisopropyl | Cl | Br | Me | 4-cyanophenyl |
| 1-318 | heptafluoroisopropyl | Et | Br | Et | phenyl |
| 1-319 | heptafluoroisopropyl | Et | Br | Et | 4-pyridyl |
| 1-320 | heptafluoroisopropyl | Et | Br | Et | 3-pyridyl |
| 1-321 | heptafluoroisopropyl | Et | Br | Et | 2-pyridyl |
| 1-322 | heptafluoroisopropyl | Cl | Br | Me | 4-cyanophenyl |
| 1-323 | heptafluoroisopropyl | Br | Br | Me | phenyl |
| 1-324 | heptafluoroisopropyl | Br | Br | Me | 4-pyridyl |
| 1-325 | heptafluoroisopropyl | Br | Br | Me | 3-pyridyl |
| 1-326 | heptafluoroisopropyl | Br | Br | Me | 2-pyridyl |
| 1-327 | heptafluoroisopropyl | Br | Br | Me | 4-cyanophenyl |
| 1-328 | heptafluoroisopropyl | Br | Br | Et | phenyl |
| 1-329 | heptafluoroisopropyl | Br | Br | Et | 4-pyridyl |
| 1-330 | heptafluoroisopropyl | Br | Br | Et | 3-pyridyl |

TABLE 10

| Compound No. | R¹ | X¹ | X² | R⁴ | Q |
|---|---|---|---|---|---|
| 1-331 | heptafluoroisopropyl | Br | Br | Et | 2-pyridyl |
| 1-332 | heptafluoroisopropyl | Br | Br | Me | 4-cyanophenyl |
| 1-333 | heptafluoroisopropyl | Br | Br | Me | phenyl |
| 1-334 | heptafluoroisopropyl | Br | Br | Me | 4-pyridyl |
| 1-335 | heptafluoroisopropyl | Br | Br | Me | 3-pyridyl |
| 1-336 | heptafluoroisopropyl | Br | Br | Me | 2-pyridyl |
| 1-337 | heptafluoroisopropyl | Br | Br | Me | 4-cyanophenyl |
| 1-338 | heptafluoroisopropyl | Br | Br | Et | phenyl |
| 1-339 | heptafluoroisopropyl | Br | Br | Et | 4-pyridyl |
| 1-340 | heptafluoroisopropyl | Br | Br | Et | 3-pyridyl |
| 1-341 | heptafluoroisopropyl | Br | Br | Et | 2-pyridyl |
| 1-342 | heptafluoroisopropyl | Br | Br | Me | 4-cyanophenyl |
| 1-343 | heptafluoroisopropyl | Br | Br | H | N-ethyl-N-methylaminocarbonyl |
| 1-344 | heptafluoroisopropyl | Br | Br | Me | N-ethyl-N-methylaminocarbonyl |
| 1-345 | heptafluoroisopropyl | Br | difluoromethoxy | H | N-ethyl-N-methylaminocarbonyl |
| 1-346 | heptafluoroisopropyl | Br | difluoromethoxy | Me | N-ethyl-N-methylaminocarbonyl |
| 1-347 | heptafluoroisopropyl | Me | difluoromethoxy | H | N-ethyl-N-methylaminocarbonyl |
| 1-348 | heptafluoroisopropyl | Me | difluoromethoxy | Me | N-ethyl-N-methylaminocarbonyl |
| 1-349 | heptafluoroisopropyl | Me | Et | H | N-ethyl-N-methylaminocarbonyl |
| 1-350 | heptafluoroisopropyl | Me | Et | Me | N-ethyl-N-methylaminocarbonyl |
| 1-351 | heptafluoroisopropyl | Br | Br | H | N-(2,2,2-trifluoroethyl)-N-methylaminocarbonyl |
| 1-352 | heptafluoroisopropyl | Br | Br | Me | N-(2,2,2-trifluoroethyl)-N-methylaminocarbonyl |
| 1-353 | heptafluoroisopropyl | Br | difluoromethoxy | H | N-(2,2,2-trifluoroethyl)-N-methylaminocarbonyl |
| 1-354 | heptafluoroisopropyl | Br | difluoromethoxy | Me | N-(2,2,2-trifluoroethyl)-N-methylaminocarbonyl |
| 1-355 | heptafluoroisopropyl | Me | difluoromethoxy | H | N-(2,2,2-trifluoroethyl)-N-methylaminocarbonyl |
| 1-356 | heptafluoroisopropyl | Me | difluoromethoxy | Me | N-(2,2,2-trifluoroethyl)-N-methylaminocarbonyl |
| 1-357 | heptafluoroisopropyl | Me | Et | H | N-(2,2,2-trifluoroethyl)-N-methylaminocarbonyl |
| 1-358 | heptafluoroisopropyl | Me | Et | Me | N-(2,2,2-trifluoroethyl)-N-methylaminocarbonyl |

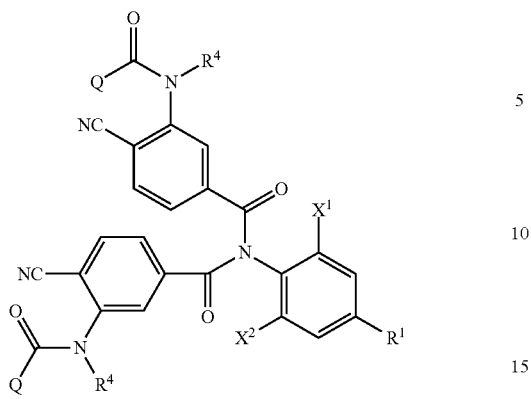

TABLE 11

| Compound No. | R¹ | X¹ | X² | R⁴ | Q |
|---|---|---|---|---|---|
| 1-359 | heptafluoroisopropyl | Br | Me | H | phenyl |
| 1-360 | heptafluoroisopropyl | I | Me | H | phenyl |
| 1-361 | heptafluoroisopropyl | Br | Me | Me | phenyl |
| 1-362 | heptafluoroisopropyl | I | Me | Me | phenyl |
| 1-363 | heptafluoroisopropyl | Br | Me | H | 4-fluorophenyl |
| 1-364 | heptafluoroisopropyl | I | Me | H | 4-fluorophenyl |
| 1-365 | heptafluoroisopropyl | Br | Me | Me | 4-fluorophenyl |
| 1-366 | heptafluoroisopropyl | I | Me | Me | 4-fluorophenyl |
| 1-367 | heptafluoroisopropyl | Br | Me | H | 6-(trifluoromethyl)pyridin-3-yl |
| 1-368 | heptafluoroisopropyl | I | Me | H | 6-(trifluoromethyl)pyridin-3-yl |
| 1-369 | heptafluoroisopropyl | Br | Me | Me | 6-(trifluoromethyl)pyridin-3-yl |
| 1-370 | heptafluoroisopropyl | I | Me | Me | 6-(trifluoromethyl)pyridin-3-yl |
| 1-371 | heptafluoroisopropyl | Br | $CF_3$ | H | phenyl |
| 1-372 | heptafluoroisopropyl | I | $CF_3$ | H | phenyl |
| 1-373 | heptafluoroisopropyl | Br | $CF_3$ | Me | phenyl |
| 1-374 | heptafluoroisopropyl | I | $CF_3$ | Me | phenyl |
| 1-375 | heptafluoroisopropyl | Br | $CF_3$ | H | 4-fluorophenyl |
| 1-376 | heptafluoroisopropyl | I | $CF_3$ | H | 4-fluorophenyl |
| 1-377 | heptafluoroisopropyl | Br | $CF_3$ | Me | 4-fluorophenyl |
| 1-378 | heptafluoroisopropyl | I | $CF_3$ | Me | 4-fluorophenyl |
| 1-379 | heptafluoroisopropyl | Br | $CF_3$ | H | 6-(trifluoromethyl)pyridin-3-yl |
| 1-380 | heptafluoroisopropyl | I | $CF_3$ | H | 6-(trifluoromethyl)pyridin-3-yl |
| 1-381 | heptafluoroisopropyl | Br | $CF_3$ | Me | 6-(trifluoromethyl)pyridin-3-yl |
| 1-382 | heptafluoroisopropyl | I | $CF_3$ | Me | 6-(trifluoromethyl)pyridin-3-yl |
| 1-383 | heptafluoroisopropyl | Me | Me | Me | phenyl |
| 1-384 | heptafluoroisopropyl | Me | Me | Me | 4-fluorophenyl |
| 1-385 | heptafluoroisopropyl | Me | Me | Me | 6-(trifluoromethyl)pyridin-3-yl |
| 1-386 | heptafluoroisopropyl | Me | Me | Me | 4-cyanophenyl |
| 1-387 | nonafluoro-s-butyl | Br | Me | H | phenyl |
| 1-388 | nonafluoro-s-butyl | I | Me | H | phenyl |
| 1-389 | nonafluoro-s-butyl | Br | Me | Me | phenyl |
| 1-390 | nonafluoro-s-butyl | I | Me | Me | phenyl |
| 1-391 | nonafluoro-s-butyl | Br | Me | H | 4-fluorophenyl |
| 1-392 | nonafluoro-s-butyl | I | Me | H | 4-fluorophenyl |
| 1-393 | nonafluoro-s-butyl | Br | Me | Me | 4-fluorophenyl |
| 1-394 | nonafluoro-s-butyl | I | Me | Me | 4-fluorophenyl |
| 1-395 | nonafluoro-s-butyl | Br | Me | H | 6-(trifluoromethyl)pyridin-3-yl |
| 1-396 | nonafluoro-s-butyl | I | Me | H | 6-(trifluoromethyl)pyridin-3-yl |
| 1-397 | nonafluoro-s-butyl | Br | Me | Me | 6-(trifluoromethyl)pyridin-3-yl |
| 1-398 | nonafluoro-s-butyl | I | Me | Me | 6-(trifluoromethyl)pyridin-3-yl |
| 1-399 | nonafluoro-s-butyl | Br | $CF_3$ | H | phenyl |
| 1-400 | nonafluoro-s-butyl | I | $CF_3$ | H | phenyl |

TABLE 12

| Compound No. | R¹ | X¹ | X² | R⁴ | Q |
|---|---|---|---|---|---|
| 1-401 | nonafluoro-s-butyl | Br | CF₃ | Me | phenyl |
| 1-402 | nonafluoro-s-butyl | I | CF₃ | Me | phenyl |
| 1-403 | nonafluoro-s-butyl | Br | CF₃ | H | 4-fluorophenyl |
| 1-404 | nonafluoro-s-butyl | I | CF₃ | H | 4-fluorophenyl |
| 1-405 | nonafluoro-s-butyl | Br | CF₃ | Me | 4-fluorophenyl |
| 1-406 | nonafluoro-s-butyl | I | CF₃ | Me | 4-fluorophenyl |
| 1-407 | nonafluoro-s-butyl | Br | CF₃ | H | 6-(trifluoromethyl)pyridin-3-yl |
| 1-408 | nonafluoro-s-butyl | I | CF₃ | H | 6-(trifluoromethyl)pyridin-3-yl |
| 1-409 | nonafluoro-s-butyl | Br | CF₃ | Me | 6-(trifluoromethyl)pyridin-3-yl |
| 1-410 | nonafluoro-s-butyl | I | CF₃ | Me | 6-(trifluoromethyl)pyridin-3-yl |
| 1-411 | heptafluoroisopropyl | Cl | Br | Me | phenyl |
| 1-412 | heptafluoroisopropyl | Cl | Br | Me | 4-pyridyl |
| 1-413 | heptafluoroisopropyl | Cl | Br | Me | 3-pyridyl |
| 1-414 | heptafluoroisopropyl | Cl | Br | Me | 2-pyridyl |
| 1-415 | heptafluoroisopropyl | Cl | Br | Me | 4-cyanophenyl |
| 1-416 | heptafluoroisopropyl | Cl | Br | Et | phenyl |
| 1-417 | heptafluoroisopropyl | Cl | Br | Et | 4-pyridyl |
| 1-418 | heptafluoroisopropyl | Cl | Br | Et | 3-pyridyl |
| 1-419 | heptafluoroisopropyl | Cl | Br | Et | 2-pyridyl |
| 1-420 | heptafluoroisopropyl | Cl | Br | Me | 4-cyanophenyl |
| 1-421 | heptafluoroisopropyl | Et | Br | Me | phenyl |
| 1-422 | heptafluoroisopropyl | Et | Br | Me | 4-pyridyl |
| 1-423 | heptafluoroisopropyl | Et | Br | Me | 3-pyridyl |
| 1-424 | heptafluoroisopropyl | Et | Br | Me | 2-pyridyl |
| 1-425 | heptafluoroisopropyl | Cl | Br | Me | 4-cyanophenyl |
| 1-426 | heptafluoroisopropyl | Et | Br | Et | phenyl |
| 1-427 | heptafluoroisopropyl | Et | Br | Et | 4-pyridyl |
| 1-428 | heptafluoroisopropyl | Et | Br | Et | 3-pyridyl |
| 1-429 | heptafluoroisopropyl | Et | Br | Et | 2-pyridyl |
| 1-430 | heptafluoroisopropyl | Cl | Br | Me | 4-cyanophenyl |
| 1-431 | heptafluoroisopropyl | Br | Br | Me | phenyl |
| 1-432 | heptafluoroisopropyl | Br | Br | Me | 4-pyridyl |
| 1-433 | heptafluoroisopropyl | Br | Br | Me | 3-pyridyl |
| 1-434 | heptafluoroisopropyl | Br | Br | Me | 2-pyridyl |
| 1-435 | heptafluoroisopropyl | Br | Br | Me | 4-cyanophenyl |
| 1-436 | heptafluoroisopropyl | Br | Br | Et | phenyl |
| 1-437 | heptafluoroisopropyl | Br | Br | Et | 4-pyridyl |
| 1-438 | heptafluoroisopropyl | Br | Br | Et | 3-pyridyl |
| 1-439 | heptafluoroisopropyl | Br | Br | Et | 2-pyridyl |
| 1-440 | heptafluoroisopropyl | Br | Br | Me | 4-cyanophenyl |

TABLE 13

| Compound No. | R¹ | X¹ | X² | R⁴ | Q |
|---|---|---|---|---|---|
| 1-441 | heptafluoroisopropyl | Br | Br | Me | phenyl |
| 1-442 | heptafluoroisopropyl | Br | Br | Me | 4-pyridyl |
| 1-443 | heptafluoroisopropyl | Br | Br | Me | 3-pyridyl |
| 1-444 | heptafluoroisopropyl | Br | Br | Me | 2-pyridyl |
| 1-445 | heptafluoroisopropyl | Br | Br | Me | 4-cyanophenyl |
| 1-446 | heptafluoroisopropyl | Br | Br | Et | phenyl |
| 1-447 | heptafluoroisopropyl | Br | Br | Et | 4-pyridyl |
| 1-448 | heptafluoroisopropyl | Br | Br | Et | 3-pyridyl |
| 1-449 | heptafluoroisopropyl | Br | Br | Et | 2-pyridyl |
| 1-450 | heptafluoroisopropyl | Br | Br | Me | 4-cyanophenyl |
| 1-451 | heptafluoroisopropyl | Br | Br | H | N-ethyl-N-methylaminocarbonyl |
| 1-452 | heptafluoroisopropyl | Br | Br | Me | N-ethyl-N-methylaminocarbonyl |
| 1-453 | heptafluoroisopropyl | Br | difluoromethoxy | H | N-ethyl-N-methylaminocarbonyl |
| 1-454 | heptafluoroisopropyl | Br | difluoromethoxy | Me | N-ethyl-N-methylaminocarbonyl |
| 1-455 | heptafluoroisopropyl | Me | difluoromethoxy | H | N-ethyl-N-methylaminocarbonyl |
| 1-456 | heptafluoroisopropyl | Me | difluoromethoxy | Me | N-ethyl-N-methylaminocarbonyl |
| 1-457 | heptafluoroisopropyl | Me | Et | H | N-ethyl-N-methylaminocarbonyl |
| 1-458 | heptafluoroisopropyl | Me | Et | Me | N-ethyl-N-methylaminocarbonyl |
| 1-459 | heptafluoroisopropyl | Br | Br | H | N-(2,2,2-trifluoroethyl)-N-methylaminocarbonyl |
| 1-460 | heptafluoroisopropyl | Br | Br | Me | N-(2,2,2-trifluoroethyl)-N-methylaminocarbonyl |
| 1-461 | heptafluoroisopropyl | Br | difluoromethoxy | H | N-(2,2,2-trifluoroethyl)-N-methylaminocarbonyl |
| 1-462 | heptafluoroisopropyl | Br | difluoromethoxy | Me | N-(2,2,2-trifluoroethyl)-N-methylaminocarbonyl |
| 1-463 | heptafluoroisopropyl | Me | difluoromethoxy | H | N-(2,2,2-trifluoroethyl)-N-methylaminocarbonyl |
| 1-464 | heptafluoroisopropyl | Me | difluoromethoxy | Me | N-(2,2,2-trifluoroethyl)-N-methylaminocarbonyl |
| 1-465 | heptafluoroisopropyl | Me | Et | H | N-(2,2,2-trifluoroethyl)-N-methylaminocarbonyl |
| 1-466 | heptafluoroisopropyl | Me | Et | Me | N-(2,2,2-trifluoroethyl)-N-methylaminocarbonyl |

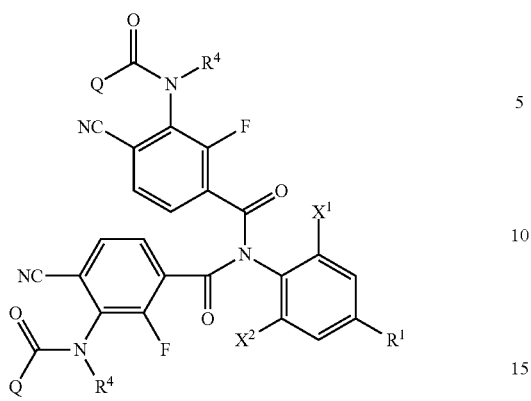

TABLE 14

| Compound No. | R¹ | X¹ | X² | R⁴ | Q |
|---|---|---|---|---|---|
| 1-467 | heptafluoroisopropyl | Br | Me | H | phenyl |
| 1-468 | heptafluoroisopropyl | I | Me | H | phenyl |
| 1-469 | heptafluoroisopropyl | Br | Me | Me | phenyl |
| 1-470 | heptafluoroisopropyl | I | Me | Me | phenyl |
| 1-471 | heptafluoroisopropyl | Br | Me | H | 4-fluorophenyl |
| 1-472 | heptafluoroisopropyl | I | Me | H | 4-fluorophenyl |
| 1-473 | heptafluoroisopropyl | Br | Me | Me | 4-fluorophenyl |
| 1-474 | heptafluoroisopropyl | I | Me | Me | 4-fluorophenyl |
| 1-475 | heptafluoroisopropyl | Br | Me | H | 6-(trifluoromethyl)pyridin-3-yl |
| 1-476 | heptafluoroisopropyl | I | Me | H | 6-(trifluoromethyl)pyridin-3-yl |
| 1-477 | heptafluoroisopropyl | Br | Me | Me | 6-(trifluoromethyl)pyridin-3-yl |
| 1-478 | heptafluoroisopropyl | I | Me | Me | 6-(trifluoromethyl)pyridin-3-yl |
| 1-479 | heptafluoroisopropyl | Br | CF₃ | H | phenyl |
| 1-480 | heptafluoroisopropyl | I | CF₃ | H | phenyl |
| 1-481 | heptafluoroisopropyl | Br | CF₃ | Me | phenyl |
| 1-482 | heptafluoroisopropyl | I | CF₃ | Me | phenyl |
| 1-483 | heptafluoroisopropyl | Br | CF₃ | H | 4-fluorophenyl |
| 1-484 | heptafluoroisopropyl | I | CF₃ | H | 4-fluorophenyl |
| 1-485 | heptafluoroisopropyl | Br | CF₃ | Me | 4-fluorophenyl |
| 1-486 | heptafluoroisopropyl | I | CF₃ | Me | 4-fluorophenyl |
| 1-487 | heptafluoroisopropyl | Br | CF₃ | H | 6-(trifluoromethyl)pyridin-3-yl |
| 1-488 | heptafluoroisopropyl | I | CF₃ | H | 6-(trifluoromethyl)pyridin-3-yl |
| 1-489 | heptafluoroisopropyl | Br | CF₃ | Me | 6-(trifluoromethyl)pyridin-3-yl |
| 1-490 | heptafluoroisopropyl | I | CF₃ | Me | 6-(trifluoromethyl)pyridin-3-yl |
| 1-491 | heptafluoroisopropyl | Me | Me | Me | phenyl |
| 1-492 | heptafluoroisopropyl | Me | Me | Me | 4-fluorophenyl |
| 1-493 | heptafluoroisopropyl | Me | Me | Me | 6-(trifluoromethyl)pyridin-3-yl |
| 1-494 | heptafluoroisopropyl | Me | Me | Me | 4-cyanophenyl |
| 1-495 | nonafluoro-s-butyl | Br | Me | H | phenyl |
| 1-496 | nonafluoro-s-butyl | I | Me | H | phenyl |
| 1-497 | nonafluoro-s-butyl | Br | Me | Me | phenyl |
| 1-498 | nonafluoro-s-butyl | I | Me | Me | phenyl |
| 1-499 | nonafluoro-s-butyl | Br | Me | H | 4-fluorophenyl |
| 1-500 | nonafluoro-s-butyl | I | Me | H | 4-fluorophenyl |
| 1-501 | nonafluoro-s-butyl | Br | Me | Me | 4-fluorophenyl |
| 1-502 | nonafluoro-s-butyl | I | Me | Me | 4-fluorophenyl |
| 1-503 | nonafluoro-s-butyl | Br | Me | H | 6-(trifluoromethyl)pyridin-3-yl |
| 1-504 | nonafluoro-s-butyl | I | Me | H | 6-(trifluoromethyl)pyridin-3-yl |
| 1-505 | nonafluoro-s-butyl | Br | Me | Me | 6-(trifluoromethyl)pyridin-3-yl |
| 1-506 | nonafluoro-s-butyl | I | Me | Me | 6-(trifluoromethyl)pyridin-3-yl |

TABLE 15

| Compound No. | R¹ | X¹ | X² | R⁴ | Q |
|---|---|---|---|---|---|
| 1-507 | nonafluoro-s-butyl | Br | CF₃ | H | phenyl |
| 1-508 | nonafluoro-s-butyl | I | CF₃ | H | phenyl |
| 1-509 | nonafluoro-s-butyl | Br | CF₃ | Me | phenyl |
| 1-510 | nonafluoro-s-butyl | I | CF₃ | Me | phenyl |
| 1-511 | nonafluoro-s-butyl | Br | CF₃ | H | 4-fluorophenyl |

TABLE 15-continued

| Compound No. | R¹ | X¹ | X² | R⁴ | Q |
|---|---|---|---|---|---|
| 1-512 | nonafluoro-s-butyl | I | CF₃ | H | 4-fluorophenyl |
| 1-513 | nonafluoro-s-butyl | Br | CF₃ | Me | 4-fluorophenyl |
| 1-514 | nonafluoro-s-butyl | I | CF₃ | Me | 4-fluorophenyl |
| 1-515 | nonafluoro-s-butyl | Br | CF₃ | H | 6-(trifluoromethyl)pyridin-3-yl |
| 1-516 | nonafluoro-s-butyl | I | CF₃ | H | 6-(trifluoromethyl)pyridin-3-yl |
| 1-517 | nonafluoro-s-butyl | Br | CF₃ | Me | 6-(trifluoromethyl)pyridin-3-yl |
| 1-518 | nonafluoro-s-butyl | I | CF₃ | Me | 6-(trifluoromethyl)pyridin-3-yl |
| 1-519 | heptafluoroisopropyl | Cl | Br | Me | phenyl |
| 1-520 | heptafluoroisopropyl | Cl | Br | Me | 4-pyridyl |
| 1-521 | heptafluoroisopropyl | Cl | Br | Me | 3-pyridyl |
| 1-522 | heptafluoroisopropyl | Cl | Br | Me | 2-pyridyl |
| 1-523 | heptafluoroisopropyl | Cl | Br | Me | 4-cyanophenyl |
| 1-524 | heptafluoroisopropyl | Cl | Br | Et | phenyl |
| 1-525 | heptafluoroisopropyl | Cl | Br | Et | 4-pyridyl |
| 1-526 | heptafluoroisopropyl | Cl | Br | Et | 3-pyridyl |
| 1-527 | heptafluoroisopropyl | Cl | Br | Et | 2-pyridyl |
| 1-528 | heptafluoroisopropyl | Cl | Br | Me | 4-cyanophenyl |
| 1-529 | heptafluoroisopropyl | Et | Br | Me | phenyl |
| 1-530 | heptafluoroisopropyl | Et | Br | Me | 4-pyridyl |
| 1-531 | heptafluoroisopropyl | Et | Br | Me | 3-pyridyl |
| 1-532 | heptafluoroisopropyl | Et | Br | Me | 2-pyridyl |
| 1-533 | heptafluoroisopropyl | Cl | Br | Me | 4-cyanophenyl |
| 1-534 | heptafluoroisopropyl | Et | Br | Et | phenyl |
| 1-535 | heptafluoroisopropyl | Et | Br | Et | 4-pyridyl |
| 1-536 | heptafluoroisopropyl | Et | Br | Et | 3-pyridyl |
| 1-537 | heptafluoroisopropyl | Et | Br | Et | 2-pyridyl |
| 1-538 | heptafluoroisopropyl | Cl | Br | Me | 4-cyanophenyl |
| 1-539 | heptafluoroisopropyl | Br | Br | Me | phenyl |
| 1-540 | heptafluoroisopropyl | Br | Br | Me | 4-pyridyl |
| 1-541 | heptafluoroisopropyl | Br | Br | Me | 3-pyridyl |
| 1-542 | heptafluoroisopropyl | Br | Br | Me | 2-pyridyl |
| 1-543 | heptafluoroisopropyl | Br | Br | Me | 4-cyanophenyl |
| 1-544 | heptafluoroisopropyl | Br | Br | Et | phenyl |
| 1-545 | heptafluoroisopropyl | Br | Br | Et | 4-pyridyl |
| 1-546 | heptafluoroisopropyl | Br | Br | Et | 3-pyridyl |
| 1-547 | heptafluoroisopropyl | Br | Br | Et | 2-pyridyl |

TABLE 16

| Compound No. | R¹ | X¹ | X² | R⁴ | Q |
|---|---|---|---|---|---|
| 1-548 | heptafluoroisopropyl | Br | Br | Me | 4-cyanophenyl |
| 1-549 | heptafluoroisopropyl | Br | Br | Me | phenyl |
| 1-550 | heptafluoroisopropyl | Br | Br | Me | 4-pyridyl |
| 1-551 | heptafluoroisopropyl | Br | Br | Me | 3-pyridyl |
| 1-552 | heptafluoroisopropyl | Br | Br | Me | 2-pyridyl |
| 1-553 | heptafluoroisopropyl | Br | Br | Me | 4-cyanophenyl |
| 1-554 | heptafluoroisopropyl | Br | Br | Et | phenyl |
| 1-555 | heptafluoroisopropyl | Br | Br | Et | 4-pyridyl |
| 1-556 | heptafluoroisopropyl | Br | Br | Et | 3-pyridyl |
| 1-557 | heptafluoroisopropyl | Br | Br | Et | 2-pyridyl |
| 1-558 | heptafluoroisopropyl | Br | Br | Me | 4-cyanophenyl |
| 1-559 | heptafluoroisopropyl | Br | Br | H | N-ethyl-N-methylaminocarbonyl |
| 1-560 | heptafluoroisopropyl | Br | Br | Me | N-ethyl-N-methylaminocarbonyl |
| 1-561 | heptafluoroisopropyl | Br | difluoromethoxy | H | N-ethyl-N-methylaminocarbonyl |
| 1-562 | heptafluoroisopropyl | Br | difluoromethoxy | Me | N-ethyl-N-methylaminocarbonyl |
| 1-563 | heptafluoroisopropyl | Me | difluoromethoxy | H | N-ethyl-N-methylaminocarbonyl |
| 1-564 | heptafluoroisopropyl | Me | difluoromethoxy | Me | N-ethyl-N-methylaminocarbonyl |
| 1-565 | heptafluoroisopropyl | Me | Et | H | N-ethyl-N-methylaminocarbonyl |
| 1-566 | heptafluoroisopropyl | Me | Et | Me | N-ethyl-N-methylaminocarbonyl |
| 1-567 | heptafluoroisopropyl | Br | Br | H | N-(2,2,2-trifluoroethyl)-N-methylaminocarbonyl |
| 1-568 | heptafluoroisopropyl | Br | Br | Me | N-(2,2,2-trifluoroethyl)-N-methylaminocarbonyl |
| 1-569 | heptafluoroisopropyl | Br | difluoromethoxy | H | N-(2,2,2-trifluoroethyl)-N-methylaminocarbonyl |
| 1-570 | heptafluoroisopropyl | Br | difluoromethoxy | Me | N-(2,2,2-trifluoroethyl)-N-methylaminocarbonyl |
| 1-571 | heptafluoroisopropyl | Me | difluoromethoxy | H | N-(2,2,2-trifluoroethyl)-N-methylaminocarbonyl |
| 1-572 | heptafluoroisopropyl | Me | difluoromethoxy | Me | N-(2,2,2-trifluoroethyl)-N-methylaminocarbonyl |
| 1-573 | heptafluoroisopropyl | Me | Et | H | N-(2,2,2-trifluoroethyl)-N-methylaminocarbonyl |
| 1-574 | heptafluoroisopropyl | Me | Et | Me | N-(2,2,2-trifluoroethyl)-N-methylaminocarbonyl |

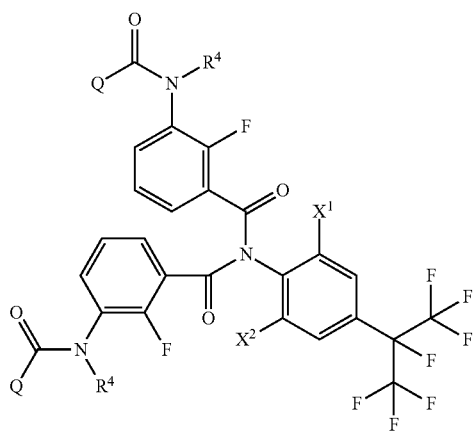

TABLE 17

| Compound No. | X¹ | X² | R⁴ | Q |
|---|---|---|---|---|
| 1-575 | CF₃ | Br | H | 4-nitrophenyl |
| 1-576 | CF₃ | I | H | 4-nitrophenyl |
| 1-577 | CF₃ | Br | Me | 4-nitrophenyl |
| 1-578 | CF₃ | I | Me | 4-nitrophenyl |
| 1-579 | CF₃ | Br | H | 3-fluorophenyl |
| 1-580 | CF₃ | I | H | 3-fluorophenyl |
| 1-581 | CF₃ | Br | Me | 3-fluorophenyl |
| 1-582 | CF₃ | I | Me | 3-fluorophenyl |
| 1-583 | CF₃ | Br | H | 6-(trifluoromethyl)pyridin-2-yl |
| 1-584 | CF₃ | I | H | 6-(trifluoromethyl)pyridin-2-yl |
| 1-585 | CF₃ | Br | Me | 6-(trifluoromethyl)pyridin-2-yl |
| 1-586 | CF₃ | I | Me | 6-(trifluoromethyl)pyridin-2-yl |
| 1-587 | CF₃ | Br | H | 6-chloropyridin-2-yl |
| 1-588 | CF₃ | I | H | 6-chloropyridin-2-yl |
| 1-589 | CF₃ | Br | Me | 6-chloropyridin-2-yl |
| 1-590 | CF₃ | I | Me | 6-chloropyridin-2-yl |
| 1-591 | CF₃ | Br | H | 5-chloropyridin-3-yl |
| 1-592 | CF₃ | I | H | 5-chloropyridin-3-yl |
| 1-593 | CF₃ | Br | Me | 5-chloropyridin-3-yl |
| 1-594 | CF₃ | I | Me | 5-chloropyridin-3-yl |
| 1-595 | CF₃ | Br | H | 5-fluoropyridin-3-yl |
| 1-596 | CF₃ | I | H | 5-fluoropyridin-3-yl |
| 1-597 | CF₃ | Br | Me | 5-fluoropyridin-3-yl |
| 1-598 | CF₃ | I | Me | 5-fluoropyridin-3-yl |
| 1-599 | CF₃ | Br | H | 6-chloropyridin-3-yl |
| 1-600 | CF₃ | I | H | 6-chloropyridin-3-yl |
| 1-601 | CF₃ | Br | Me | 6-chloropyridin-3-yl |
| 1-602 | CF₃ | I | Me | 6-chloropyridin-3-yl |
| 1-603 | CF₃ | Br | H | 6-fluoropyridin-3-yl |
| 1-604 | CF₃ | I | H | 6-fluoropyridin-3-yl |
| 1-605 | CF₃ | Br | Me | 6-fluoropyridin-3-yl |
| 1-606 | CF₃ | I | Me | 6-fluoropyridin-3-yl |
| 1-607 | CF₃ | Br | H | 2,3-difluorophenyl |
| 1-608 | CF₃ | I | H | 2,3-difluorophenyl |
| 1-609 | CF₃ | Br | Me | 2,3-difluorophenyl |
| 1-610 | CF₃ | I | Me | 2,3-difluorophenyl |
| 1-611 | CF₃ | Br | H | 3,5-difluorophenyl |
| 1-612 | CF₃ | I | H | 3,5-difluorophenyl |
| 1-613 | CF₃ | Br | Me | 3,5-difluorophenyl |
| 1-614 | CF₃ | I | Me | 3,5-difluorophenyl |

TABLE 18

| Compound No. | X¹ | X² | R⁴ | Q |
|---|---|---|---|---|
| 1-615 | CF₃ | Br | H | pyridin-2-yl |
| 1-616 | CF₃ | I | H | pyridin-2-yl |
| 1-617 | CF₃ | Br | Me | pyridin-2-yl |
| 1-618 | CF₃ | I | Me | pyridin-2-yl |
| 1-619 | CF₃ | Br | H | pyridin-3-yl |
| 1-620 | CF₃ | I | H | pyridin-3-yl |
| 1-621 | CF₃ | Br | Me | pyridin-3-yl |
| 1-622 | CF₃ | I | Me | pyridin-3-yl |
| 1-623 | CF₃ | Br | H | pyridin-4-yl |
| 1-624 | CF₃ | I | H | pyridin-4-yl |
| 1-625 | CF₃ | Br | Me | pyridin-4-yl |
| 1-626 | CF₃ | I | Me | pyridin-4-yl |
| 1-627 | CF₃ | Br | H | Me |
| 1-628 | CF₃ | I | H | Me |
| 1-629 | CF₃ | Br | Me | Me |
| 1-630 | CF₃ | I | Me | Me |
| 1-631 | CF₃ | Br | H | Et |
| 1-632 | CF₃ | I | H | Et |
| 1-633 | CF₃ | Br | Me | Et |
| 1-634 | CF₃ | I | Me | Et |
| 1-635 | CF₃ | Br | H | n-Pr |
| 1-636 | CF₃ | I | H | n-Pr |
| 1-637 | CF₃ | Br | Me | n-Pr |
| 1-638 | CF₃ | I | Me | n-Pr |
| 1-639 | CF₃ | Br | H | i-Pr |
| 1-640 | CF₃ | I | H | i-Pr |
| 1-641 | CF₃ | Br | Me | i-Pr |
| 1-642 | CF₃ | I | Me | i-Pr |
| 1-643 | CF₃ | Br | H | methoxymethyl |
| 1-644 | CF₃ | I | H | methoxymethyl |
| 1-645 | CF₃ | Br | Me | methoxymethyl |
| 1-646 | CF₃ | I | Me | methoxymethyl |
| 1-647 | CF₃ | Br | H | trifluoromethyl |
| 1-648 | CF₃ | I | H | trifluoromethyl |
| 1-649 | CF₃ | Br | Me | trifluoromethyl |
| 1-650 | CF₃ | I | Me | trifluoromethyl |
| 1-651 | CF₃ | Br | H | methoxydifluoromethyl |
| 1-652 | CF₃ | I | H | methoxydifluoromethyl |
| 1-653 | CF₃ | Br | Me | methoxydifluoromethyl |
| 1-654 | CF₃ | I | Me | methoxydifluoromethyl |

TABLE 19

| Compound No. | X¹ | X² | R⁴ | Q |
|---|---|---|---|---|
| 1-655 | CF₃ | Br | H | ethylaminocarbonyl |
| 1-656 | CF₃ | I | H | ethylaminocarbonyl |
| 1-657 | CF₃ | Br | Me | ethylaminocarbonyl |
| 1-658 | CF₃ | I | Me | ethylaminocarbonyl |
| 1-659 | CF₃ | Br | H | 2,2,2-trifluoroethylaminocarbonyl |
| 1-660 | CF₃ | I | H | 2,2,2-trifluoroethylaminocarbonyl |
| 1-661 | CF₃ | Br | Me | 2,2,2-trifluoroethylaminocarbonyl |
| 1-662 | CF₃ | I | Me | 2,2,2-trifluoroethylaminocarbonyl |
| 1-663 | CF₃ | Br | H | N-ethyl-N-methylaminocarbonyl |
| 1-664 | CF₃ | I | H | N-ethyl-N-methylaminocarbonyl |
| 1-665 | CF₃ | Br | Me | N-ethyl-N-methylaminocarbonyl |
| 1-666 | CF₃ | I | Me | N-ethyl-N-methylaminocarbonyl |
| 1-667 | CF₃ | Br | H | N-(2,2,2-trifluoroethyl)-N-methylaminocarbonyl |
| 1-668 | CF₃ | I | H | N-(2,2,2-trifluoroethyl)-N-methylaminocarbonyl |
| 1-669 | CF₃ | Br | Me | N-(2,2,2-trifluoroethyl)-N-methylaminocarbonyl |
| 1-670 | CF₃ | I | Me | N-(2,2,2-trifluoroethyl)-N-methylaminocarbonyl |
| 1-671 | trifluoromethoxy | Br | H | 4-fluorophenyl |
| 1-672 | trifluoromethoxy | I | H | 4-fluorophenyl |
| 1-673 | trifluoromethoxy | Br | Me | 4-fluorophenyl |
| 1-674 | trifluoromethoxy | I | Me | 4-fluorophenyl |
| 1-675 | trifluoromethoxy | Br | H | 3-fluorophenyl |
| 1-676 | trifluoromethoxy | I | H | 3-fluorophenyl |
| 1-677 | trifluoromethoxy | Br | Me | 3-fluorophenyl |
| 1-678 | trifluoromethoxy | I | Me | 3-fluorophenyl |
| 1-679 | trifluoromethoxy | Br | H | 6-(trifluoromethyl)pyridin-2-yl |
| 1-680 | trifluoromethoxy | I | H | 6-(trifluoromethyl)pyridin-2-yl |
| 1-681 | trifluoromethoxy | Br | Me | 6-(trifluoromethyl)pyridin-2-yl |

TABLE 19-continued

| Compound No. | X¹ | X² | R⁴ | Q |
|---|---|---|---|---|
| 1-682 | trifluoromethoxy | I | Me | 6-(trifluoromethyl)pyridin-2-yl |
| 1-683 | trifluoromethoxy | Br | H | 6-chloropyridin-2-yl |
| 1-684 | trifluoromethoxy | I | H | 6-chloropyridin-2-yl |
| 1-685 | trifluoromethoxy | Br | Me | 6-chloropyridin-2-yl |
| 1-686 | trifluoromethoxy | I | Me | 6-chloropyridin-2-yl |
| 1-687 | trifluoromethoxy | Br | H | 5-chloropyridin-3-yl |
| 1-688 | trifluoromethoxy | I | H | 5-chloropyridin-3-yl |
| 1-689 | trifluoromethoxy | Br | Me | 5-chloropyridin-3-yl |
| 1-690 | trifluoromethoxy | I | Me | 5-chloropyridin-3-yl |
| 1-691 | trifluoromethoxy | Br | H | 5-fluoropyridin-3-yl |
| 1-692 | trifluoromethoxy | I | H | 5-fluoropyridin-3-yl |

TABLE 20

| Compound No. | X¹ | X² | R⁴ | Q |
|---|---|---|---|---|
| 1-693 | trifluoromethoxy | Br | Me | 5-fluoropyridin-3-yl |
| 1-694 | trifluoromethoxy | I | Me | 5-fluoropyridin-3-yl |
| 1-695 | trifluoromethoxy | Br | H | 6-fluoropyridin-3-yl |
| 1-696 | trifluoromethoxy | I | H | 6-fluoropyridin-3-yl |
| 1-697 | trifluoromethoxy | Br | Me | 6-fluoropyridin-3-yl |
| 1-698 | trifluoromethoxy | I | Me | 6-fluoropyridin-3-yl |
| 1-699 | trifluoromethoxy | Br | H | 2,3-difluorophenyl |
| 1-700 | trifluoromethoxy | I | H | 2,3-difluorophenyl |
| 1-701 | trifluoromethoxy | Br | Me | 2,3-difluorophenyl |
| 1-702 | trifluoromethoxy | I | Me | 2,3-difluorophenyl |
| 1-703 | trifluoromethoxy | Br | H | 3,5-difluorophenyl |
| 1-704 | trifluoromethoxy | I | H | 3,5-difluorophenyl |
| 1-705 | trifluoromethoxy | Br | Me | 3,5-difluorophenyl |
| 1-706 | trifluoromethoxy | I | Me | 3,5-difluorophenyl |
| 1-707 | difluoromethoxy | Br | H | 4-fluorophenyl |
| 1-708 | difluoromethoxy | I | H | 4-fluorophenyl |
| 1-709 | difluoromethoxy | Br | Me | 4-fluorophenyl |
| 1-710 | difluoromethoxy | I | Me | 4-fluorophenyl |
| 1-711 | difluoromethoxy | Br | H | 3-fluorophenyl |
| 1-712 | difluoromethoxy | I | H | 3-fluorophenyl |
| 1-713 | difluoromethoxy | Br | Me | 3-fluorophenyl |
| 1-714 | difluoromethoxy | I | Me | 3-fluorophenyl |
| 1-715 | difluoromethoxy | Br | H | 6-(trifluoromethyl)pyridin-2-yl |
| 1-716 | difluoromethoxy | I | H | 6-(trifluoromethyl)pyridin-2-yl |
| 1-717 | difluoromethoxy | Br | Me | 6-(trifluoromethyl)pyridin-2-yl |
| 1-718 | difluoromethoxy | I | Me | 6-(trifluoromethyl)pyridin-2-yl |
| 1-719 | difluoromethoxy | Br | H | 6-chloropyridin-2-yl |
| 1-720 | difluoromethoxy | I | H | 6-chloropyridin-2-yl |
| 1-721 | difluoromethoxy | Br | Me | 6-chloropyridin-2-yl |
| 1-722 | difluoromethoxy | I | Me | 6-chloropyridin-2-yl |
| 1-723 | difluoromethoxy | Br | H | 5-chloropyridin-3-yl |
| 1-724 | difluoromethoxy | I | H | 5-chloropyridin-3-yl |
| 1-725 | difluoromethoxy | Br | Me | 5-chloropyridin-3-yl |
| 1-726 | difluoromethoxy | I | Me | 5-chloropyridin-3-yl |
| 1-727 | difluoromethoxy | Br | H | 5-fluoropyridin-3-yl |
| 1-728 | difluoromethoxy | I | H | 5-fluoropyridin-3-yl |
| 1-729 | difluoromethoxy | Br | Me | 5-fluoropyridin-3-yl |
| 1-730 | difluoromethoxy | I | Me | 5-fluoropyridin-3-yl |
| 1-731 | difluoromethoxy | Br | H | 6-fluoropyridin-3-yl |
| 1-732 | difluoromethoxy | I | H | 6-fluoropyridin-3-yl |

TABLE 21

| Compound No. | X¹ | X² | R⁴ | Q |
|---|---|---|---|---|
| 1-733 | difluoromethoxy | Br | Me | 6-fluoropyridin-3-yl |
| 1-734 | difluoromethoxy | I | Me | 6-fluoropyridin-3-yl |
| 1-735 | difluoromethoxy | Br | H | 2,3-difluorophenyl |
| 1-736 | difluoromethoxy | I | H | 2,3-difluorophenyl |
| 1-737 | difluoromethoxy | Br | Me | 2,3-difluorophenyl |
| 1-738 | difluoromethoxy | I | Me | 2,3-difluorophenyl |
| 1-739 | difluoromethoxy | Br | H | 3,5-difluorophenyl |
| 1-740 | difluoromethoxy | I | H | 3,5-difluorophenyl |
| 1-741 | difluoromethoxy | Br | Me | 3,5-difluorophenyl |
| 1-742 | difluoromethoxy | I | Me | 3,5-difluorophenyl |

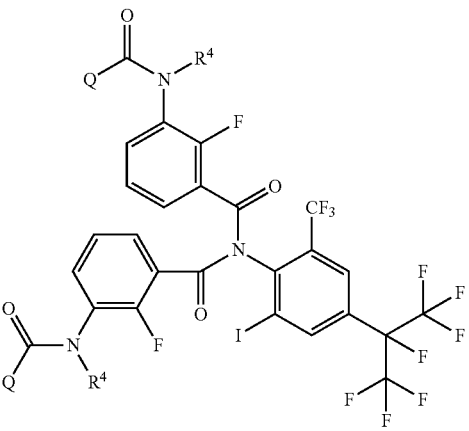

TABLE 22

| Compound No. | R⁴ | Q |
|---|---|---|
| 1-743 | ethyl | phenyl |
| 1-744 | acetyl | phenyl |
| 1-745 | ethylcarbonyl | phenyl |
| 1-746 | methoxycarbonyl | phenyl |
| 1-747 | ethoxycarbonyl | phenyl |
| 1-748 | methanesulfonyl | phenyl |
| 1-749 | methoxycarbonylethyl | phenyl |
| 1-750 | methylaminocarbonylethyl | phenyl |
| 1-751 | ethyl | 4-fluorophenyl |
| 1-752 | acetyl | 4-fluorophenyl |
| 1-753 | ethylcarbonyl | 4-fluorophenyl |
| 1-754 | methoxycarbonyl | 4-fluorophenyl |
| 1-755 | ethoxycarbonyl | 4-fluorophenyl |
| 1-756 | methanesulfonyl | 4-fluorophenyl |
| 1-757 | methoxycarbonylethyl | 4-fluorophenyl |
| 1-758 | methylaminocarbonylethyl | 4-fluorophenyl |
| 1-759 | ethyl | 6-(trifluoromethyl)pyridin-3-yl |
| 1-760 | acetyl | 6-(trifluoromethyl)pyridin-3-yl |
| 1-761 | ethylcarbonyl | 6-(trifluoromethyl)pyridin-3-yl |
| 1-762 | methoxycarbonyl | 6-(trifluoromethyl)pyridin-3-yl |
| 1-763 | ethoxycarbonyl | 6-(trifluoromethyl)pyridin-3-yl |
| 1-764 | methanesulfonyl | 6-(trifluoromethyl)pyridin-3-yl |
| 1-765 | methoxycarbonylethyl | 6-(trifluoromethyl)pyridin-3-yl |
| 1-766 | methylaminocarbonylethyl | 6-(trifluoromethyl)pyridin-3-yl |
| 1-767 | ethyl | 5-fluoropyridin-3-yl |
| 1-768 | acetyl | 5-fluoropyridin-3-yl |
| 1-769 | ethylcarbonyl | 5-fluoropyridin-3-yl |
| 1-770 | methoxycarbonyl | 5-fluoropyridin-3-yl |
| 1-771 | ethoxycarbonyl | 5-fluoropyridin-3-yl |
| 1-772 | methanesulfonyl | 5-fluoropyridin-3-yl |
| 1-773 | methoxycarbonylethyl | 5-fluoropyridin-3-yl |
| 1-774 | methylaminocarbonylethyl | 5-fluoropyridin-3-yl |
| 1-775 | ethyl | 2,3-difluorophenyl |
| 1-776 | acetyl | 2,3-difluorophenyl |
| 1-777 | ethylcarbonyl | 2,3-difluorophenyl |
| 1-778 | methoxycarbonyl | 2,3-difluorophenyl |
| 1-779 | ethoxycarbonyl | 2,3-difluorophenyl |
| 1-780 | methanesulfonyl | 2,3-difluorophenyl |
| 1-781 | methoxycarbonylethyl | 2,3-difluorophenyl |
| 1-782 | methylaminocarbonylethyl | 2,3-difluorophenyl |

TABLE 23

| Compound No. | R⁴ | Q |
| --- | --- | --- |
| 1-783 | ethyl | 3,5-difluorophenyl |
| 1-784 | acetyl | 3,5-difluorophenyl |
| 1-785 | ethylcarbonyl | 3,5-difluorophenyl |
| 1-786 | methoxycarbonyl | 3,5-difluorophenyl |
| 1-787 | ethoxycarbonyl | 3,5-difluorophenyl |
| 1-788 | methanesulfonyl | 3,5-difluorophenyl |
| 1-789 | methoxycarbonylethyl | 3,5-difluorophenyl |
| 1-790 | methylaminocarbonylethyl | 3,5-difluorophenyl |
| 1-791 | ethyl | 6-chloropyridin-2-yl |
| 1-792 | acetyl | 6-chloropyridin-2-yl |
| 1-793 | ethylcarbonyl | 6-chloropyridin-2-yl |
| 1-794 | methoxycarbonyl | 6-chloropyridin-2-yl |
| 1-795 | ethoxycarbonyl | 6-chloropyridin-2-yl |
| 1-796 | methanesulfonyl | 6-chloropyridin-2-yl |
| 1-797 | methoxycarbonylethyl | 6-chloropyridin-2-yl |
| 1-798 | methylaminocarbonylethyl | 6-chloropyridin-2-yl |
| 1-799 | ethyl | 5-chloropyridin-3-yl |
| 1-800 | acetyl | 5-chloropyridin-3-yl |
| 1-801 | ethylcarbonyl | 5-chloropyridin-3-yl |
| 1-802 | methoxycarbonyl | 5-chloropyridin-3-yl |
| 1-803 | ethoxycarbonyl | 5-chloropyridin-3-yl |
| 1-804 | methanesulfonyl | 5-chloropyridin-3-yl |
| 1-805 | methoxycarbonylethyl | 5-chloropyridin-3-yl |
| 1-806 | methylaminocarbonylethyl | 5-chloropyridin-3-yl |

Although representative compounds of the aromatic amide derivatives represented by Formula (I) of the invention are illustrated below, the invention is not limited to these compounds.

Incidentally, in the illustrated compounds shown below, "Me" represents a methyl group, "Et" represents an ethyl group, "Pr" represents a propyl group, "H" represents a hydrogen atom, "F" represents a fluorine atom, "Cl" represents a chlorine atom, "Br" represents a bromine atom, "I" represents an iodine atom, and "CF₃" represents a trifluoromethyl group, respectively

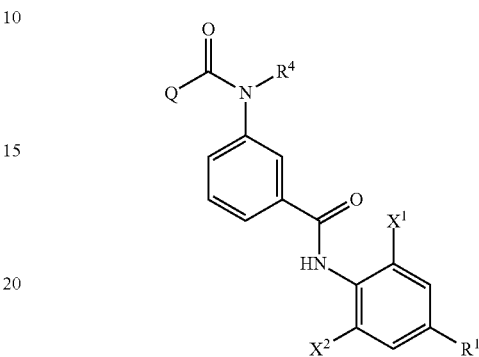

TABLE 24

| Compound No. | R¹ | X¹ | X² | R⁴ | Q |
| --- | --- | --- | --- | --- |--- |
| 2-001 | heptafluoroisopropyl | Br | Me | H | phenyl |
| 2-002 | heptafluoroisopropyl | I | Me | H | phenyl |
| 2-003 | heptafluoroisopropyl | Br | Me | Me | phenyl |
| 2-004 | heptafluoroisopropyl | I | Me | Me | phenyl |
| 2-005 | heptafluoroisopropyl | Br | Me | H | 4-fluorophenyl |
| 2-006 | heptafluoroisopropyl | I | Me | H | 4-fluorophenyl |
| 2-007 | heptafluoroisopropyl | Br | Me | Me | 4-fluorophenyl |
| 2-008 | heptafluoroisopropyl | I | Me | Me | 4-fluorophenyl |
| 2-009 | heptafluoroisopropyl | Br | Me | H | 6-(trifluoromethyl)pyridin-3-yl |
| 2-010 | heptafluoroisopropyl | I | Me | H | 6-(trifluoromethyl)pyridin-3-yl |
| 2-011 | heptafluoroisopropyl | Br | Me | Me | 6-(trifluoromethyl)pyridin-3-yl |
| 2-012 | heptafluoroisopropyl | I | Me | Me | 6-(trifluoromethyl)pyridin-3-yl |
| 2-013 | heptafluoroisopropyl | Br | CF₃ | H | phenyl |
| 2-014 | heptafluoroisopropyl | I | CF₃ | H | phenyl |
| 2-015 | heptafluoroisopropyl | Br | CF₃ | Me | phenyl |
| 2-016 | heptafluoroisopropyl | I | CF₃ | Me | phenyl |
| 2-017 | heptafluoroisopropyl | Br | CF₃ | H | 4-fluorophenyl |
| 2-018 | heptafluoroisopropyl | I | CF₃ | H | 4-fluorophenyl |
| 2-019 | heptafluoroisopropyl | Br | CF₃ | Me | 4-fluorophenyl |
| 2-020 | heptafluoroisopropyl | I | CF₃ | Me | 4-fluorophenyl |
| 2-021 | heptafluoroisopropyl | Br | CF₃ | H | 6-(trifluoromethyl)pyridin-3-yl |
| 2-022 | heptafluoroisopropyl | I | CF₃ | H | 6-(trifluoromethyl)pyridin-3-yl |
| 2-023 | heptafluoroisopropyl | Br | CF₃ | Me | 6-(trifluoromethyl)pyridin-3-yl |
| 2-024 | heptafluoroisopropyl | I | CF₃ | Me | 6-(trifluoromethyl)pyridin-3-yl |
| 2-025 | heptafluoroisopropyl | Me | Me | Me | phenyl |
| 2-026 | heptafluoroisopropyl | Me | Me | Me | 4-fluorophenyl |
| 2-027 | heptafluoroisopropyl | Me | Me | Me | 6-(trifluoromethyl)pyridin-3-yl |
| 2-028 | heptafluoroisopropyl | Me | Me | Me | 4-cyanophenyl |
| 2-029 | nonafluoro-s-butyl | Br | Me | H | phenyl |
| 2-030 | nonafluoro-s-butyl | I | Me | H | phenyl |
| 2-031 | nonafluoro-s-butyl | Br | Me | Me | phenyl |
| 2-032 | nonafluoro-s-butyl | I | Me | Me | phenyl |
| 2-033 | nonafluoro-s-butyl | Br | Me | H | 4-fluorophenyl |
| 2-034 | nonafluoro-s-butyl | I | Me | H | 4-fluorophenyl |
| 2-035 | nonafluoro-s-butyl | Br | Me | Me | 4-fluorophenyl |
| 2-036 | nonafluoro-s-butyl | I | Me | Me | 4-fluorophenyl |
| 2-037 | nonafluoro-s-butyl | Br | Me | H | 6-(trifluoromethyl)pyridin-3-yl |
| 2-038 | nonafluoro-s-butyl | I | Me | H | 6-(trifluoromethyl)pyridin-3-yl |
| 2-039 | nonafluoro-s-butyl | Br | Me | Me | 6-(trifluoromethyl)pyridin-3-yl |
| 2-040 | nonafluoro-s-butyl | I | Me | Me | 6-(trifluoromethyl)pyridin-3-yl |

TABLE 25

| Compound No. | R¹ | X¹ | X² | R⁴ | Q |
|---|---|---|---|---|---|
| 2-041 | nonafluoro-s-butyl | Br | CF$_3$ | H | phenyl |
| 2-042 | nonafluoro-s-butyl | I | CF$_3$ | H | phenyl |
| 2-043 | nonafluoro-s-butyl | Br | CF$_3$ | Me | phenyl |
| 2-044 | nonafluoro-s-butyl | I | CF$_3$ | Me | phenyl |
| 2-045 | nonafluoro-s-butyl | Br | CF$_3$ | H | 4-fluorophenyl |
| 2-046 | nonafluoro-s-butyl | I | CF$_3$ | H | 4-fluorophenyl |
| 2-047 | nonafluoro-s-butyl | Br | CF$_3$ | Me | 4-fluorophenyl |
| 2-048 | nonafluoro-s-butyl | I | CF$_3$ | Me | 4-fluorophenyl |
| 2-049 | nonafluoro-s-butyl | Br | CF$_3$ | H | 6-(trifluoromethyl)pyridin-3-yl |
| 2-050 | nonafluoro-s-butyl | I | CF$_3$ | H | 6-(trifluoromethyl)pyridin-3-yl |
| 2-051 | nonafluoro-s-butyl | Br | CF$_3$ | Me | 6-(trifluoromethyl)pyridin-3-yl |
| 2-052 | nonafluoro-s-butyl | I | CF$_3$ | Me | 6-(trifluoromethyl)pyridin-3-yl |
| 2-053 | heptafluoroisopropyl | Cl | Br | Me | phenyl |
| 2-054 | heptafluoroisopropyl | Cl | Br | Me | 4-pyridyl |
| 2-055 | heptafluoroisopropyl | Cl | Br | Me | 3-pyridyl |
| 2-056 | heptafluoroisopropyl | Cl | Br | Me | 2-pyridyl |
| 2-057 | heptafluoroisopropyl | Cl | Br | Me | 4-cyanophenyl |
| 2-058 | heptafluoroisopropyl | Cl | Br | Et | phenyl |
| 2-059 | heptafluoroisopropyl | Cl | Br | Et | 4-pyridyl |
| 2-060 | heptafluoroisopropyl | Cl | Br | Et | 3-pyridyl |
| 2-061 | heptafluoroisopropyl | Cl | Br | Et | 2-pyridyl |
| 2-062 | heptafluoroisopropyl | Cl | Br | Me | 4-cyanophenyl |
| 2-063 | heptafluoroisopropyl | Et | Br | Me | phenyl |
| 2-064 | heptafluoroisopropyl | Et | Br | Me | 4-pyridyl |
| 2-065 | heptafluoroisopropyl | Et | Br | Me | 3-pyridyl |
| 2-066 | heptafluoroisopropyl | Et | Br | Me | 2-pyridyl |
| 2-067 | heptafluoroisopropyl | Cl | Br | Me | 4-cyanophenyl |
| 2-068 | heptafluoroisopropyl | Et | Br | Et | phenyl |
| 2-069 | heptafluoroisopropyl | Et | Br | Et | 4-pyridyl |
| 2-070 | heptafluoroisopropyl | Et | Br | Et | 3-pyridyl |
| 2-071 | heptafluoroisopropyl | Et | Br | Et | 2-pyridyl |
| 2-072 | heptafluoroisopropyl | Cl | Br | Me | 4-cyanophenyl |
| 2-073 | heptafluoroisopropyl | Br | Br | Me | phenyl |
| 2-074 | heptafluoroisopropyl | Br | Br | Me | 4-pyridyl |
| 2-075 | heptafluoroisopropyl | Br | Br | Me | 3-pyridyl |
| 2-076 | heptafluoroisopropyl | Br | Br | Me | 2-pyridyl |
| 2-077 | heptafluoroisopropyl | Br | Br | Me | 4-cyanophenyl |
| 2-078 | heptafluoroisopropyl | Br | Br | Et | phenyl |
| 2-079 | heptafluoroisopropyl | Br | Br | Et | 4-pyridyl |
| 2-080 | heptafluoroisopropyl | Br | Br | Et | 3-pyridyl |

TABLE 26

| Compound No. | R¹ | X¹ | X² | R⁴ | Q |
|---|---|---|---|---|---|
| 2-081 | heptafluoroisopropyl | Br | Br | Et | 2-pyridyl |
| 2-082 | heptafluoroisopropyl | Br | Br | Me | 4-cyanophenyl |
| 2-083 | heptafluoroisopropyl | Br | Br | Me | phenyl |
| 2-084 | heptafluoroisopropyl | Br | Br | Me | 4-pyridyl |
| 2-085 | heptafluoroisopropyl | Br | Br | Me | 3-pyridyl |
| 2-086 | heptafluoroisopropyl | Br | Br | Me | 2-pyridyl |
| 2-087 | heptafluoroisopropyl | Br | Br | Me | 4-cyanophenyl |
| 2-088 | heptafluoroisopropyl | Br | Br | Et | phenyl |
| 2-089 | heptafluoroisopropyl | Br | Br | Et | 4-pyridyl |
| 2-090 | heptafluoroisopropyl | Br | Br | Et | 3-pyridyl |
| 2-091 | heptafluoroisopropyl | Br | Br | Et | 2-pyridyl |
| 2-092 | heptafluoroisopropyl | Br | Br | Me | 4-cyanophenyl |
| 2-093 | heptafluoroisopropyl | Br | Br | H | N-ethyl-N-methylaminocarbonyl |
| 2-094 | heptafluoroisopropyl | Br | Br | Me | N-ethyl-N-methylaminocarbonyl |
| 2-095 | heptafluoroisopropyl | Br | difluoromethoxy | H | N-ethyl-N-methylaminocarbonyl |
| 2-096 | heptafluoroisopropyl | Br | difluoromethoxy | Me | N-ethyl-N-methylaminocarbonyl |
| 2-097 | heptafluoroisopropyl | Me | difluoromethoxy | H | N-ethyl-N-methylaminocarbonyl |
| 2-098 | heptafluoroisopropyl | Me | difluoromethoxy | Me | N-ethyl-N-methylaminocarbonyl |
| 2-099 | heptafluoroisopropyl | Me | Et | H | N-ethyl-N-methylaminocarbonyl |
| 2-100 | heptafluoroisopropyl | Me | Et | Me | N-ethyl-N-methylaminocarbonyl |
| 2-101 | heptafluoroisopropyl | Br | Br | H | N-(2,2,2-trifluoroethyl)-N-methylaminocarbonyl |
| 2-102 | heptafluoroisopropyl | Br | Br | Me | N-(2,2,2-trifluoroethyl)-N-methylaminocarbonyl |
| 2-103 | heptafluoroisopropyl | Br | difluoromethoxy | H | N-(2,2,2-trifluoroethyl)-N-methylaminocarbonyl |
| 2-104 | heptafluoroisopropyl | Br | difluoromethoxy | Me | N-(2,2,2-trifluoroethyl)-N-methylaminocarbonyl |
| 2-105 | heptafluoroisopropyl | Me | difluoromethoxy | H | N-(2,2,2-trifluoroethyl)-N-methylaminocarbonyl |
| 2-106 | heptafluoroisopropyl | Me | difluoromethoxy | Me | N-(2,2,2-trifluoroethyl)-N-methylaminocarbonyl |
| 2-107 | heptafluoroisopropyl | Me | Et | H | N-(2,2,2-trifluoroethyl)-N-methylaminocarbonyl |
| 2-108 | heptafluoroisopropyl | Me | Et | Me | N-(2,2,2-trifluoroethyl)-N-methylaminocarbonyl |

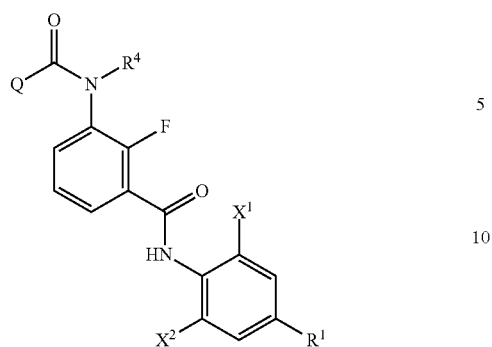

TABLE 27

| Compound No. | R¹ | X¹ | X² | R⁴ | Q |
|---|---|---|---|---|---|
| 2-109 | heptafluoroisopropyl | Br | Me | H | phenyl |
| 2-110 | heptafluoroisopropyl | I | Me | H | phenyl |
| 2-111 | heptafluoroisopropyl | Br | Me | Me | phenyl |
| 2-112 | heptafluoroisopropyl | I | Me | Me | phenyl |
| 2-113 | heptafluoroisopropyl | Br | Me | H | 4-fluorophenyl |
| 2-114 | heptafluoroisopropyl | I | Me | H | 4-fluorophenyl |
| 2-115 | heptafluoroisopropyl | Br | Me | Me | 4-fluorophenyl |
| 2-116 | heptafluoroisopropyl | I | Me | Me | 4-fluorophenyl |
| 2-117 | heptafluoroisopropyl | Br | Me | H | 6-(trifluoromethyl)pyridin-3-yl |
| 2-118 | heptafluoroisopropyl | I | Me | H | 6-(trifluoromethyl)pyridin-3-yl |
| 2-119 | heptafluoroisopropyl | Br | Me | Me | 6-(trifluoromethyl)pyridin-3-yl |
| 2-120 | heptafluoroisopropyl | I | Me | Me | 6-(trifluoromethyl)pyridin-3-yl |
| 2-121 | heptafluoroisopropyl | Br | CF₃ | H | phenyl |
| 2-122 | heptafluoroisopropyl | I | CF₃ | H | phenyl |
| 2-123 | heptafluoroisopropyl | Br | CF₃ | Me | phenyl |
| 2-124 | heptafluoroisopropyl | I | CF₃ | Me | phenyl |
| 2-125 | heptafluoroisopropyl | Br | CF₃ | H | 4-fluorophenyl |
| 2-126 | heptafluoroisopropyl | I | CF₃ | H | 4-fluorophenyl |
| 2-127 | heptafluoroisopropyl | Br | CF₃ | Me | 4-fluorophenyl |
| 2-128 | heptafluoroisopropyl | I | CF₃ | Me | 4-fluorophenyl |
| 2-129 | heptafluoroisopropyl | Br | CF₃ | H | 6-(trifluoromethyl)pyridin-3-yl |
| 2-130 | heptafluoroisopropyl | I | CF₃ | H | 6-(trifluoromethyl)pyridin-3-yl |
| 2-131 | heptafluoroisopropyl | Br | CF₃ | Me | 6-(trifluoromethyl)pyridin-3-yl |
| 2-132 | heptafluoroisopropyl | I | CF₃ | Me | 6-(trifluoromethyl)pyridin-3-yl |
| 2-133 | heptafluoroisopropyl | Br | CF₃ | H | 2,6-difluorophenyl |
| 2-134 | heptafluoroisopropyl | I | CF₃ | H | 2,6-difluorophenyl |
| 2-135 | heptafluoroisopropyl | Br | CF₃ | Me | 2,6-difluorophenyl |
| 2-136 | heptafluoroisopropyl | I | CF₃ | Me | 2,6-difluorophenyl |
| 2-137 | heptafluoroisopropyl | Me | Me | Me | phenyl |
| 2-138 | heptafluoroisopropyl | Me | Me | Me | 4-fluorophenyl |
| 2-139 | heptafluoroisopropyl | Me | Me | Me | 6-(trifluoromethyl)pyridin-3-yl |
| 2-140 | heptafluoroisopropyl | Me | Me | Me | 4-cyanophenyl |
| 2-141 | nonafluoro-s-butyl | Br | Me | H | phenyl |
| 2-142 | nonafluoro-s-butyl | I | Me | H | phenyl |
| 2-143 | nonafluoro-s-butyl | Br | Me | Me | phenyl |
| 2-144 | nonafluoro-s-butyl | I | Me | Me | phenyl |
| 2-145 | nonafluoro-s-butyl | Br | Me | H | 4-fluorophenyl |
| 2-146 | nonafluoro-s-butyl | I | Me | H | 4-fluorophenyl |
| 2-147 | nonafluoro-s-butyl | Br | Me | Me | 4-fluorophenyl |
| 2-148 | nonafluoro-s-butyl | I | Me | Me | 4-fluorophenyl |

TABLE 28

| Compound No. | R¹ | X¹ | X² | R⁴ | Q |
|---|---|---|---|---|---|
| 2-149 | nonafluoro-s-butyl | Br | Me | H | 6-(trifluoromethyl)pyridin-3-yl |
| 2-150 | nonafluoro-s-butyl | I | Me | H | 6-(trifluoromethyl)pyridin-3-yl |
| 2-151 | nonafluoro-s-butyl | Br | Me | Me | 6-(trifluoromethyl)pyridin-3-yl |
| 2-152 | nonafluoro-s-butyl | I | Me | Me | 6-(trifluoromethyl)pyridin-3-yl |
| 2-153 | nonafluoro-s-butyl | Br | CF₃ | H | phenyl |
| 2-154 | nonafluoro-s-butyl | I | CF₃ | H | phenyl |
| 2-155 | nonafluoro-s-butyl | Br | CF₃ | Me | phenyl |
| 2-156 | nonafluoro-s-butyl | I | CF₃ | Me | phenyl |

TABLE 28-continued

| Compound No. | R¹ | X¹ | X² | R⁴ | Q |
|---|---|---|---|---|---|
| 2-157 | nonafluoro-s-butyl | Br | CF₃ | H | 4-fluorophenyl |
| 2-158 | nonafluoro-s-butyl | I | CF₃ | H | 4-fluorophenyl |
| 2-159 | nonafluoro-s-butyl | Br | CF₃ | Me | 4-fluorophenyl |
| 2-160 | nonafluoro-s-butyl | I | CF₃ | Me | 4-fluorophenyl |
| 2-161 | nonafluoro-s-butyl | Br | CF₃ | H | 6-(trifluoromethyl)pyridin-3-yl |
| 2-162 | nonafluoro-s-butyl | I | CF₃ | H | 6-(trifluoromethyl)pyridin-3-yl |
| 2-163 | nonafluoro-s-butyl | Br | CF₃ | Me | 6-(trifluoromethyl)pyridin-3-yl |
| 2-164 | nonafluoro-s-butyl | I | CF₃ | Me | 6-(trifluoromethyl)pyridin-3-yl |
| 2-165 | nonafluoro-s-butyl | Cl | Cl | H | phenyl |
| 2-166 | nonafluoro-s-butyl | Cl | Cl | Me | phenyl |
| 2-167 | nonafluoro-s-butyl | Br | Br | H | phenyl |
| 2-168 | nonafluoro-s-butyl | Br | Br | Me | phenyl |
| 2-169 | nonafluoro-s-butyl | I | I | H | phenyl |
| 2-170 | nonafluoro-s-butyl | I | I | Me | phenyl |
| 2-171 | nonafluoro-s-butyl | Cl | Cl | H | 4-fluorophenyl |
| 2-172 | nonafluoro-s-butyl | Cl | Cl | Me | 4-fluorophenyl |
| 2-173 | nonafluoro-s-butyl | Br | Br | H | 4-fluorophenyl |
| 2-174 | nonafluoro-s-butyl | Br | Br | Me | 4-fluorophenyl |
| 2-175 | nonafluoro-s-butyl | I | I | H | 4-fluorophenyl |
| 2-176 | nonafluoro-s-butyl | I | I | Me | 4-fluorophenyl |
| 2-177 | nonafluoro-s-butyl | Cl | Cl | H | 6-(trifluoromethyl)pyridin-3-yl |
| 2-178 | nonafluoro-s-butyl | Cl | Cl | Me | 6-(trifluoromethyl)pyridin-3-yl |
| 2-179 | nonafluoro-s-butyl | Br | Br | H | 6-(trifluoromethyl)pyridin-3-yl |
| 2-180 | nonafluoro-s-butyl | Br | Br | Me | 6-(trifluoromethyl)pyridin-3-yl |
| 2-181 | nonafluoro-s-butyl | I | I | H | 6-(trifluoromethyl)pyridin-3-yl |
| 2-182 | nonafluoro-s-butyl | I | I | Me | 6-(trifluoromethyl)pyridin-3-yl |
| 2-183 | heptafluoroisopropyl | Cl | Br | Me | phenyl |
| 2-184 | heptafluoroisopropyl | Cl | Br | Me | 4-pyridyl |
| 2-185 | heptafluoroisopropyl | Cl | Br | Me | 3-pyridyl |
| 2-186 | heptafluoroisopropyl | Cl | Br | Me | 2-pyridyl |
| 2-187 | heptafluoroisopropyl | Cl | Br | Me | 4-cyanophenyl |
| 2-188 | heptafluoroisopropyl | Cl | Br | Et | phenyl |

TABLE 29

| Compound No. | R¹ | X¹ | X² | R⁴ | Q |
|---|---|---|---|---|---|
| 2-189 | heptafluoroisopropyl | Cl | Br | Et | 4-pyridyl |
| 2-190 | heptafluoroisopropyl | Cl | Br | Et | 3-pyridyl |
| 2-191 | heptafluoroisopropyl | Cl | Br | Et | 2-pyridyl |
| 2-192 | heptafluoroisopropyl | Cl | Br | Me | 4-cyanophenyl |
| 2-193 | heptafluoroisopropyl | Et | Br | Me | phenyl |
| 2-194 | heptafluoroisopropyl | Et | Br | Me | 4-pyridyl |
| 2-195 | heptafluoroisopropyl | Et | Br | Me | 3-pyridyl |
| 2-196 | heptafluoroisopropyl | Et | Br | Me | 2-pyridyl |
| 2-197 | heptafluoroisopropyl | Cl | Br | Me | 4-cyanophenyl |
| 2-198 | heptafluoroisopropyl | Et | Br | Et | phenyl |
| 2-199 | heptafluoroisopropyl | Et | Br | Et | 4-pyridyl |
| 2-200 | heptafluoroisopropyl | Et | Br | Et | 3-pyridyl |
| 2-201 | heptafluoroisopropyl | Et | Br | Et | 2-pyridyl |
| 2-202 | heptafluoroisopropyl | Cl | Br | Me | 4-cyanophenyl |
| 2-203 | heptafluoroisopropyl | Br | Br | Me | phenyl |
| 2-204 | heptafluoroisopropyl | Br | Br | Me | 4-pyridyl |
| 2-205 | heptafluoroisopropyl | Br | Br | Me | 3-pyridyl |
| 2-206 | heptafluoroisopropyl | Br | Br | Me | 2-pyridyl |
| 2-207 | heptafluoroisopropyl | Br | Br | Me | 4-cyanophenyl |
| 2-208 | heptafluoroisopropyl | Br | Br | Et | phenyl |
| 2-209 | heptafluoroisopropyl | Br | Br | Et | 4-pyridyl |
| 2-210 | heptafluoroisopropyl | Br | Br | Et | 3-pyridyl |
| 2-211 | heptafluoroisopropyl | Br | Br | Et | 2-pyridyl |
| 2-212 | heptafluoroisopropyl | Br | Br | Me | 4-cyanophenyl |
| 2-213 | heptafluoroisopropyl | Br | Br | Me | phenyl |
| 2-214 | heptafluoroisopropyl | Br | Br | Me | 4-pyridyl |
| 2-215 | heptafluoroisopropyl | Br | Br | Me | 3-pyridyl |
| 2-216 | heptafluoroisopropyl | Br | Br | Me | 2-pyridyl |
| 2-217 | heptafluoroisopropyl | Br | Br | Me | 4-cyanophenyl |
| 2-218 | heptafluoroisopropyl | Br | Br | Et | phenyl |
| 2-219 | heptafluoroisopropyl | Br | Br | Et | 4-pyridyl |
| 2-220 | heptafluoroisopropyl | Br | Br | Et | 3-pyridyl |
| 2-221 | heptafluoroisopropyl | Br | Br | Et | 2-pyridyl |
| 2-222 | heptafluoroisopropyl | Br | Br | Me | 4-cyanophenyl |
| 2-223 | heptafluoroisopropyl | Br | Br | H | N-ethyl-N-methylaminocarbonyl |
| 2-224 | heptafluoroisopropyl | Br | Br | Me | N-ethyl-N-methylaminocarbonyl |
| 2-225 | heptafluoroisopropyl | Br | difluoromethoxy | H | N-ethyl-N-methylaminocarbonyl |

TABLE 29-continued

| Compound No. | R¹ | X¹ | X² | R⁴ | Q |
|---|---|---|---|---|---|
| 2-226 | heptafluoroisopropyl | Br | difluoromethoxy | Me | N-ethyl-N-methylaminocarbonyl |
| 2-227 | heptafluoroisopropyl | Me | difluoromethoxy | H | N-ethyl-N-methylaminocarbonyl |
| 2-228 | heptafluoroisopropyl | Me | difluoromethoxy | Me | N-ethyl-N-methylaminocarbonyl |

TABLE 30

| Compound No. | R¹ | X¹ | X² | R⁴ | Q |
|---|---|---|---|---|---|
| 2-229 | heptafluoroisopropyl | Me | Et | H | N-ethyl-N-methylaminocarbonyl |
| 2-230 | heptafluoroisopropyl | Me | Et | Me | N-ethyl-N-methylaminocarbonyl |
| 2-231 | heptafluoroisopropyl | Br | Br | H | N-(2,2,2-trifluoroethyl)-N-methylaminocarbonyl |
| 2-232 | heptafluoroisopropyl | Br | Br | Me | N-(2,2,2-trifluoroethyl)-N-methylaminocarbonyl |
| 2-233 | heptafluoroisopropyl | Br | difluoromethoxy | H | N-(2,2,2-trifluoroethyl)-N-methylaminocarbonyl |
| 2-234 | heptafluoroisopropyl | Br | difluoromethoxy | Me | N-(2,2,2-trifluoroethyl)-N-methylaminocarbonyl |
| 2-235 | heptafluoroisopropyl | Me | difluoromethoxy | H | N-(2,2,2-trifluoroethyl)-N-methylaminocarbonyl |
| 2-236 | heptafluoroisopropyl | Me | difluoromethoxy | Me | N-(2,2,2-trifluoroethyl)-N-methylaminocarbonyl |
| 2-237 | heptafluoroisopropyl | Me | Et | H | N-(2,2,2-trifluoroethyl)-N-methylaminocarbonyl |
| 2-238 | heptafluoroisopropyl | Me | Et | Me | N-(2,2,2-trifluoroethyl)-N-methylaminocarbonyl |
| 2-239 | Br | heptafluoroisopropyl | $CF_3$ | H | phenyl |
| 2-240 | Br | heptafluoroisopropyl | $CF_3$ | Me | phenyl |
| 2-241 | Br | heptafluoroisopropyl | $CF_3$ | H | 4-fluorophenyl |
| 2-242 | Br | heptafluoroisopropyl | $CF_3$ | Me | 4-fluorophenyl |
| 2-243 | Br | heptafluoroisopropyl | $CF_3$ | H | 6-(trifluoromethyl)pyridin-3-yl |
| 2-244 | Br | heptafluoroisopropyl | $CF_3$ | Me | 6-(trifluoromethyl)pyridin-3-yl |
| 2-245 | heptafluoroisopropyl | heptafluoroisopropyl | $CF_3$ | H | phenyl |
| 2-246 | heptafluoroisopropyl | heptafluoroisopropyl | $CF_3$ | Me | phenyl |
| 2-247 | heptafluoroisopropyl | heptafluoroisopropyl | $CF_3$ | H | 4-fluorophenyl |
| 2-248 | heptafluoroisopropyl | heptafluoroisopropyl | $CF_3$ | Me | 4-fluorophenyl |
| 2-249 | heptafluoroisopropyl | heptafluoroisopropyl | $CF_3$ | H | 6-(trifluoromethyl)pyridin-3-yl |
| 2-250 | heptafluoroisopropyl | heptafluoroisopropyl | $CF_3$ | Me | 6-(trifluoromethyl)pyridin-3-yl |

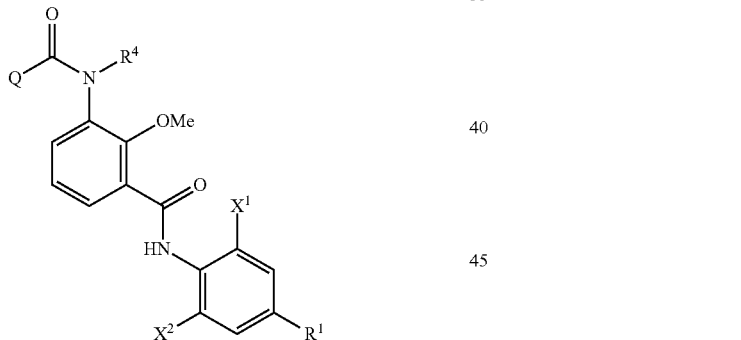

TABLE 31

| Compound No. | R¹ | X¹ | X² | R⁴ | Q |
|---|---|---|---|---|---|
| 2-251 | heptafluoroisopropyl | Br | Me | H | phenyl |
| 2-252 | heptafluoroisopropyl | I | Me | H | phenyl |
| 2-253 | heptafluoroisopropyl | Br | Me | Me | phenyl |
| 2-254 | heptafluoroisopropyl | I | Me | Me | phenyl |
| 2-255 | heptafluoroisopropyl | Br | Me | H | 4-fluorophenyl |
| 2-256 | heptafluoroisopropyl | I | Me | H | 4-fluorophenyl |
| 2-257 | heptafluoroisopropyl | Br | Me | Me | 4-fluorophenyl |
| 2-258 | heptafluoroisopropyl | I | Me | Me | 4-fluorophenyl |
| 2-259 | heptafluoroisopropyl | Br | Me | H | 6-(trifluoromethyl)pyridin-3-yl |
| 2-260 | heptafluoroisopropyl | I | Me | H | 6-(trifluoromethyl)pyridin-3-yl |
| 2-261 | heptafluoroisopropyl | Br | Me | Me | 6-(trifluoromethyl)pyridin-3-yl |
| 2-262 | heptafluoroisopropyl | I | Me | Me | 6-(trifluoromethyl)pyridin-3-yl |
| 2-263 | heptafluoroisopropyl | Br | $CF_3$ | H | phenyl |
| 2-264 | heptafluoroisopropyl | I | $CF_3$ | H | phenyl |
| 2-265 | heptafluoroisopropyl | Br | $CF_3$ | Me | phenyl |

TABLE 31-continued

| Compound No. | R¹ | X¹ | X² | R⁴ | Q |
|---|---|---|---|---|---|
| 2-266 | heptafluoroisopropyl | I | CF₃ | Me | phenyl |
| 2-267 | heptafluoroisopropyl | Br | CF₃ | H | 4-fluorophenyl |
| 2-268 | heptafluoroisopropyl | I | CF₃ | H | 4-fluorophenyl |
| 2-269 | heptafluoroisopropyl | Br | CF₃ | Me | 4-fluorophenyl |
| 2-270 | heptafluoroisopropyl | I | CF₃ | Me | 4-fluorophenyl |
| 2-271 | heptafluoroisopropyl | Br | CF₃ | H | 6-(trifluoromethyl)pyridin-3-yl |
| 2-272 | heptafluoroisopropyl | I | CF₃ | H | 6-(trifluoromethyl)pyridin-3-yl |
| 2-273 | heptafluoroisopropyl | Br | CF₃ | Me | 6-(trifluoromethyl)pyridin-3-yl |
| 2-274 | heptafluoroisopropyl | I | CF₃ | Me | 6-(trifluoromethyl)pyridin-3-yl |
| 2-275 | heptafluoroisopropyl | Me | Me | Me | phenyl |
| 2-276 | heptafluoroisopropyl | Me | Me | Me | 4-fluorophenyl |
| 2-277 | heptafluoroisopropyl | Me | Me | Me | 6-(trifluoromethyl)pyridin-3-yl |
| 2-278 | heptafluoroisopropyl | Me | Me | Me | 4-cyanophenyl |
| 2-279 | nonafluoro-s-butyl | Br | Me | H | phenyl |
| 2-280 | nonafluoro-s-butyl | I | Me | H | phenyl |
| 2-281 | nonafluoro-s-butyl | Br | Me | Me | phenyl |
| 2-282 | nonafluoro-s-butyl | I | Me | Me | phenyl |
| 2-283 | nonafluoro-s-butyl | Br | Me | H | 4-fluorophenyl |
| 2-284 | nonafluoro-s-butyl | I | Me | H | 4-fluorophenyl |
| 2-285 | nonafluoro-s-butyl | Br | Me | Me | 4-fluorophenyl |
| 2-286 | nonafluoro-s-butyl | I | Me | Me | 4-fluorophenyl |
| 2-287 | nonafluoro-s-butyl | Br | Me | H | 6-(trifluoromethyl)pyridin-3-yl |
| 2-288 | nonafluoro-s-butyl | I | Me | H | 6-(trifluoromethyl)pyridin-3-yl |
| 2-289 | nonafluoro-s-butyl | Br | Me | Me | 6-(trifluoromethyl)pyridin-3-yl |
| 2-290 | nonafluoro-s-butyl | I | Me | Me | 6-(trifluoromethyl)pyridin-3-yl |

TABLE 32

| Compound No. | R¹ | X¹ | X² | R⁴ | Q |
|---|---|---|---|---|---|
| 2-291 | nonafluoro-s-butyl | Br | CF₃ | H | phenyl |
| 2-292 | nonafluoro-s-butyl | I | CF₃ | H | phenyl |
| 2-293 | nonafluoro-s-butyl | Br | CF₃ | Me | phenyl |
| 2-294 | nonafluoro-s-butyl | I | CF₃ | Me | phenyl |
| 2-295 | nonafluoro-s-butyl | Br | CF₃ | H | 4-fluorophenyl |
| 2-296 | nonafluoro-s-butyl | I | CF₃ | H | 4-fluorophenyl |
| 2-297 | nonafluoro-s-butyl | Br | CF₃ | Me | 4-fluorophenyl |
| 2-298 | nonafluoro-s-butyl | I | CF₃ | Me | 4-fluorophenyl |
| 2-299 | nonafluoro-s-butyl | Br | CF₃ | H | 6-(trifluoromethyl)pyridin-3-yl |
| 2-300 | nonafluoro-s-butyl | I | CF₃ | H | 6-(trifluoromethyl)pyridin-3-yl |
| 2-301 | nonafluoro-s-butyl | Br | CF₃ | Me | 6-(trifluoromethyl)pyridin-3-yl |
| 2-302 | nonafluoro-s-butyl | I | CF₃ | Me | 6-(trifluoromethyl)pyridin-3-yl |
| 2-303 | heptafluoroisopropyl | Cl | Br | Me | phenyl |
| 2-304 | heptafluoroisopropyl | Cl | Br | Me | 4-pyridyl |
| 2-305 | heptafluoroisopropyl | Cl | Br | Me | 3-pyridyl |
| 2-306 | heptafluoroisopropyl | Cl | Br | Me | 2-pyridyl |
| 2-307 | heptafluoroisopropyl | Cl | Br | Me | 4-cyanophenyl |
| 2-308 | heptafluoroisopropyl | Cl | Br | Et | phenyl |
| 2-309 | heptafluoroisopropyl | Cl | Br | Et | 4-pyridyl |
| 2-310 | heptafluoroisopropyl | Cl | Br | Et | 3-pyridyl |
| 2-311 | heptafluoroisopropyl | Cl | Br | Et | 2-pyridyl |
| 2-312 | heptafluoroisopropyl | Cl | Br | Me | 4-cyanophenyl |
| 2-313 | heptafluoroisopropyl | Et | Br | Me | phenyl |
| 2-314 | heptafluoroisopropyl | Et | Br | Me | 4-pyridyl |
| 2-315 | heptafluoroisopropyl | Et | Br | Me | 3-pyridyl |
| 2-316 | heptafluoroisopropyl | Et | Br | Me | 2-pyridyl |
| 2-317 | heptafluoroisopropyl | Cl | Br | Me | 4-cyanophenyl |
| 2-318 | heptafluoroisopropyl | Et | Br | Et | phenyl |
| 2-319 | heptafluoroisopropyl | Et | Br | Et | 4-pyridyl |
| 2-320 | heptafluoroisopropyl | Et | Br | Et | 3-pyridyl |
| 2-321 | heptafluoroisopropyl | Et | Br | Et | 2-pyridyl |
| 2-322 | heptafluoroisopropyl | Cl | Br | Me | 4-cyanophenyl |
| 2-323 | heptafluoroisopropyl | Br | Br | Me | phenyl |
| 2-324 | heptafluoroisopropyl | Br | Br | Me | 4-pyridyl |
| 2-325 | heptafluoroisopropyl | Br | Br | Me | 3-pyridyl |
| 2-326 | heptafluoroisopropyl | Br | Br | Me | 2-pyridyl |
| 2-327 | heptafluoroisopropyl | Br | Br | Me | 4-cyanophenyl |
| 2-328 | heptafluoroisopropyl | Br | Br | Et | phenyl |
| 2-329 | heptafluoroisopropyl | Br | Br | Et | 4-pyridyl |
| 2-330 | heptafluoroisopropyl | Br | Br | Et | 3-pyridyl |

TABLE 33

| Compound No. | R¹ | X¹ | X² | R⁴ | Q |
|---|---|---|---|---|---|
| 2-331 | heptafluoroisopropyl | Br | Br | Et | 2-pyridyl |
| 2-332 | heptafluoroisopropyl | Br | Br | Me | 4-cyanophenyl |
| 2-333 | heptafluoroisopropyl | Br | Br | Me | phenyl |
| 2-334 | heptafluoroisopropyl | Br | Br | Me | 4-pyridyl |
| 2-335 | heptafluoroisopropyl | Br | Br | Me | 3-pyridyl |
| 2-336 | heptafluoroisopropyl | Br | Br | Me | 2-pyridyl |
| 2-337 | heptafluoroisopropyl | Br | Br | Me | 4-cyanophenyl |
| 2-338 | heptafluoroisopropyl | Br | Br | Et | phenyl |
| 2-339 | heptafluoroisopropyl | Br | Br | Et | 4-pyridyl |
| 2-340 | heptafluoroisopropyl | Br | Br | Et | 3-pyridyl |
| 2-341 | heptafluoroisopropyl | Br | Br | Et | 2-pyridyl |
| 2-342 | heptafluoroisopropyl | Br | Br | Me | 4-cyanophenyl |
| 2-343 | heptafluoroisopropyl | Br | Br | H | N-ethyl-N-methylaminocarbonyl |
| 2-344 | heptafluoroisopropyl | Br | Br | Me | N-ethyl-N-methylaminocarbonyl |
| 2-345 | heptafluoroisopropyl | Br | difluoromethoxy | H | N-ethyl-N-methylaminocarbonyl |
| 2-346 | heptafluoroisopropyl | Br | difluoromethoxy | Me | N-ethyl-N-methylaminocarbonyl |
| 2-347 | heptafluoroisopropyl | Me | difluoromethoxy | H | N-ethyl-N-methylaminocarbonyl |
| 2-348 | heptafluoroisopropyl | Me | difluoromethoxy | Me | N-ethyl-N-methylaminocarbonyl |
| 2-349 | heptafluoroisopropyl | Me | Et | H | N-ethyl-N-methylaminocarbonyl |
| 2-350 | heptafluoroisopropyl | Me | Et | Me | N-ethyl-N-methylaminocarbonyl |
| 2-351 | heptafluoroisopropyl | Br | Br | H | N-(2,2,2-trifluoroethyl)-N-methylaminocarbonyl |
| 2-352 | heptafluoroisopropyl | Br | Br | Me | N-(2,2,2-trifluoroethyl)-N-methylaminocarbonyl |
| 2-353 | heptafluoroisopropyl | Br | difluoromethoxy | H | N-(2,2,2-trifluoroethyl)-N-methylaminocarbonyl |
| 2-354 | heptafluoroisopropyl | Br | difluoromethoxy | Me | N-(2,2,2-trifluoroethyl)-N-methylaminocarbonyl |
| 2-355 | heptafluoroisopropyl | Me | difluoromethoxy | H | N-(2,2,2-trifluoroethyl)-N-methylaminocarbonyl |
| 2-356 | heptafluoroisopropyl | Me | difluoromethoxy | Me | N-(2,2,2-trifluoroethyl)-N-methylaminocarbonyl |
| 2-357 | heptafluoroisopropyl | Me | Et | H | N-(2,2,2-trifluoroethyl)-N-methylaminocarbonyl |
| 2-358 | heptafluoroisopropyl | Me | Et | Me | N-(2,2,2-trifluoroethyl)-N-methylaminocarbonyl |

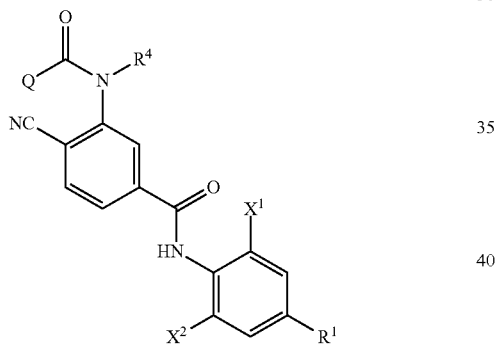

TABLE 34

| Compound No. | R¹ | X¹ | X² | R⁴ | Q |
|---|---|---|---|---|---|
| 2-359 | heptafluoroisopropyl | Br | Me | H | phenyl |
| 2-360 | heptafluoroisopropyl | I | Me | H | phenyl |
| 2-361 | heptafluoroisopropyl | Br | Me | Me | phenyl |
| 2-362 | heptafluoroisopropyl | I | Me | Me | phenyl |
| 2-363 | heptafluoroisopropyl | Br | Me | H | 4-fluorophenyl |
| 2-364 | heptafluoroisopropyl | I | Me | H | 4-fluorophenyl |
| 2-365 | heptafluoroisopropyl | Br | Me | Me | 4-fluorophenyl |
| 2-366 | heptafluoroisopropyl | I | Me | Me | 4-fluorophenyl |
| 2-367 | heptafluoroisopropyl | Br | Me | H | 6-(trifluoromethyl)pyridin-3-yl |
| 2-368 | heptafluoroisopropyl | I | Me | H | 6-(trifluoromethyl)pyridin-3-yl |
| 2-369 | heptafluoroisopropyl | Br | Me | Me | 6-(trifluoromethyl)pyridin-3-yl |
| 2-370 | heptafluoroisopropyl | I | Me | Me | 6-(trifluoromethyl)pyridin-3-yl |
| 2-371 | heptafluoroisopropyl | Br | CF₃ | H | phenyl |
| 2-372 | heptafluoroisopropyl | I | CF₃ | H | phenyl |
| 2-373 | heptafluoroisopropyl | Br | CF₃ | Me | phenyl |
| 2-374 | heptafluoroisopropyl | I | CF₃ | Me | phenyl |
| 2-375 | heptafluoroisopropyl | Br | CF₃ | H | 4-fluorophenyl |
| 2-376 | heptafluoroisopropyl | I | CF₃ | H | 4-fluorophenyl |
| 2-377 | heptafluoroisopropyl | Br | CF₃ | Me | 4-fluorophenyl |
| 2-378 | heptafluoroisopropyl | I | CF₃ | Me | 4-fluorophenyl |

TABLE 34-continued

| Compound No. | R¹ | X¹ | X² | R⁴ | Q |
|---|---|---|---|---|---|
| 2-379 | heptafluoroisopropyl | Br | CF₃ | H | 6-(trifluoromethyl)pyridin-3-yl |
| 2-380 | heptafluoroisopropyl | I | CF₃ | H | 6-(trifluoromethyl)pyridin-3-yl |
| 2-381 | heptafluoroisopropyl | Br | CF₃ | Me | 6-(trifluoromethyl)pyridin-3-yl |
| 2-382 | heptafluoroisopropyl | I | CF₃ | Me | 6-(trifluoromethyl)pyridin-3-yl |
| 2-383 | heptafluoroisopropyl | Me | Me | Me | phenyl |
| 2-384 | heptafluoroisopropyl | Me | Me | Me | 4-fluorophenyl |
| 2-385 | heptafluoroisopropyl | Me | Me | Me | 6-(trifluoromethyl)pyridin-3-yl |
| 2-386 | heptafluoroisopropyl | Me | Me | Me | 4-cyanophenyl |
| 2-387 | nonafluoro-s-butyl | Br | Me | H | phenyl |
| 2-388 | nonafluoro-s-butyl | I | Me | H | phenyl |
| 2-389 | nonafluoro-s-butyl | Br | Me | Me | phenyl |
| 2-390 | nonafluoro-s-butyl | I | Me | Me | phenyl |
| 2-391 | nonafluoro-s-butyl | Br | Me | H | 4-fluorophenyl |
| 2-392 | nonafluoro-s-butyl | I | Me | H | 4-fluorophenyl |
| 2-393 | nonafluoro-s-butyl | Br | Me | Me | 4-fluorophenyl |
| 2-394 | nonafluoro-s-butyl | I | Me | Me | 4-fluorophenyl |
| 2-395 | nonafluoro-s-butyl | Br | Me | H | 6-(trifluoromethyl)pyridin-3-yl |
| 2-396 | nonafluoro-s-butyl | I | Me | H | 6-(trifluoromethyl)pyridin-3-yl |
| 2-397 | nonafluoro-s-butyl | Br | Me | Me | 6-(trifluoromethyl)pyridin-3-yl |
| 2-398 | nonafluoro-s-butyl | I | Me | Me | 6-(trifluoromethyl)pyridin-3-yl |

TABLE 35

| Compound No. | R¹ | X¹ | X² | R⁴ | Q |
|---|---|---|---|---|---|
| 2-399 | nonafluoro-s-butyl | Br | CF₃ | H | phenyl |
| 2-400 | nonafluoro-s-butyl | I | CF₃ | H | phenyl |
| 2-401 | nonafluoro-s-butyl | Br | CF₃ | Me | phenyl |
| 2-402 | nonafluoro-s-butyl | I | CF₃ | Me | phenyl |
| 2-403 | nonafluoro-s-butyl | Br | CF₃ | H | 4-fluorophenyl |
| 2-404 | nonafluoro-s-butyl | I | CF₃ | H | 4-fluorophenyl |
| 2-405 | nonafluoro-s-butyl | Br | CF₃ | Me | 4-fluorophenyl |
| 2-406 | nonafluoro-s-butyl | I | CF₃ | Me | 4-fluorophenyl |
| 2-407 | nonafluoro-s-butyl | Br | CF₃ | H | 6-(trifluoromethyl)pyridin-3-yl |
| 2-408 | nonafluoro-s-butyl | I | CF₃ | H | 6-(trifluoromethyl)pyridin-3-yl |
| 2-409 | nonafluoro-s-butyl | Br | CF₃ | Me | 6-(trifluoromethyl)pyridin-3-yl |
| 2-410 | nonafluoro-s-butyl | I | CF₃ | Me | 6-(trifluoromethyl)pyridin-3-yl |
| 2-411 | heptafluoroisopropyl | Cl | Br | Me | phenyl |
| 2-412 | heptafluoroisopropyl | Cl | Br | Me | 4-pyridyl |
| 2-413 | heptafluoroisopropyl | Cl | Br | Me | 3-pyridyl |
| 2-414 | heptafluoroisopropyl | Cl | Br | Me | 2-pyridyl |
| 2-415 | heptafluoroisopropyl | Cl | Br | Me | 4-cyanophenyl |
| 2-416 | heptafluoroisopropyl | Cl | Br | Et | phenyl |
| 2-417 | heptafluoroisopropyl | Cl | Br | Et | 4-pyridyl |
| 2-418 | heptafluoroisopropyl | Cl | Br | Et | 3-pyridyl |
| 2-419 | heptafluoroisopropyl | Cl | Br | Et | 2-pyridyl |
| 2-420 | heptafluoroisopropyl | Cl | Br | Me | 4-cyanophenyl |
| 2-421 | heptafluoroisopropyl | Et | Br | Me | phenyl |
| 2-422 | heptafluoroisopropyl | Et | Br | Me | 4-pyridyl |
| 2-423 | heptafluoroisopropyl | Et | Br | Me | 3-pyridyl |
| 2-424 | heptafluoroisopropyl | Et | Br | Me | 2-pyridyl |
| 2-425 | heptafluoroisopropyl | Cl | Br | Me | 4-cyanophenyl |
| 2-426 | heptafluoroisopropyl | Et | Br | Et | phenyl |
| 2-427 | heptafluoroisopropyl | Et | Br | Et | 4-pyridyl |
| 2-428 | heptafluoroisopropyl | Et | Br | Et | 3-pyridyl |
| 2-429 | heptafluoroisopropyl | Et | Br | Et | 2-pyridyl |
| 2-430 | heptafluoroisopropyl | Cl | Br | Me | 4-cyanophenyl |
| 2-431 | heptafluoroisopropyl | Br | Br | Me | phenyl |
| 2-432 | heptafluoroisopropyl | Br | Br | Me | 4-pyridyl |
| 2-433 | heptafluoroisopropyl | Br | Br | Me | 3-pyridyl |
| 2-434 | heptafluoroisopropyl | Br | Br | Me | 2-pyridyl |
| 2-435 | heptafluoroisopropyl | Br | Br | Me | 4-cyanophenyl |
| 2-436 | heptafluoroisopropyl | Br | Br | Et | phenyl |
| 2-437 | heptafluoroisopropyl | Br | Br | Et | 4-pyridyl |
| 2-438 | heptafluoroisopropyl | Br | Br | Et | 3-pyridyl |

TABLE 36

| Compound No. | R¹ | X¹ | X² | R⁴ | Q |
|---|---|---|---|---|---|
| 2-439 | heptafluoroisopropyl | Br | Br | Et | 2-pyridyl |
| 2-440 | heptafluoroisopropyl | Br | Br | Me | 4-cyanophenyl |
| 2-441 | heptafluoroisopropyl | Br | Br | Me | phenyl |
| 2-442 | heptafluoroisopropyl | Br | Br | Me | 4-pyridyl |
| 2-443 | heptafluoroisopropyl | Br | Br | Me | 3-pyridyl |
| 2-444 | heptafluoroisopropyl | Br | Br | Me | 2-pyridyl |
| 2-445 | heptafluoroisopropyl | Br | Br | Me | 4-cyanophenyl |
| 2-446 | heptafluoroisopropyl | Br | Br | Et | phenyl |
| 2-447 | heptafluoroisopropyl | Br | Br | Et | 4-pyridyl |
| 2-448 | heptafluoroisopropyl | Br | Br | Et | 3-pyridyl |
| 2-449 | heptafluoroisopropyl | Br | Br | Et | 2-pyridyl |
| 2-450 | heptafluoroisopropyl | Br | Br | Me | 4-cyanophenyl |
| 2-451 | heptafluoroisopropyl | Br | Br | H | N-ethyl-N-methylaminocarbonyl |
| 2-452 | heptafluoroisopropyl | Br | Br | Me | N-ethyl-N-methylaminocarbonyl |
| 2-453 | heptafluoroisopropyl | Br | difluoromethoxy | H | N-ethyl-N-methylaminocarbonyl |
| 2-454 | heptafluoroisopropyl | Br | difluoromethoxy | Me | N-ethyl-N-methylaminocarbonyl |
| 2-455 | heptafluoroisopropyl | Me | difluoromethoxy | H | N-ethyl-N-methylaminocarbonyl |
| 2-456 | heptafluoroisopropyl | Me | difluoromethoxy | Me | N-ethyl-N-methylaminocarbonyl |
| 2-457 | heptafluoroisopropyl | Me | Et | H | N-ethyl-N-methylaminocarbonyl |
| 2-458 | heptafluoroisopropyl | Me | Et | Me | N-ethyl-N-methylaminocarbonyl |
| 2-459 | heptafluoroisopropyl | Br | Br | H | N-(2,2,2-trifluoroethyl)-N-methylaminocarbonyl |
| 2-460 | heptafluoroisopropyl | Br | Br | Me | N-(2,2,2-trifluoroethyl)-N-methylaminocarbonyl |
| 2-461 | heptafluoroisopropyl | Br | difluoromethoxy | H | N-(2,2,2-trifluoroethyl)-N-methylaminocarbonyl |
| 2-462 | heptafluoroisopropyl | Br | difluoromethoxy | Me | N-(2,2,2-trifluoroethyl)-N-methylaminocarbonyl |
| 2-463 | heptafluoroisopropyl | Me | difluoromethoxy | H | N-(2,2,2-trifluoroethyl)-N-methylaminocarbonyl |
| 2-464 | heptafluoroisopropyl | Me | difluoromethoxy | Me | N-(2,2,2-trifluoroethyl)-N-methylaminocarbonyl |
| 2-465 | heptafluoroisopropyl | Me | Et | H | N-(2,2,2-trifluoroethyl)-N-methylaminocarbonyl |
| 2-466 | heptafluoroisopropyl | Me | Et | Me | N-(2,2,2-trifluoroethyl)-N-methylaminocarbonyl |

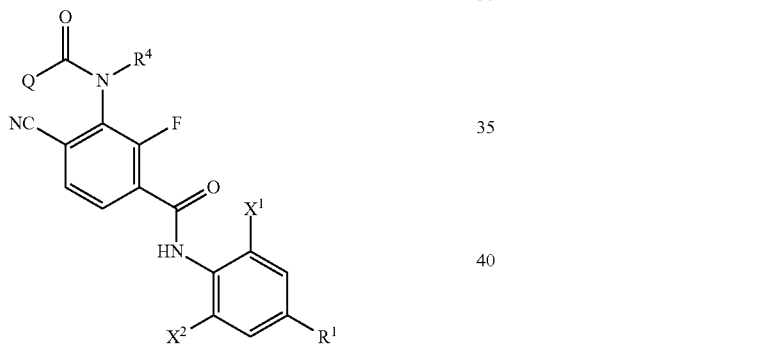

TABLE 37

| Compound No. | R¹ | X¹ | X² | R⁴ | Q |
|---|---|---|---|---|---|
| 2-467 | heptafluoroisopropyl | Br | Me | H | phenyl |
| 2-468 | heptafluoroisopropyl | I | Me | H | phenyl |
| 2-469 | heptafluoroisopropyl | Br | Me | Me | phenyl |
| 2-470 | heptafluoroisopropyl | I | Me | Me | phenyl |
| 2-471 | heptafluoroisopropyl | Br | Me | H | 4-fluorophenyl |
| 2-472 | heptafluoroisopropyl | I | Me | H | 4-fluorophenyl |
| 2-473 | heptafluoroisopropyl | Br | Me | Me | 4-fluorophenyl |
| 2-474 | heptafluoroisopropyl | I | Me | Me | 4-fluorophenyl |
| 2-475 | heptafluoroisopropyl | Br | Me | H | 6-(trifluoromethyl)pyridin-3-yl |
| 2-476 | heptafluoroisopropyl | I | Me | H | 6-(trifluoromethyl)pyridin-3-yl |
| 2-477 | heptafluoroisopropyl | Br | Me | Me | 6-(trifluoromethyl)pyridin-3-yl |
| 2-478 | heptafluoroisopropyl | I | Me | Me | 6-(trifluoromethyl)pyridin-3-yl |
| 2-479 | heptafluoroisopropyl | Br | CF₃ | H | phenyl |
| 2-480 | heptafluoroisopropyl | I | CF₃ | H | phenyl |
| 2-481 | heptafluoroisopropyl | Br | CF₃ | Me | phenyl |
| 2-482 | heptafluoroisopropyl | I | CF₃ | Me | phenyl |
| 2-483 | heptafluoroisopropyl | Br | CF₃ | H | 4-fluorophenyl |
| 2-484 | heptafluoroisopropyl | I | CF₃ | H | 4-fluorophenyl |
| 2-485 | heptafluoroisopropyl | Br | CF₃ | Me | 4-fluorophenyl |
| 2-486 | heptafluoroisopropyl | I | CF₃ | Me | 4-fluorophenyl |

TABLE 37-continued

| Compound No. | R¹ | X¹ | X² | R⁴ | Q |
|---|---|---|---|---|---|
| 2-487 | heptafluoroisopropyl | Br | CF₃ | H | 6-(trifluoromethyl)pyridin-3-yl |
| 2-488 | heptafluoroisopropyl | I | CF₃ | H | 6-(trifluoromethyl)pyridin-3-yl |
| 2-489 | heptafluoroisopropyl | Br | CF₃ | Me | 6-(trifluoromethyl)pyridin-3-yl |
| 2-490 | heptafluoroisopropyl | I | CF₃ | Me | 6-(trifluoromethyl)pyridin-3-yl |
| 2-491 | heptafluoroisopropyl | Me | Me | Me | phenyl |
| 2-492 | heptafluoroisopropyl | Me | Me | Me | 4-fluorophenyl |
| 2-493 | heptafluoroisopropyl | Me | Me | Me | 6-(trifluoromethyl)pyridin-3-yl |
| 2-494 | heptafluoroisopropyl | Me | Me | Me | 4-cyanophenyl |
| 2-495 | nonafluoro-s-butyl | Br | Me | H | phenyl |
| 2-496 | nonafluoro-s-butyl | I | Me | H | phenyl |
| 2-497 | nonafluoro-s-butyl | Br | Me | Me | phenyl |
| 2-498 | nonafluoro-s-butyl | I | Me | Me | phenyl |
| 2-499 | nonafluoro-s-butyl | Br | Me | H | 4-fluorophenyl |
| 2-500 | nonafluoro-s-butyl | I | Me | H | 4-fluorophenyl |
| 2-501 | nonafluoro-s-butyl | Br | Me | Me | 4-fluorophenyl |
| 2-502 | nonafluoro-s-butyl | I | Me | Me | 4-fluorophenyl |
| 2-503 | nonafluoro-s-butyl | Br | Me | H | 6-(trifluoromethyl)pyridin-3-yl |
| 2-504 | nonafluoro-s-butyl | I | Me | H | 6-(trifluoromethyl)pyridin-3-yl |
| 2-505 | nonafluoro-s-butyl | Br | Me | Me | 6-(trifluoromethyl)pyridin-3-yl |
| 2-506 | nonafluoro-s-butyl | I | Me | Me | 6-(trifluoromethyl)pyridin-3-yl |

TABLE 38

| Compound No. | R¹ | X¹ | X² | R⁴ | Q |
|---|---|---|---|---|---|
| 2-507 | nonafluoro-s-butyl | Br | CF₃ | H | phenyl |
| 2-508 | nonafluoro-s-butyl | I | CF₃ | H | phenyl |
| 2-509 | nonafluoro-s-butyl | Br | CF₃ | Me | phenyl |
| 2-510 | nonafluoro-s-butyl | I | CF₃ | Me | phenyl |
| 2-511 | nonafluoro-s-butyl | Br | CF₃ | H | 4-fluorophenyl |
| 2-512 | nonafluoro-s-butyl | I | CF₃ | H | 4-fluorophenyl |
| 2-513 | nonafluoro-s-butyl | Br | CF₃ | Me | 4-fluorophenyl |
| 2-514 | nonafluoro-s-butyl | I | CF₃ | Me | 4-fluorophenyl |
| 2-515 | nonafluoro-s-butyl | Br | CF₃ | H | 6-(trifluoromethyl)pyridin-3-yl |
| 2-516 | nonafluoro-s-butyl | I | CF₃ | H | 6-(trifluoromethyl)pyridin-3-yl |
| 2-517 | nonafluoro-s-butyl | Br | CF₃ | Me | 6-(trifluoromethyl)pyridin-3-yl |
| 2-518 | nonafluoro-s-butyl | I | CF₃ | Me | 6-(trifluoromethyl)pyridin-3-yl |
| 2-519 | heptafluoroisopropyl | Cl | Br | Me | phenyl |
| 2-520 | heptafluoroisopropyl | Cl | Br | Me | 4-pyridyl |
| 2-521 | heptafluoroisopropyl | Cl | Br | Me | 3-pyridyl |
| 2-522 | heptafluoroisopropyl | Cl | Br | Me | 2-pyridyl |
| 2-523 | heptafluoroisopropyl | Cl | Br | Me | 4-cyanophenyl |
| 2-524 | heptafluoroisopropyl | Cl | Br | Et | phenyl |
| 2-525 | heptafluoroisopropyl | Cl | Br | Et | 4-pyridyl |
| 2-526 | heptafluoroisopropyl | Cl | Br | Et | 3-pyridyl |
| 2-527 | heptafluoroisopropyl | Cl | Br | Et | 2-pyridyl |
| 2-528 | heptafluoroisopropyl | Cl | Br | Me | 4-cyanophenyl |
| 2-529 | heptafluoroisopropyl | Et | Br | Me | phenyl |
| 2-530 | heptafluoroisopropyl | Et | Br | Me | 4-pyridyl |
| 2-531 | heptafluoroisopropyl | Et | Br | Me | 3-pyridyl |
| 2-532 | heptafluoroisopropyl | Et | Br | Me | 2-pyridyl |
| 2-533 | heptafluoroisopropyl | Cl | Br | Me | 4-cyanophenyl |
| 2-534 | heptafluoroisopropyl | Et | Br | Et | phenyl |
| 2-535 | heptafluoroisopropyl | Et | Br | Et | 4-pyridyl |
| 2-536 | heptafluoroisopropyl | Et | Br | Et | 3-pyridyl |
| 2-537 | heptafluoroisopropyl | Et | Br | Et | 2-pyridyl |
| 2-538 | heptafluoroisopropyl | Cl | Br | Me | 4-cyanophenyl |
| 2-539 | heptafluoroisopropyl | Br | Br | Me | phenyl |
| 2-540 | heptafluoroisopropyl | Br | Br | Me | 4-pyridyl |
| 2-541 | heptafluoroisopropyl | Br | Br | Me | 3-pyridyl |
| 2-542 | heptafluoroisopropyl | Br | Br | Me | 2-pyridyl |
| 2-543 | heptafluoroisopropyl | Br | Br | Me | 4-cyanophenyl |
| 2-544 | heptafluoroisopropyl | Br | Br | Et | phenyl |
| 2-545 | heptafluoroisopropyl | Br | Br | Et | 4-pyridyl |
| 2-546 | heptafluoroisopropyl | Br | Br | Et | 3-pyridyl |

TABLE 39

| Compound No. | R¹ | X¹ | X² | R⁴ | Q |
|---|---|---|---|---|---|
| 2-547 | heptafluoroisopropyl | Br | Br | Et | 2-pyridyl |
| 2-548 | heptafluoroisopropyl | Br | Br | Me | 4-cyanophenyl |
| 2-549 | heptafluoroisopropyl | Br | Br | Me | phenyl |
| 2-550 | heptafluoroisopropyl | Br | Br | Me | 4-pyridyl |
| 2-551 | heptafluoroisopropyl | Br | Br | Me | 3-pyridyl |
| 2-552 | heptafluoroisopropyl | Br | Br | Me | 2-pyridyl |
| 2-553 | heptafluoroisopropyl | Br | Br | Me | 4-cyanophenyl |
| 2-554 | heptafluoroisopropyl | Br | Br | Et | phenyl |
| 2-555 | heptafluoroisopropyl | Br | Br | Et | 4-pyridyl |
| 2-556 | heptafluoroisopropyl | Br | Br | Et | 3-pyridyl |
| 2-557 | heptafluoroisopropyl | Br | Br | Et | 2-pyridyl |
| 2-558 | heptafluoroisopropyl | Br | Br | Me | 4-cyanophenyl |
| 2-559 | heptafluoroisopropyl | Br | Br | H | N-ethyl-N-methylaminocarbonyl |
| 2-560 | heptafluoroisopropyl | Br | Br | Me | N-ethyl-N-methylaminocarbonyl |
| 2-561 | heptafluoroisopropyl | Br | difluoromethoxy | H | N-ethyl-N-methylaminocarbonyl |
| 2-562 | heptafluoroisopropyl | Br | difluoromethoxy | Me | N-ethyl-N-methylaminocarbonyl |
| 2-563 | heptafluoroisopropyl | Me | difluoromethoxy | H | N-ethyl-N-methylaminocarbonyl |
| 2-564 | heptafluoroisopropyl | Me | difluoromethoxy | Me | N-ethyl-N-methylaminocarbonyl |
| 2-565 | heptafluoroisopropyl | Me | Et | H | N-ethyl-N-methylaminocarbonyl |
| 2-566 | heptafluoroisopropyl | Me | Et | Me | N-ethyl-N-methylaminocarbonyl |
| 2-567 | heptafluoroisopropyl | Br | Br | H | N-(2,2,2-trifluoroethyl)-N-methylaminocarbonyl |
| 2-568 | heptafluoroisopropyl | Br | Br | Me | N-(2,2,2-trifluoroethyl)-N-methylaminocarbonyl |
| 2-569 | heptafluoroisopropyl | Br | difluoromethoxy | H | N-(2,2,2-trifluoroethyl)-N-methylaminocarbonyl |
| 2-570 | heptafluoroisopropyl | Br | difluoromethoxy | Me | N-(2,2,2-trifluoroethyl)-N-methylaminocarbonyl |
| 2-571 | heptafluoroisopropyl | Me | difluoromethoxy | H | N-(2,2,2-trifluoroethyl)-N-methylaminocarbonyl |
| 2-572 | heptafluoroisopropyl | Me | difluoromethoxy | Me | N-(2,2,2-trifluoroethyl)-N-methylaminocarbonyl |
| 2-573 | heptafluoroisopropyl | Me | Et | H | N-(2,2,2-trifluoroethyl)-N-methylaminocarbonyl |
| 2-574 | heptafluoroisopropyl | Me | Et | Me | N-(2,2,2-trifluoroethyl)-N-methylaminocarbonyl |

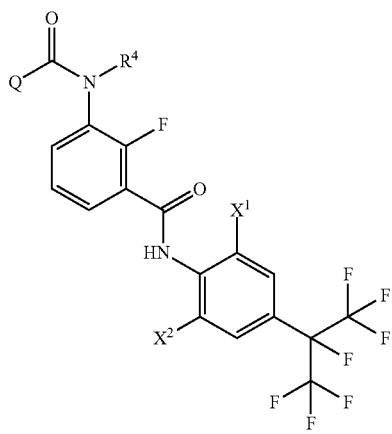

TABLE 40

| Compound No. | X¹ | X² | R⁴ | Q |
|---|---|---|---|---|
| 2-575 | CF₃ | Br | H | 4-nitrophenyl |
| 2-576 | CF₃ | I | H | 4-nitrophenyl |
| 2-577 | CF₃ | Br | Me | 4-nitrophenyl |
| 2-578 | CF₃ | I | Me | 4-nitrophenyl |
| 2-579 | CF₃ | Br | H | 3-fluorophenyl |
| 2-580 | CF₃ | I | H | 3-fluorophenyl |
| 2-581 | CF₃ | Br | Me | 3-fluorophenyl |
| 2-582 | CF₃ | I | Me | 3-fluorophenyl |
| 2-583 | CF₃ | Br | H | 6-(trifluoromethyl)pyridin-2-yl |
| 2-584 | CF₃ | I | H | 6-(trifluoromethyl)pyridin-2-yl |
| 2-585 | CF₃ | Br | Me | 6-(trifluoromethyl)pyridin-2-yl |
| 2-586 | CF₃ | I | Me | 6-(trifluoromethyl)pyridin-2-yl |
| 2-587 | CF₃ | Br | H | 6-chloropyridin-2-yl |
| 2-588 | CF₃ | I | H | 6-chloropyridin-2-yl |
| 2-589 | CF₃ | Br | Me | 6-chloropyridin-2-yl |
| 2-590 | CF₃ | I | Me | 6-chloropyridin-2-yl |
| 2-591 | CF₃ | Br | H | 5-chloropyridin-3-yl |
| 2-592 | CF₃ | I | H | 5-chloropyridin-3-yl |
| 2-593 | CF₃ | Br | Me | 5-chloropyridin-3-yl |
| 2-594 | CF₃ | I | Me | 5-chloropyridin-3-yl |
| 2-595 | CF₃ | Br | H | 5-fluoropyridin-3-yl |
| 2-596 | CF₃ | I | H | 5-fluoropyridin-3-yl |
| 2-597 | CF₃ | Br | Me | 5-fluoropyridin-3-yl |
| 2-598 | CF₃ | I | Me | 5-fluoropyridin-3-yl |
| 2-599 | CF₃ | Br | H | 6-chloropyridin-3-yl |
| 2-600 | CF₃ | I | H | 6-chloropyridin-3-yl |
| 2-601 | CF₃ | Br | Me | 6-chloropyridin-3-yl |
| 2-602 | CF₃ | I | Me | 6-chloropyridin-3-yl |
| 2-603 | CF₃ | Br | H | 6-fluoropyridin-3-yl |
| 2-604 | CF₃ | I | H | 6-fluoropyridin-3-yl |
| 2-605 | CF₃ | Br | Me | 6-fluoropyridin-3-yl |
| 2-606 | CF₃ | I | Me | 6-fluoropyridin-3-yl |
| 2-607 | CF₃ | Br | H | 2,3-difluorophenyl |
| 2-608 | CF₃ | I | H | 2,3-difluorophenyl |
| 2-609 | CF₃ | Br | Me | 2,3-difluorophenyl |
| 2-610 | CF₃ | I | Me | 2,3-difluorophenyl |
| 2-611 | CF₃ | Br | H | 3,5-difluorophenyl |
| 2-612 | CF₃ | I | H | 3,5-difluorophenyl |
| 2-613 | CF₃ | Br | Me | 3,5-difluorophenyl |
| 2-614 | CF₃ | I | Me | 3,5-difluorophenyl |

TABLE 41

| Compound No. | X¹ | X² | R⁴ | Q |
|---|---|---|---|---|
| 2-615 | CF₃ | Br | H | pyridin-2-yl |
| 2-616 | CF₃ | I | H | pyridin-2-yl |
| 2-617 | CF₃ | Br | Me | pyridin-2-yl |
| 2-618 | CF₃ | I | Me | pyridin-2-yl |
| 2-619 | CF₃ | Br | H | pyridin-3-yl |
| 2-620 | CF₃ | I | H | pyridin-3-yl |
| 2-621 | CF₃ | Br | Me | pyridin-3-yl |
| 2-622 | CF₃ | I | Me | pyridin-3-yl |

TABLE 41-continued

| Compound No. | X¹ | X² | R⁴ | Q |
|---|---|---|---|---|
| 2-623 | CF₃ | Br | H | pyridin-4-yl |
| 2-624 | CF₃ | I | H | pyridin-4-yl |
| 2-625 | CF₃ | Br | Me | pyridin-4-yl |
| 2-626 | CF₃ | I | Me | pyridin-4-yl |
| 2-627 | CF₃ | Br | H | Me |
| 2-628 | CF₃ | I | H | Me |
| 2-629 | CF₃ | Br | Me | Me |
| 2-630 | CF₃ | I | Me | Me |
| 2-631 | CF₃ | Br | H | Et |
| 2-632 | CF₃ | I | H | Et |
| 2-633 | CF₃ | Br | Me | Et |
| 2-634 | CF₃ | I | Me | Et |
| 2-635 | CF₃ | Br | H | n-Pr |
| 2-636 | CF₃ | I | H | n-Pr |
| 2-637 | CF₃ | Br | Me | n-Pr |
| 2-638 | CF₃ | I | Me | n-Pr |
| 2-639 | CF₃ | Br | H | i-Pr |
| 2-640 | CF₃ | I | H | i-Pr |
| 2-641 | CF₃ | Br | Me | i-Pr |
| 2-642 | CF₃ | I | Me | i-Pr |
| 2-643 | CF₃ | Br | H | methoxymethyl |
| 2-644 | CF₃ | I | H | methoxymethyl |
| 2-645 | CF₃ | Br | Me | methoxymethyl |
| 2-646 | CF₃ | I | Me | methoxymethyl |
| 2-647 | CF₃ | Br | H | trifluoromethyl |
| 2-648 | CF₃ | I | H | trifluoromethyl |
| 2-649 | CF₃ | Br | Me | trifluoromethyl |
| 2-650 | CF₃ | I | Me | trifluoromethyl |
| 2-651 | CF₃ | Br | H | methoxydifluoromethyl |
| 2-652 | CF₃ | I | H | methoxydifluoromethyl |
| 2-653 | CF₃ | Br | Me | methoxydifluoromethyl |
| 2-654 | CF₃ | I | Me | methoxydifluoromethyl |

TABLE 42

| Compound No. | X¹ | X² | R⁴ | Q |
|---|---|---|---|---|
| 2-655 | CF₃ | Br | H | ethylaminocarbonyl |
| 2-656 | CF₃ | I | H | ethylaminocarbonyl |
| 2-657 | CF₃ | Br | Me | ethylaminocarbonyl |
| 2-658 | CF₃ | I | Me | ethylaminocarbonyl |
| 2-659 | CF₃ | Br | H | 2,2,2-trifluoroethylaminocarbonyl |
| 2-660 | CF₃ | I | H | 2,2,2-trifluoroethylaminocarbonyl |
| 2-661 | CF₃ | Br | Me | 2,2,2-trifluoroethylaminocarbonyl |
| 2-662 | CF₃ | I | Me | 2,2,2-trifluoroethylaminocarbonyl |
| 2-663 | CF₃ | Br | H | N-ethyl-N-methylaminocarbonyl |
| 2-664 | CF₃ | I | H | N-ethyl-N-methylaminocarbonyl |
| 2-665 | CF₃ | Br | Me | N-ethyl-N-methylaminocarbonyl |
| 2-666 | CF₃ | I | Me | N-ethyl-N-methylaminocarbonyl |
| 2-667 | CF₃ | Br | H | N-(2,2,2-trifluoroethyl)-N-methylaminocarbonyl |
| 2-668 | CF₃ | I | H | N-(2,2,2-trifluoroethyl)-N-methylaminocarbonyl |
| 2-669 | CF₃ | Br | Me | N-(2,2,2-trifluoroethyl)-N-methylaminocarbonyl |
| 2-670 | CF₃ | I | Me | N-(2,2,2-trifluoroethyl)-N-methylaminocarbonyl |
| 2-671 | trifluoromethoxy | Br | H | 4-fluorophenyl |
| 2-672 | trifluoromethoxy | I | H | 4-fluorophenyl |
| 2-673 | trifluoromethoxy | Br | Me | 4-fluorophenyl |
| 2-674 | trifluoromethoxy | I | Me | 4-fluorophenyl |
| 2-675 | trifluoromethoxy | Br | H | 3-fluorophenyl |
| 2-676 | trifluoromethoxy | I | H | 3-fluorophenyl |
| 2-677 | trifluoromethoxy | Br | Me | 3-fluorophenyl |
| 2-678 | trifluoromethoxy | I | Me | 3-fluorophenyl |
| 2-679 | trifluoromethoxy | Br | H | 6-(trifluoromethyl)pyridin-2-yl |
| 2-680 | trifluoromethoxy | I | H | 6-(trifluoromethyl)pyridin-2-yl |
| 2-681 | trifluoromethoxy | Br | Me | 6-(trifluoromethyl)pyridin-2-yl |
| 2-682 | trifluoromethoxy | I | Me | 6-(trifluoromethyl)pyridin-2-yl |
| 2-683 | trifluoromethoxy | Br | H | 6-chloropyridin-2-yl |
| 2-684 | trifluoromethoxy | I | H | 6-chloropyridin-2-yl |
| 2-685 | trifluoromethoxy | Br | Me | 6-chloropyridin-2-yl |
| 2-686 | trifluoromethoxy | I | Me | 6-chloropyridin-2-yl |
| 2-687 | trifluoromethoxy | Br | H | 5-chloropyridin-3-yl |
| 2-688 | trifluoromethoxy | I | H | 5-chloropyridin-3-yl |
| 2-689 | trifluoromethoxy | Br | Me | 5-chloropyridin-3-yl |
| 2-690 | trifluoromethoxy | I | Me | 5-chloropyridin-3-yl |
| 2-691 | trifluoromethoxy | Br | H | 5-fluoropyridin-3-yl |
| 2-692 | trifluoromethoxy | I | H | 5-fluoropyridin-3-yl |

TABLE 43

| Compound No. | X¹ | X² | R⁴ | Q |
|---|---|---|---|---|
| 2-693 | trifluoromethoxy | Br | Me | 5-fluoropyridin-3-yl |
| 2-694 | trifluoromethoxy | I | Me | 5-fluoropyridin-3-yl |
| 2-695 | trifluoromethoxy | Br | H | 6-fluoropyridin-3-yl |
| 2-696 | trifluoromethoxy | I | H | 6-fluoropyridin-3-yl |

TABLE 43-continued

| Compound No. | X¹ | X² | R⁴ | Q |
|---|---|---|---|---|
| 2-697 | trifluoromethoxy | Br | Me | 6-fluoropyridin-3-yl |
| 2-698 | trifluoromethoxy | I | Me | 6-fluoropyridin-3-yl |
| 2-699 | trifluoromethoxy | Br | H | 2,3-difluorophenyl |
| 2-700 | trifluoromethoxy | I | H | 2,3-difluorophenyl |
| 2-701 | trifluoromethoxy | Br | Me | 2,3-difluorophenyl |
| 2-702 | trifluoromethoxy | I | Me | 2,3-difluorophenyl |
| 2-703 | trifluoromethoxy | Br | H | 3,5-difluorophenyl |
| 2-704 | trifluoromethoxy | I | H | 3,5-difluorophenyl |
| 2-705 | trifluoromethoxy | Br | Me | 3,5-difluorophenyl |
| 2-706 | trifluoromethoxy | I | Me | 3,5-difluorophenyl |
| 2-707 | difluoromethoxy | Br | H | 4-fluorophenyl |
| 2-708 | difluoromethoxy | I | H | 4-fluorophenyl |
| 2-709 | difluoromethoxy | Br | Me | 4-fluorophenyl |
| 2-710 | difluoromethoxy | I | Me | 4-fluorophenyl |
| 2-711 | difluoromethoxy | Br | H | 3-fluorophenyl |
| 2-712 | difluoromethoxy | I | H | 3-fluorophenyl |
| 2-713 | difluoromethoxy | Br | Me | 3-fluorophenyl |
| 2-714 | difluoromethoxy | I | Me | 3-fluorophenyl |
| 2-715 | difluoromethoxy | Br | H | 6-(trifluoromethyl)pyridin-2-yl |
| 2-716 | difluoromethoxy | I | H | 6-(trifluoromethyl)pyridin-2-yl |
| 2-717 | difluoromethoxy | Br | Me | 6-(trifluoromethyl)pyridin-2-yl |
| 2-718 | difluoromethoxy | I | Me | 6-(trifluoromethyl)pyridin-2-yl |
| 2-719 | difluoromethoxy | Br | H | 6-chloropyridin-2-yl |
| 2-720 | difluoromethoxy | I | H | 6-chloropyridin-2-yl |
| 2-721 | difluoromethoxy | Br | Me | 6-chloropyridin-2-yl |
| 2-722 | difluoromethoxy | I | Me | 6-chloropyridin-2-yl |
| 2-723 | difluoromethoxy | Br | H | 5-chloropyridin-3-yl |
| 2-724 | difluoromethoxy | I | H | 5-chloropyridin-3-yl |
| 2-725 | difluoromethoxy | Br | Me | 5-chloropyridin-3-yl |
| 2-726 | difluoromethoxy | I | Me | 5-chloropyridin-3-yl |
| 2-727 | difluoromethoxy | Br | H | 5-fluoropyridin-3-yl |
| 2-728 | difluoromethoxy | I | H | 5-fluoropyridin-3-yl |
| 2-729 | difluoromethoxy | Br | Me | 5-fluoropyridin-3-yl |
| 2-730 | difluoromethoxy | I | Me | 5-fluoropyridin-3-yl |
| 2-731 | difluoromethoxy | Br | H | 6-fluoropyridin-3-yl |
| 2-732 | difluoromethoxy | I | H | 6-fluoropyridin-3-yl |

TABLE 44

| Compound No. | X¹ | X² | R⁴ | Q |
|---|---|---|---|---|
| 2-733 | difluoromethoxy | Br | Me | 6-fluoropyridin-3-yl |
| 2-734 | difluoromethoxy | I | Me | 6-fluoropyridin-3-yl |
| 2-735 | difluoromethoxy | Br | H | 2,3-difluorophenyl |
| 2-736 | difluoromethoxy | I | H | 2,3-difluorophenyl |
| 2-737 | difluoromethoxy | Br | Me | 2,3-difluorophenyl |
| 2-738 | difluoromethoxy | I | Me | 2,3-difluorophenyl |
| 2-739 | difluoromethoxy | Br | H | 3,5-difluorophenyl |
| 2-740 | difluoromethoxy | I | H | 3,5-difluorophenyl |
| 2-741 | difluoromethoxy | Br | Me | 3,5-difluorophenyl |
| 2-742 | difluoromethoxy | I | Me | 3,5-difluorophenyl |

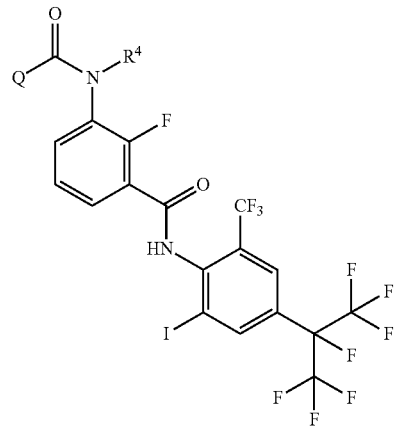

TABLE 45

| Compound No. | R⁴ | Q |
|---|---|---|
| 2-743 | ethyl | phenyl |
| 2-744 | acetyl | phenyl |
| 2-745 | ethylcarbonyl | phenyl |
| 2-746 | methoxycarbonyl | phenyl |
| 2-747 | ethoxycarbonyl | phenyl |
| 2-748 | methanesulfonyl | phenyl |
| 2-749 | methoxycarbonylethyl | phenyl |
| 2-750 | methylaminocarbonylethyl | phenyl |

TABLE 45-continued

| Compound No. | R⁴ | Q |
|---|---|---|
| 2-751 | ethyl | 4-fluorophenyl |
| 2-752 | acetyl | 4-fluorophenyl |
| 2-753 | ethylcarbonyl | 4-fluorophenyl |
| 2-754 | methoxycarbonyl | 4-fluorophenyl |
| 2-755 | ethoxycarbonyl | 4-fluorophenyl |
| 2-756 | methanesulfonyl | 4-fluorophenyl |
| 2-757 | methoxycarbonylethyl | 4-fluorophenyl |
| 2-758 | methylaminocarbonylethyl | 4-fluorophenyl |
| 2-759 | ethyl | 6-(trifluoromethyl)pyridin-3-yl |
| 2-760 | acetyl | 6-(trifluoromethyl)pyridin-3-yl |
| 2-761 | ethylcarbonyl | 6-(trifluoromethyl)pyridin-3-yl |
| 2-762 | methoxycarbonyl | 6-(trifluoromethyl)pyridin-3-yl |
| 2-763 | ethoxycarbonyl | 6-(trifluoromethyl)pyridin-3-yl |
| 2-764 | methanesulfonyl | 6-(trifluoromethyl)pyridin-3-yl |
| 2-765 | methoxycarbonylethyl | 6-(trifluoromethyl)pyridin-3-yl |
| 2-766 | methylaminocarbonylethyl | 6-(trifluoromethyl)pyridin-3-yl |
| 2-767 | ethyl | 5-fluoropyridin-3-yl |
| 2-768 | acetyl | 5-fluoropyridin-3-yl |
| 2-769 | ethylcarbonyl | 5-fluoropyridin-3-yl |
| 2-770 | methoxycarbonyl | 5-fluoropyridin-3-yl |
| 2-771 | ethoxycarbonyl | 5-fluoropyridin-3-yl |
| 2-772 | methanesulfonyl | 5-fluoropyridin-3-yl |
| 2-773 | methoxycarbonylethyl | 5-fluoropyridin-3-yl |
| 2-774 | methylaminocarbonylethyl | 5-fluoropyridin-3-yl |
| 2-775 | ethyl | 2,3-difluorophenyl |
| 2-776 | acetyl | 2,3-difluorophenyl |
| 2-777 | ethylcarbonyl | 2,3-difluorophenyl |
| 2-778 | methoxycarbonyl | 2,3-difluorophenyl |
| 2-779 | ethoxycarbonyl | 2,3-difluorophenyl |
| 2-780 | methanesulfonyl | 2,3-difluorophenyl |
| 2-781 | methoxycarbonylethyl | 2,3-difluorophenyl |
| 2-782 | methylaminocarbonylethyl | 2,3-difluorophenyl |

TABLE 46

| Compound No. | R⁴ | Q |
|---|---|---|
| 2-783 | ethyl | 3,5-difluorophenyl |
| 2-784 | acetyl | 3,5-difluorophenyl |
| 2-785 | ethylcarbonyl | 3,5-difluorophenyl |
| 2-786 | methoxycarbonyl | 3,5-difluorophenyl |
| 2-787 | ethoxycarbonyl | 3,5-difluorophenyl |
| 2-788 | methanesulfonyl | 3,5-difluorophenyl |
| 2-789 | methoxycarbonylethyl | 3,5-difluorophenyl |
| 2-790 | methylaminocarbonylethyl | 3,5-difluorophenyl |
| 2-791 | ethyl | 6-chloropyridin-2-yl |
| 2-792 | acetyl | 6-chloropyridin-2-yl |
| 2-793 | ethylcarbonyl | 6-chloropyridin-2-yl |
| 2-794 | methoxycarbonyl | 6-chloropyridin-2-yl |
| 2-795 | ethoxycarbonyl | 6-chloropyridin-2-yl |
| 2-796 | methanesulfonyl | 6-chloropyridin-2-yl |
| 2-797 | methoxycarbonylethyl | 6-chloropyridin-2-yl |
| 2-798 | methylaminocarbonylethyl | 6-chloropyridin-2-yl |
| 2-799 | ethyl | 5-chloropyridin-3-yl |
| 2-800 | acetyl | 5-chloropyridin-3-yl |
| 2-801 | ethylcarbonyl | 5-chloropyridin-3-yl |
| 2-802 | methoxycarbonyl | 5-chloropyridin-3-yl |
| 2-803 | ethoxycarbonyl | 5-chloropyridin-3-yl |
| 2-804 | methanesulfonyl | 5-chloropyridin-3-yl |
| 2-805 | methoxycarbonylethyl | 5-chloropyridin-3-yl |
| 2-806 | methylaminocarbonylethyl | 5-chloropyridin-3-yl |

The imide compounds represented by Formula (IV), which are obtained by the method of producing an aromatic amide derivative of the invention, are extremely useful as intermediates in the method of producing an amide derivative that exhibits excellent efficacy in terms of pest controlling effects.

EXAMPLES

Hereinafter, the present invention is further explained in more detail with reference to Examples; however it should be construed that the invention is by no means limited thereto.

Note that the chemical shift values of $^1$H-NMR are expressed in ppm unit at the lower magnetic field side on the basis of tetramethylsilane, "s" means a singlet, "d" means a doublet, "t" means a triplet, "m" means a multiplet, and "brs" means a broad singlet. Further, unless otherwise specifically stated, "parts" and "%" are expressed in terms of mass basis.

Reference Example 1

Synthesis of N-[2-fluoro-3-[benzoyl(methyl)amino] benzoyl]-3-[benzoyl(methyl)amino]-N-[2-bromo-4-(heptafluoroisopropan-2-yl)-6-(trifluoromethyl)phenyl]-2-fluorobenzamide (Compound No.: 1-123)

1.00 g of 2-bromo-4-(heptafluoroisopropan-2-yl)-6-(trifluoromethyl)aniline, 0.89 g of triethylamine, 0.03 g of N,N-dimethyl-4-aminopyridine, and 1.57 g of 2-fluoro-3-(N-methylbenzamide)benzoyl chloride were added to 4.00 g of 1,3-dimethyl-2-imidazolidinon, and the mixture was stirred at room temperature for 1 hour. The resulting reaction solution was extracted with ethyl acetate, washed with saturated brine, and the organic phase was dried over magnesium sulfate. After filtering off the magnesium sulfate, the solution was concentrated and purified by silica gel chromatography to obtain 2.20 g of the aimed imide compound (Compound No.: 1-123) (isolation yield: 97%) as a white solid.

The $^1$H-NMR chemical shift values of the obtained imide compound are shown below.

$^1$H-NMR (DMSO-d$_6$, 70° C.) δppm: 8.44 (s, 1H), 7.99 (s, 1H), 7.60-7.57 (m, 2H), 7.51 (brs, 2H), 7.30-7.18 (m, 12H), 3.12 (s, 6H)

MS (M+H)$^+$=918, 920

Reference Example 2

Synthesis of N-[2-fluoro-3-[benzoyl(methyl)amino]benzoyl]-3-[benzoyl(methyl)amino]-N-[2-bromo-4-(heptafluoroisopropan-2-yl)-6-(trifluoromethyl)phenyl]-2-fluorobenzamide (Compound No.: 1-123)

2.16 g of the aimed imide compound (Compound No. 1-123) (isolation yield: 95%) was obtained as a white solid in the same procedure as in Reference Example 1, except that the reaction solvent was changed to 3.00 g of toluene in place of 4.00 g of 1,3-dimethyl-2-imidazolidinon and the reaction condition was changed to stirring at 90° C. for 4 hours in place of stirring at room temperature for 1 hour.

Reference Example 3

Synthesis of N-[2-fluoro-3-[benzoyl(methyl)amino]benzoyl]-3-[benzoyl(methyl)amino]-N-[4-(heptafluoroisopropan-2-yl)-2-iodo-6-(trifluoromethyl)phenyl]-2-fluorobenzamide (Compound No.: 1-124)

3.79 g of 4-(heptafluoroisopropan-2-yl)-2-iodo-6-(trifluoromethyl)aniline, 2.80 g of triethylamine, 0.06 g of N,N-dimethyl-4-aminopyridine, and 5.3 g of 2-fluoro-3-(N-methylbenzamido)benzoyl chloride were added to 7.6 g of toluene, and the mixture was stirred at 90° C. for 2 hours. The resulting reaction solution was cooled to room temperature, and the crystal precipitated upon addition of water was filtered off and washed sequentially with toluene and water to obtain 5.87 g (isolation yield: 73%) of the aimed imide compound (Compound No. 1-124) as a pale yellow solid.

The $^1$H-NMR chemical shift values of the obtained imide compound are shown below.

$^1$H-NMR (DMSO-d$_6$, 70° C.) δppm: 8.53 (s, 1H), 7.97 (s, 1H), 7.54-7.51 (m, 4H), 7.30-7.13 (m, 12H), 3.14 (s, 6H)

MS (M+H)$^+$=966

Reference Example 4

Synthesis of N-[2-fluoro-3-[4-fluorobenzoyl(methyl)amino]benzoyl]-3-[4-fluorobenzoyl(methyl)amino]-N-[2-bromo-4-(heptafluoroisopropan-2-yl)-6-(trifluoromethyl)phenyl]-2-fluorobenzamide (Compound No.: 1-127)

The aimed imide compound (Compound No. 1-127) was synthesized by the same synthetic method as in Reference Example 1, except that 2-bromo-4-(heptafluoroisopropan-2-yl)-6-(trifluoromethyl)aniline was changed to 4-(heptafluoroisopropan-2-yl)-2-bromo-6-(trifluoromethyl)aniline, and 2-fluoro-3-(N-methylbenzamido)benzoyl chloride was changed to 2-fluoro-3-[4-fluorobenzoyl(methyl)amino]benzoyl chloride.

The $^1$H-NMR chemical shift values of the obtained imide compound are shown below.

$^1$H-NMR (DMSO-d$_6$, 70° C.)) δppm: 8.44 (s, 1H), 7.97 (s, 1H), 7.64-7.62 (m, 2H), 7.50 (brs, 2H), 7.28-7.24 (m, 6H), 7.00-6.96 (m, 4H), 3.15 (s, 6H)

MS (M+H)$^+$=954, 956

Reference Example 5

Synthesis of N-[2-fluoro-3-[4-fluorobenzoyl(methyl)amino]benzoyl]-3-[4-fluorobenzoyl(methyl)amino]-N-[4-(heptafluoroisopropan-2-yl-)-2-iodo-6-(trifluoromethyl)phenyl]-2-fluorobenzamide (Compound No.: 1-128)

The aimed imide compound (Compound No. 1-128) was synthesized by the same synthetic method as in Reference Example 1, except that 2-bromo-4-(heptafluoroisopropan-2-yl)-6-(trifluoromethyl)aniline was changed to 4-(heptafluoroisopropan-2-yl)-2-iodo-6-(trifluoromethyl)aniline, and 2-fluoro-3-(N-methylbenzamido)benzoyl chloride was changed to 2-fluoro-3-[4-fluorobenzoyl(methyl)amino]benzoyl chloride.

The $^1$H-NMR chemical shift values of the obtained imide compound are shown below.

$^1$H-NMR (DMSO-d$_6$, 70° C.)) δppm: 8.53 (s, 1H), 7.95 (s, 1H), 7.59-7.57 (m, 2H), 7.48 (brs, 2H), 7.28-7.22 (m, 6H), 7.01-6.97 (m, 4H), 3.16 (s, 6H)

MS (M+H)$^+$=1002

Reference Example 6

Synthesis of N-[2-fluoro-3-[2,6-difluorobenzoyl(methyl)amino]benzoyl]-3-[2,6-difluorobenzoyl(methyl)amino]-N-[2-bromo-4-(heptafluoroisopropan-2-yl-)-6-(trifluoromethyl)phenyl]-2-fluorobenzamide (Compound No.: 1-135)

The aimed imide compound (Compound No. 1-135) was synthesized by the same synthetic method as in Reference Example 1, except that 2-bromo-4-(heptafluoroisopropan-2-yl)-6-(trifluoromethyl)aniline was changed to 4-(heptafluoroisopropan-2-yl)-2-bromo-6-(trifluoromethyl)aniline, and 2-fluoro-3-(N-methylbenzamido)benzoyl chloride was changed to 2-fluoro-3-[2,6-difluorobenzoyl(methyl)amino]benzoyl chloride.

The $^1$H-NMR chemical shift values of the obtained imide compound are shown below.

$^1$H-NMR (DMSO-d$_6$, 70° C.)) δppm: 8.46 (s, 1H), 8.01 (s, 1H), 7.33-7.30 (m, 4H), 7.25-7.11 (m, 5H), 6.86 (brs, 3H), 3.17 (s, 6H)

MS (M+H)$^+$=990, 992

Reference Example 7

Synthesis of N-[2-fluoro-3-[4-nitrobenzoyl(methyl)amino]benzoyl]-3-[4-nitrobenzoyl(methyl)amino]-N-[2-bromo-4-(heptafluoroisopropan-2-yl)-6-(trifluoromethyl)phenyl]-2-fluorobenzamide (Compound No.: 1-577)

The aimed imide compound (Compound No. 1-577) was synthesized by the same synthetic method as in Reference Example 1, except that 2-bromo-4-(heptafluoroisopropan-2-yl)-6-(trifluoromethyl)aniline was changed to 4-(heptafluoroisopropan-2-yl)-2-bromo-6-(trifluoromethyl)aniline, and 2-fluoro-3-(N-methylbenzamido)benzoyl chloride was changed to 2-fluoro-3-[4-nitrobenzoyl(methyl)amino]benzoyl chloride.

The $^1$H-NMR chemical shift values of the obtained imide compound are shown below.

$^1$H-NMR (DMSO-d$_6$, 70° C.)) δppm: 8.41 (s, 1H), 8.03-8.01 (m, 4H), 7.92 (s, 1H), 7.72-7.70 (m, 6H), 7.30-7.24 (m, 2H), 3.20 (s, 6H)
MS (M+Na)$^+$=1030, 1032

Reference Example 8

Synthesis of N-[2-fluoro-3-[4-nitrobenzoyl(methyl)amino]benzoyl]-3-[4-nitrobenzoyl(methyl)amino]-N-[4-(heptafluoroisopropan-2-yl)-2-iodo-6-(trifluoromethyl)phenyl]-2-fluorobenzamide (Compound No.: 1-578)

The aimed imide compound (Compound No. 1-578) was synthesized by the same synthetic method as in Reference Example 1, except that 2-bromo-4-(heptafluoroisopropan-2-yl)-6-(trifluoromethyl)aniline was changed to 4-(heptafluoroisopropan-2-yl)-2-iodo-6-(trifluoromethyl)aniline, and 2-fluoro-3-(N-methylbenzamido)benzoyl chloride was changed to 2-fluoro-3-[4-nitrobenzoyl(methyl)amino]benzoyl chloride.
The $^1$H-NMR chemical shift values of the obtained imide compound are shown below.
$^1$H-NMR (DMSO-d$_6$, 70° C.) δppm: 8.49 (s, 1H), 8.03-8.02 (m, 4H), 7.92 (s, 1H), 7.70-7.67 (m, 2H), 7.49-7.48 (m, 4H), 7.25-7.24 (m, 2H), 3.21 (s, 6H)
MS (M+Na)$^+$=1078

Reference Example 9

Synthesis of N-[2-fluoro-3-[benzoyl(methyl)amino]benzoyl]-3-[benzoyl(methyl)amino]-N-[2,4-bis(heptafluoroisopropan-2-yl)-6-(trifluoromethyl)phenyl]-2-fluorobenzamide (Compound No.: 1-246)

The aimed imide compound (Compound No. 1-246) was synthesized by the same synthetic method as in Reference Example 1, except that 2-bromo-4-(heptafluoroisopropan-2-yl)-6-(trifluoromethyl)aniline was changed to 2,4-bis(heptafluoroisopropan-2-yl)-6-(trifluoromethyl)aniline, and 2-fluoro-3-(N-methylbenzamide)benzoyl chloride was changed to 2-fluoro-3-[benzoyl(methyl)amino]benzoyl chloride.
The $^1$H-NMR chemical shift values of the obtained imide compound are shown below.
$^1$H-NMR (DMSO-d$_6$, 70° C.)) δppm: 8.48 (s, 1H), 8.07 (s, 1H), 7.57-7.54 (m, 2H), 7.34 (brs, 2H), 7.28-7.18 (m, 14H), 3.07 (s, 6H)
MS(M+H)$^+$=1008

Reference Example 10

Synthesis of N-[2-fluoro-3-[benzoyl(methyl)amino]benzoyl]-3-[benzoyl(methyl)amino]-N-[4-bromo-2-(heptafluoroisopropan-2-yl)-6-(trifluoromethyl)phenyl]-2-fluorobenzamide (Compound No.: 1-240)

The aimed imide compound (Compound No. 1-240) was synthesized by the same synthetic method as in Reference Example 1, except that 2-bromo-4-(heptafluoroisopropan-2-yl)-6-(trifluoromethyl)aniline was changed to 2-(heptafluoroisopropan-2-yl)-4-bromo-6-(trifluoromethyl)aniline, and 2-fluoro-3-(N-methylbenzamido)benzoyl chloride was changed to 2-fluoro-3-[benzoyl(methyl)amino]benzoyl chloride.
The $^1$H-NMR chemical shift values of the obtained imide compound are shown below.

$^1$H-NMR (DMSO-d$_6$, 70° C.)) δppm: 8.52 (s, 1H), 8.09 (s, 1H), 7.51-7.48 (m, 2H), 7.28-7.26 (m, 2H), 7.21-7.19 (m, 12H), 3.08 (s, 6H)
MS (M+H)$^+$=918, 920

Reference Example 11

Synthesis of N-[2-fluoro-3-[benzoyl(methyl)amino]benzoyl]-3-[benzoyl(methyl)amino]-N-[2,6-dibromo-4-(nonafluoro-sec-butyl)phenyl]-2-fluorobenzamide (Compound No.: 1-168)

The aimed imide compound (Compound No. 1-168) was synthesized by the same synthetic method as in Reference Example 1, except that 2-bromo-4-(heptafluoroisopropan-2-yl)-6-(trifluoromethyl)aniline was changed to 4-(nonafluoro-sec-butyl)-2,6-dibromoaniline, and 2-fluoro-3-(N-methylbenzamido)benzoyl chloride was changed to 2-fluoro-3-[benzoyl(methyl)amino]benzoyl chloride.
The $^1$H-NMR chemical shift values of the obtained imide compound are shown below.
$^1$H-NMR (DMSO-d$_6$, 70° C.) δppm: 7.95 (s, 2H), 7.61-7.58 (m, 2H), 7.50 (brs, 2H), 7.29-7.26 (m, 2H), 7.22-7.16 (m, 10H), 3.21 (s, 6H)
MS (M+Na)$^+$=1000, 1002

Example 1

Synthesis of 2-fluoro-3-(N-methylbenzamido)-N-(2-bromo-4-(heptafluoroisopropan-2-yl)-6-(trifluoromethyl)phenyl)benzamide (Compound No.: 2-123)

5.0 g of N-[2-fluoro-3-[benzoyl(methyl)amino]benzoyl]-3-[benzoyl(methyl)amino]-N-[2-bromo-4-(heptafluoroisopropan-2-yl)-6-(trifluoromethyl)phenyl]-2-fluorobenzamide (Compound No.: 1-123) obtained in Reference Example 1 and 0.07 g of N,N-dimethyl-4-aminopyridine were added to 28.3 g of toluene, and the mixture was stirred at 80° C. for 10 minutes. 10 g of a 6% aqueous sodium carbonate solution was added to the resulting reaction solution, and the mixture was stirred at 80° C. for 5 hours. Analysis of the obtained reaction solution by HPLC confirmed that the aimed aromatic amide derivative (Compound No.: 2-123) was obtained in a yield of 98.8%.

Example 2

Synthesis of 2-fluoro-3-(N-methylbenzamido)-N-(2-bromo-4-(heptafluoroisopropan-2-yl)-6-(trifluoromethyl)phenyl)benzamide (Compound No.: 2-123)

Compound No.: 2-123 was obtained by performing the same procedure as in Example 1, except that the procedure of "adding 10 g of a 6% aqueous sodium carbonate solution to the resulting reaction solution and stirring at 80° C. for 5 hours" in Example 1 was changed to a procedure of "adding 10 g of a 2% aqueous sodium hydroxide solution to the resulting reaction solution and stirring at 80° C. for 5 hours".
Analysis of the obtained reaction solution by HPLC confirmed that the aimed aromatic amide derivative (Compound No.: 2-123) was obtained in a yield of 99.7%.

Example 3

Synthesis of 2-fluoro-3-(4-fluoro-N-methylbenzamido)-N-(2-iodo-4-(heptafluoroisopropyl)-6-(trifluoromethyl)phenyl)benzamide (Compound No.: 2-128)

45 g of N-[2-fluoro-3-[4-fluorobenzoyl(methyl)amino]benzoyl]-3-[4-fluorobenzoyl(methyl)amino]-N-[4-(heptafluoroisopropan-2-yl)-2-iodo-6-(trifluoromethyl)phenyl]-2-fluorobenzamide (Compound No.: 1-128) obtained in Reference Example 5, 0.28 g of N,N-dimethyl-4-aminopyridine, and 74 g of a 10% aqueous potassium carbonate solution were added to 90.0 g of toluene, and the mixture was stirred at 80° C. for 8 hours. The resulting reaction solution was cooled to 50° C. and separated into an aqueous phase and an organic phase. 16.3 g of 1% hydrochloric acid and 3.2 g of sodium chloride were added to the resulting organic phase and the mixture was separated into an aqueous phase and an organic phase at 50° C. The resulting organic phase was distilled off to partially remove the solvent (toluene 37 g) under reduced pressure, and then crystallized under cooling conditions in an ice-bath. The resulting solid was washed with 11 g of toluene and dried under reduced pressure at 50° C. to obtain the aimed aromatic amide derivative (Compound No. 2-128) in an isolation yield of 94%.

Reference Example 12

Synthesis of 2-fluoro-3-(4-fluoro-N-methylbenzamido)-N-(2-iodo-4-(heptafluoroisopropyl)-6-(trifluoromethyl)phenyl)benzamide (Compound No.: 2-128)

35.0 g of 2-fluoro-3-(4-fluoro-N-methylbenzamido)benzoic acid and 0.44 g of dimethylformamide were added to 105 g of toluene, and the reaction temperature was raised to 80° C. After dropwise addition of 17.32 g of thionyl chloride thereto over a period of 30 minutes, the mixture was stirred for 1 hour. The resulting reaction solution was cooled to 50° C. and a portion of the solvent was distilled off under reduced pressure to prepare 53.98 g of a toluene solution of 2-fluoro-3-(4-fluoro-N-methylbenzamido)benzoyl chloride.

After 23.7 g of 2-iodo-4-(heptafluoroisopropan-2-yl)-6-(trifluoromethyl)aniline and 0.32 g of N,N-dimethyl-4-aminopyridine were added to 47.4 g of toluene, the toluene solution of 2-fluoro-3-(4-fluoro-N-methylbenzamido)benzoyl chloride prepared above was added thereto at 20° C. and the mixture was stirred. The temperature of the resulting reaction solution was raised to 80° C. and then 16.0 g of triethylamine was dropwise added thereto over a period of 30 minutes. The mixture was stirred at 95° C. for 3 hours. The resulting reaction solution was cooled to 40° C., and 79.86 g of water was added thereto and the mixture was stirred at 30° C. for 30 minutes. The resulting reaction solution was cooled to 0° C. and stirred for 1 hour. The precipitated solid was filtered off, washed successively with 20.0 g of toluene and 39.9 g of water and dried under reduced pressure at 50° C. to obtain 48.4 g of N-[2-fluoro-3-[4-fluorobenzoyl(methyl)amino]benzoyl]-3-[4-fluorobenzoyl(methyl)amino]-N-[4-(heptafluoroisopropan-2-yl)-2-iodo-6-(trifluoromethyl)phenyl]-2-fluorobenzamide (Compound No.: 1-128).

Example 4

45 g of N-[2-fluoro-3-[4-fluorobenzoyl(methyl)amino]benzoyl]-3-[4-fluorobenzoyl(methyl)amino]-N-[4-(heptafluoroisopropan-2-yl)-2-iodo-6-(trifluoromethyl)phenyl]-2-fluorobenzamide (Compound No.: 1-128) obtained in Reference Example 12, 0.28 g of N,N-dimethyl-4-aminopyridine, and 74 g of a 10% aqueous potassium carbonate solution were added to 90.0 g of toluene, and the mixture was stirred at 80° C. for 8 hours. The resulting reaction solution was cooled to 50° C. and separated into an aqueous phase and an organic phase. 16.3 g of 1% hydrochloric acid and 3.2 g of sodium chloride were added to the resulting organic phase to separate into an aqueous phase and an organic phase at 50° C. The resulting organic phase was distilled off under reduced pressure to remove a portion (toluene 37 g) of the solvent, and then crystallized under the conditions in an ice-bath. The resulting solid was washed with 11 g of toluene and dried under reduced pressure at 50° C. to obtain 30.2 g of the aimed aromatic amide derivative (Compound No.: 2-128) in a total yield of 86%.

Example 5

Synthesis of 2-fluoro-3-(N-methylbenzamido)-N-(2-bromo-4-(heptafluoroisopropyl)-6-(trifluoromethyl)phenyl)benzamide (Compound No.: 2-123)

40.0 g of 2-bromo-4-(heptafluoroisopropan-2-yl)-6-(trifluoromethyl)aniline, 1.17 g of N,N-dimethyl-4-aminopyridine, and 29.0 g of triethylamine were added to 40.0 g of toluene, and the temperature was raised to 95° C. After dropwise addition of a 33.5% toluene solution of 2-fluoro-3-(N-methylbenzamido)benzoyl chloride over a period of 30 minutes to the resulting reaction solution, the mixture was stirred at 95° C. for 4 hours. 100 g of a 10% aqueous sodium carbonate solution was added to the resulting reaction solution, and the mixture was stirred at 85° C. for 3 hours. The resulting reaction solution was separated into an aqueous phase and an organic phase at 85° C. while the reaction solution was hot, and 40 g of a 10% aqueous sodium carbonate solution was added to the resulting organic phase. The mixture was stirred at 80° C. for 1 hour and the resulting reaction solution was again separated into an aqueous phase and an organic phase at 80° C. while the reaction solution was hot, and 40 g of water was added to the resulting organic phase, followed by separation into an aqueous phase and an organic phase at 80° C. After cooling the resulting organic phase to room temperature, the solution was stirred in an ice bath for 4 hours. The precipitated solid was filtered off and dried under reduced pressure at 60° C. to obtain 58.12 g of the aimed aromatic amide derivative (Compound No.: 2-123) in a yield of 93% as determined by HPLC.

Example 6

Synthesis of N-(2,4-bis(heptafluoroisopropyl)-6-(trifluoromethyl)phenyl)-2-fluoro-3-(N-methylbenzamido)benzamide (Compound No.: 2-246)

Using N-[2-fluoro-3-[benzoyl(methyl)amino]benzoyl]-3-[benzoyl(methyl)amino]-N-[2,4-bis(heptafluoroisopropyl)-6-(trifluoromethyl)phenyl]-2-fluorobenzamide (Compound No.: 1-246) obtained in Reference Example 9, the aimed aromatic amide derivative (Compound No.: 2-246) was obtained by the method described in Example 2.

The $^1$H-NMR chemical shift values of the obtained aromatic amide derivative are shown below.

$^1$H-NMR (DMSO-$d_6$, 70° C.) δ: 10.45 (1H, s), 8.33 (1H, s), 7.99 (1H, s), 7.60 (1H, t, J=7.6 Hz), 7.48-7.47 (1H, m), 7.31-7.23 (6H, m), 3.34 (3H, s)

Example 7

Synthesis of N-(4-bromo-2-(heptafluoroisopropyl)-6-(trifluoromethyl)phenyl)-2-fluoro-3-(N-methylbenzamido)benzamide (Compound No.: 2-240)

Using N-[2-fluoro-3-[benzoyl(methyl)amino]benzoyl]-3-[benzoyl(methyl)amino]-N-[4-bromo-2-(heptafluoroisopropan-2-yl)-6-(trifluoromethyl)phenyl]-2-fluorobenzamide (Compound No.: 1-240) obtained in Reference Example 10, the aimed aromatic amide derivative (Compound No.: 2-240) was obtained by the method described in Example 2.

The $^1$H-NMR chemical shift values of the obtained aromatic amide derivative are shown below.

$^1$H-NMR (DMSO-d$_6$, 70° C.) δ: 10.12 (1H, s), 8.36 (1H, d, J=2.1 Hz), 8.00 (1H, s), 7.55 (1H, t, J=7.6 Hz), 7.44 (1H, t, J=6.4 Hz), 7.32-7.23 (3H, m), 3.34 (3H, s)

Example 8

Synthesis of 2-fluoro-3-(N-methylbenzamido)-N-(2-bromo-4-(heptafluoroisopropyl)-6-(trifluoromethyl) phenyl)benzamide (Compound No.: 2-123)

529.5 g of 2-fluoro-3-(N-methylbenzamido)benzoic acid and 27.5 g of dimethylformamide were added to 772 g of toluene, and the temperature was raised to 40° C. Then, a mixed solution of 237.0 g of thionyl chloride and 237.0 g of toluene were added thereto over a period of 2 hours, followed by further addition of 50 g of toluene. After stirring for 4 hours, the mixture was depressurized and cooled to 25° C. to prepare 1678.5 g of a toluene solution of 2-fluoro-3-(N-methylbenzamido)benzoyl chloride.

327.0 g of 2-bromo-4-(heptafluoroisopropan-2-yl)-6-(trifluoromethyl)aniline, 9.5 g of N,N-dimethyl-4-aminopyridine, and 233.5 g of triethylamine were added to 163.5 g of toluene, and 1641.5 g of a toluene solution of 2-fluoro-3-(N-methylbenzamido)benzoyl chloride prepared above was added thereto at 95° C. After further addition of 163.5 g of toluene, the mixture was stirred for 5 hours to perform the imidation reaction. Thereafter, the reaction solution was cooled to 85° C. and 817.5 g of a 10% aqueous sodium carbonate solution was added. The mixture was stirred for 4 hours to carry out the hydrolysis. Then, the reaction solution was separated into an organic phase A and an aqueous phase A at 85° C. while the reaction solution was hot. 328.0 g of a 10% aqueous sodium carbonate was added to the resulting organic phase A and the mixture was stirred at 80° C. for 1 hour, followed by separation into an organic phase B and an aqueous phase B. 330 g of water was added to the resulting organic phase B and the mixture was stirred at 80° C. for 30 minutes, after which time a liquid separation was performed to obtain an organic phase C.

The reaction solution of the resulting organic phase C was cooled to 0° C. over a period of 12 hours and the precipitated solid was filtered off. The solid was washed with 327.5 g of toluene and dried under reduced pressure at 50° C. to obtain 389.0 g of 2-fluoro-3-(N-methylbenzamido)-N-(2-bromo-4-(heptafluoroisopropyl)-6-(trifluoromethyl)phenyl)benzamide (Compound No.: 2-123) with a purity of 99.3 wt % in a yield of 75.9%.

1707.5 g of a mixed solution of the aqueous phase A and the aqueous phase B obtained above (16.8% aqueous 2-fluoro-3-(N-methylbenzamido)benzoic acid sodium salt solution) was added to 766.5 g of 10% hydrochloric acid at 70° C. over a period of 1 hour, and the mixture was stirred for 1 hour. Thereafter, the mixture was cooled to 30° C. and stirred for 1 hour. The precipitated solid (2-fluoro-3-(N-methylbenzamido)benzoic acid) was filtered off. The resulting solid was washed with 860 g of water and dried under reduced pressure at 60° C. to recover 293.5 g of 2-fluoro-3-(N-methylbenzamido)benzoic acid with a purity of 95.6 wt % in a yield of 98.0%.

200 g of 2-fluoro-3-(N-methylbenzamido)benzoic acid recovered above and 10.2 g of dimethylformamide were added to 300 g of toluene and the temperature was raised to 40° C. Then, a mixed solution of 101.9 g of thionyl chloride and 100 g of toluene was added thereto under reduced pressure and the mixture was stirred for 3 hours. After depressurization, the reaction solution was cooled to 20° C. to prepare 608.2 g of a toluene solution of a recovered 2-fluoro-3-(N-methylbenzamido)benzoyl chloride.

40.0 g of 2-bromo-4-(heptafluoroisopropan-2-yl)-6-(trifluoromethyl)aniline, 1.15 g of N,N-dimethyl-4-aminopyridine, and 28.6 g of triethylamine were added to 20.0 g of toluene, and 196.1 g of a toluene solution of the recovered 2-fluoro-3-(N-methylbenzamido)benzoyl chloride prepared above was added thereto at 85° C. After further addition of 20.0 g of toluene, the mixture was stirred for 4 hours to perform an imidation reaction.

Subsequently, 99.8 g of a 10% aqueous sodium carbonate solution was added thereto, and the mixture was stirred for 3 hours to perform a hydrolysis reaction. Then, the reaction solution was separated into an organic phase A' and an aqueous phase A' at 80° C. while the reaction solution was hot. 39.9 g of a 10% aqueous sodium carbonate solution was further added to the resulting organic phase A', the mixture was stirred for 1 hour to carry out the hydrolysis reaction. Then, the reaction solution was separated into an organic phase B' and an aqueous phase B'. 40 g of water was added to the resulting organic phase B' and the mixture was stirred at 80° C. for 30 minutes, followed by liquid separation to obtain the organic phase C'. The resulting organic phase C' was cooled to 0° C. over a period of 12 hours, thereby to precipitate a solid. The precipitated solid was filtered off, washed with 40.0 g of toluene, and dried under reduced pressure at 60° C. to obtain 55.8 g of 2-fluoro-3-(N-methylbenzamido)-N-(2-bromo-4-(heptafluoroisopropyl)-6-(trifluoromethyl)phenyl)benzamide (Compound No.: 2-123) with a purity of 99.0 wt % in a yield of 89.7%.

As described above, the aimed aromatic amide derivative can be obtained in a high yield according to the method of producing an aromatic amide derivative of the present invention.

The disclosure of Japanese Patent Application No. 2015-247774, filed Dec. 18, 2015 is incorporated by reference herein in its entirety.

All publications, patent applications, and technical standards mentioned in this specification are herein incorporated by reference to the same extent as if such individual publication, patent application, or technical standard was specifically and individually indicated to be incorporated by reference.

Each and every compatible combination of the embodiments described in this application is explicitly disclosed herein, as if each and every combination was individually and explicitly recited.

The invention claimed is:

1. A method of producing an aromatic amide derivative of the following Formula (I), comprising the following process a and process b:

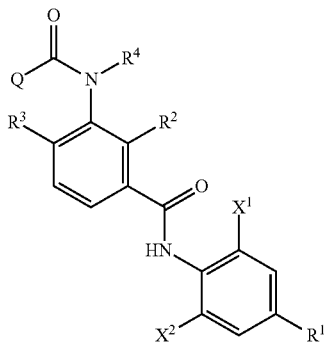

(I)

in Formula (I), $R^1$ represents a halogen atom; a $C_1$-$C_4$ haloalkyl group; or a $C_1$-$C_4$ haloalkyl group substituted by 1 to 8 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group;

each of $X^1$ and $X^2$ independently represents a hydrogen atom, a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, a nitro group, a $C_1$-$C_4$ alkylcarbonyl group, or a $C_1$-$C_4$ haloalkylcarbonyl group;

each of $R^2$ and $R^3$ independently represents a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfinyl group, a $C_1$-$C_4$ haloalkylsulfinyl group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group;

$R^4$ represents:
a hydrogen atom;
a $C_1$-$C_4$ alkyl group;
a $C_1$-$C_4$ haloalkyl group;
a $C_1$-$C_4$ alkylcarbonyl group;
a $C_1$-$C_4$ haloalkylcarbonyl group;
a $C_1$-$C_4$ alkoxycarbonyl group;
a $C_1$-$C_4$ haloalkoxycarbonyl group;
a $C_1$-$C_4$ alkylsulfonyl group;
a $C_1$-$C_4$ haloalkylsulfonyl group; or
a $C_1$-$C_4$ alkyl group, a $C_1$-$C_4$ haloalkyl group, a $C_1$-$C_4$ alkylcarbonyl group, a $C_1$-$C_4$ haloalkylcarbonyl group, a $C_1$-$C_4$ alkoxycarbonyl group, a $C_1$-$C_4$ haloalkoxycarbonyl group, a $C_1$-$C_4$ alkylsulfonyl group, or a $C_1$-$C_4$ haloalkylsulfonyl group, substituted by 1 to 9 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a $C_1$-$C_4$ alkylcarbonyl group, a $C_1$-$C_4$ alkoxycarbonyl group, a di-$C_1$-$C_4$ alkylaminocarbonyl group, a cyano group, and a nitro group; and Q represents:
a $C_1$-$C_4$ alkyl group;
a $C_1$-$C_4$ haloalkyl group;
a $C_1$-$C_4$ alkylaminocarbonyl group;
a $C_1$-$C_4$ haloalkylaminocarbonyl group;
a di-$C_1$-$C_4$ alkylaminocarbonyl group;
a di-$C_1$-$C_4$ haloalkylaminocarbonyl group;
a phenyl group;
a heterocyclic group;
a $C_1$-$C_4$ alkyl group or a $C_1$-$C_4$ haloalkyl group, substituted by 1 to 9 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group;

a phenyl group substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; or a heterocyclic group substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group;

wherein the heterocyclic group is a pyridyl group, a pyridyl-N-oxide group, a pyrimidyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group; and wherein the process a comprises reacting an aniline derivative of the following Formula (II) with a carboxylic acid derivative of the following Formula (III), in the presence of a base, to thereby obtain an imide compound of the following Formula (IV):

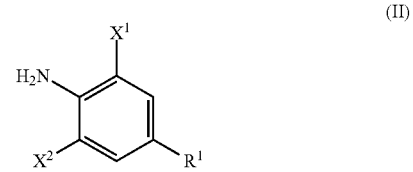

(II)

in Formula (II), $R^1$, $X^1$, and $X^2$ are the same as $R^1$, $X^1$, and $X^2$ in Formula (I),

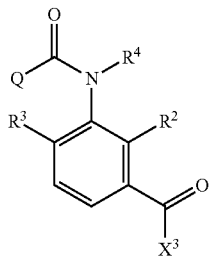

(III)

in Formula (III), $X^3$ represents a halogen atom or a $C_1$-$C_4$ alkoxy group, and $R^2$, $R^3$, $R^4$, and Q are the same as $R^2$, $R^3$, $R^4$, and Q in Formula (I),

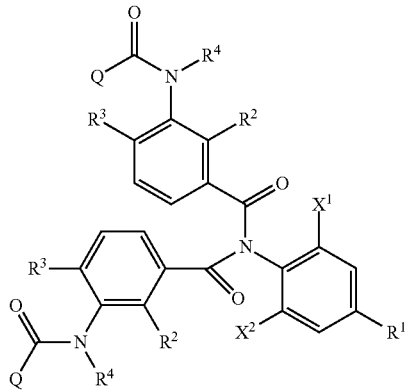

(IV)

in Formula (IV), $R^1$, $X^1$, $X^2$, $R^2$, $R^3$, $R^4$, and Q are the same as $R^1$, $X^1$, $X^2$, $R^2$, $R^3$, $R^4$, and Q in Formula (I), and two of $R^2$, $R^3$, $R^4$ and Q may be the same or different at each occurrence, respectively; and the process b comprises hydrolyzing the imide compound of Formula (IV), to thereby obtain the aromatic amide derivative of Formula (I).

2. The method of producing an aromatic amide derivative according to claim 1, wherein each of $X^1$ and $X^2$ in Formulae (I), (II) and (IV) independently represents a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, or a $C_1$-$C_4$ haloalkylsulfonyl group;

each of $R^2$ and $R^3$ in Formulae (I), (III) and (IV) independently represents a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group; and $R^4$ in Formulae (I), (III) and (IV) represents:
a hydrogen atom;
a $C_1$-$C_4$ alkyl group;
a $C_1$-$C_4$ haloalkyl group;
a $C_1$-$C_4$ alkylcarbonyl group;
a $C_1$-$C_4$ haloalkylcarbonyl group;
a $C_1$-$C_4$ alkoxycarbonyl group;
a $C_1$-$C_4$ haloalkoxycarbonyl group;
a $C_1$-$C_4$ alkylsulfonyl group;
a $C_1$-$C_4$ haloalkylsulfonyl group; or
a $C_1$-$C_4$ alkyl group or a $C_1$-$C_4$ haloalkyl group, substituted by 1 to 9 substituents, which may be the same or different, selected from the group consisting of a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a $C_1$-$C_4$ alkylcarbonyl group, a $C_1$-$C_4$ alkoxycarbonyl group, a di-$C_1$-$C_4$ alkylaminocarbonyl group, a cyano group, and a nitro group.

3. The method of producing an aromatic amide derivative according to claim 2, wherein $R^2$ in Formulae (I), (III) and (IV) represents a hydrogen atom, a halogen atom, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylsulfonyl group, a $C_1$-$C_4$ haloalkylsulfonyl group, a $C_1$-$C_4$ alkylamino group, a di-$C_1$-$C_4$ alkylamino group, a cyano group, or a nitro group;

$R^3$ in Formulae (I), (III) and (IV) represents a hydrogen atom, a halogen atom, a $C_1$-$C_4$ alkoxy group, a cyano group, or a nitro group; and Q in Formulae (I), (III) and (IV) represents:
a $C_1$-$C_4$ alkylaminocarbonyl group;
a $C_1$-$C_4$ haloalkylaminocarbonyl group;
a di-$C_1$-$C_4$ alkylaminocarbonyl group;
a di-$C_1$-$C_4$ haloalkylaminocarbonyl group;
a phenyl group;
a heterocyclic group;
a phenyl group substituted by 1 to 5 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group; or
a heterocyclic group substituted by 1 to 4 substituents, which may be the same or different, selected from the group consisting of a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a $C_1$-$C_4$ alkylamino group, a di-$C_1$-$C_4$ alkylamino group, a cyano group, and a nitro group.

4. The method of producing an aromatic amide derivative according to claim 2, wherein $R^2$ in Formulae (I), (III) and (IV) represents a hydrogen atom, a halogen atom, a $C_1$-$C_4$ alkoxy group, a $C_1$-$C_4$ alkylamino group, a di-$C_1$-$C_4$ alkylamino group, a cyano group, or a nitro group; and $R^4$ in Formulae (I), (III) and (IV) represents a hydrogen atom, a $C_1$-$C_4$ alkyl group, or a $C_1$-$C_4$ haloalkyl group.

5. The method of producing an aromatic amide derivative according to claim 3, wherein $R^2$ in Formulae (I), (III) and (IV) represents a hydrogen atom, a halogen atom, or a $C_1$-$C_4$ alkoxy group;

$R^3$ in Formulae (I), (III) and (IV) represents a hydrogen atom, a halogen atom, or a cyano group; and Q in Formulae (I), (III) and (IV) represents:
a di-$C_1$-$C_4$ alkylaminocarbonyl group;
a phenyl group;
a heterocyclic group;
a phenyl group substituted by 1 to 5 substituents, which may be the same or different, selected from the group consisting of a halogen atom, a cyano group, a nitro group, and a $C_1$-$C_4$ haloalkyl group; or
a heterocyclic group substituted by 1 to 4 substituents, which may be the same or different, selected from the group consisting of a halogen atom, a cyano group, a nitro group, and a $C_1$-$C_4$ haloalkyl group.

6. The method of producing an aromatic amide derivative according to claim 5, wherein $R^2$ in Formulae (I), (III) and (IV) represents a hydrogen atom or a halogen atom;

$R^4$ in Formulae (I), (III) and (IV) represents a hydrogen atom or a $C_1$-$C_4$ alkyl group; and Q in Formulae (I), (III) and (IV) represents:

a phenyl group;

a pyridyl group;

a phenyl group substituted by 1 to 5 substituents, which may be the same or different, selected from the group consisting of a halogen atom, a cyano group, and a nitro group; or a pyridyl group substituted by 1 to 4 substituents, which may be the same or different, selected from the group consisting of a halogen atom, a cyano group, a nitro group, and a $C_1$-$C_4$ haloalkyl group.

7. The method of producing an aromatic amide derivative according to claim 1, wherein the method further comprises the following process c, process d, and process e, wherein:

the process c comprises obtaining a carboxylic acid compound of the following Formula (V) produced together with the aromatic amide derivative of Formula (I) in the process b, and halogenating or esterifying the carboxylic acid compound, to thereby obtain a carboxylic acid derivative reproducing compound of the following Formula (IIIa):

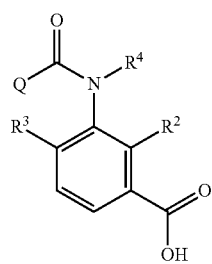

(V)

in Formula (V), $R^2$, $R^3$, $R^4$ and Q are the same as $R^2$, $R^3$, $R^4$ and Q in Formula (III);

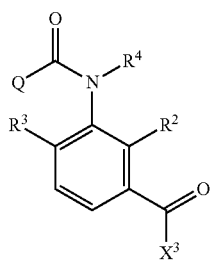

(IIIa)

in Formula (IIIa), $R^2$, $R^3$, $R^4$ and Q are the same as $R^2$, $R^3$, $R^4$ and Q in Formula (V) and $X^3$ in Formula (IIIa) is the same as $X^3$ in Formula (III);

the process d comprises allowing the carboxylic acid derivative reproducing compound obtained in the process c and the aniline derivative of Formula (II) to react with each other in the presence of a base to obtain the imide compound of Formula (IV); and the process e comprises hydrolyzing the imide compound of Formula (IV) obtained in the process d to obtain the aromatic amide derivative of Formula (I).

8. The method of producing an aromatic amide derivative according to claim 7, wherein $R^2$ in Formulae (III), (V) and (IIIa) represents a hydrogen atom, a halogen atom, a $C_1$-$C_4$ alkoxy group, a $C_1$-$C_4$ alkylamino group, a di-$C_1$-$C_4$ alkylamino group, a cyano group, or a nitro group;

$R^3$ in Formulae (III), (V) and (IIIa) represents a hydrogen atom or a halogen atom;

$R^4$ in Formulae (III), (V) and (IIIa) represents a hydrogen atom, a $C_1$-$C_4$ alkyl group, or a $C_1$-$C_4$ haloalkyl group; and Q in Formulae (III), (V) and (IIIa) represents:

a di-$C_1$-$C_4$ alkylaminocarbonyl group;

a phenyl group;

a heterocyclic group;

a phenyl group substituted by 1 to 5 substituents, which may be the same or different, selected from the group consisting of a halogen atom, a cyano group, a nitro group, and a $C_1$-$C_4$ haloalkyl group; or a heterocyclic group substituted by 1 to 4 substituents, which may be the same or different, selected from the group consisting of a halogen atom, a cyano group, a nitro group, and a $C_1$-$C_4$ haloalkyl group;

wherein the heterocyclic group is a pyridyl group, a pyridyl-N-oxide group, a pyrimidyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

9. The method of producing an aromatic amide derivative according to claim 7, wherein $R^2$ in Formulae (III), (V) and (IIIa) represents a hydrogen atom or a halogen atom;

$R^4$ in Formulae (III), (V) and (IIIa) represents a hydrogen atom or a $C_1$-$C_4$ alkyl group; and Q in Formulae (III), (V) and (IIIa) represents:

a di-$C_1$-$C_4$ alkylaminocarbonyl group;

a phenyl group;

a pyridyl group;

a phenyl group substituted by 1 to 5 substituents, which may be the same or different, selected from the group consisting of a halogen atom, a cyano group, and a nitro group; or a pyridyl group substituted by 1 to 4 substituents, which may be the same or different, selected from the group consisting of a halogen atom and a $C_1$-$C_4$ haloalkyl group.

* * * * *